US009982239B2

(12) United States Patent
Gomez Sebastian et al.

(10) Patent No.: US 9,982,239 B2
(45) Date of Patent: *May 29, 2018

(54) BACULOVIRAL DNA ELEMENTS FOR THE EXPRESSION OF RECOMBINANT PROTEINS IN A HOST CELL

(75) Inventors: Silvia Gomez Sebastian, Madrid (ES); Javier López Vidal, Madrid (ES); José Angel Martinez Escribano, Madrid (ES)

(73) Assignee: ALTERNATIVE GENE EXPRESSION S.L., Madrid (ES)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/407,618

(22) PCT Filed: Jun. 12, 2012

(86) PCT No.: PCT/EP2012/061081
§ 371 (c)(1),
(2), (4) Date: Aug. 14, 2015

(87) PCT Pub. No.: WO2012/168492
PCT Pub. Date: Dec. 13, 2012

(65) Prior Publication Data
US 2015/0353898 A1 Dec. 10, 2015

(51) Int. Cl.
*C12N 7/00* (2006.01)
*C12N 15/86* (2006.01)

(52) U.S. Cl.
CPC .............. *C12N 7/00* (2013.01); *C12N 15/86* (2013.01); *C12N 2710/14021* (2013.01); *C12N 2710/14122* (2013.01); *C12N 2830/20* (2013.01); *C12N 2830/30* (2013.01)

(58) Field of Classification Search
None
See application file for complete search history.

(56) References Cited

U.S. PATENT DOCUMENTS

| | | | |
|---|---|---|---|
| 5,965,393 | A | 10/1999 | Hasnain et al. |
| 6,322,781 | B1 | 11/2001 | McCutchen |
| 9,701,983 | B2 | 7/2017 | Gomez Sebastian et al. |
| 9,879,280 | B2 | 1/2018 | Gomez Sebastian et al. |
| 2003/0027257 | A1 | 2/2003 | Iatrou et al. |
| 2009/0068703 | A1 | 3/2009 | Chao et al. |
| 2009/0162398 | A1 | 6/2009 | Wu |

FOREIGN PATENT DOCUMENTS

| | | |
|---|---|---|
| EP | 1811027 A1 | 7/2007 |
| ES | 2232308 B1 | 5/2005 |
| KR | WO-20010074351 A | 8/2001 |
| WO | WO-1995017515 A1 | 6/1995 |
| WO | WO-2005/085456 A1 | 9/2005 |
| WO | WO-2010/025764 A1 | 3/2010 |
| WO | WO-2011020710 A2 | 2/2011 |
| WO | WO-2011/069562 A1 | 6/2011 |
| WO | WO-2012/168492 A2 | 12/2012 |
| WO | WO-2012/168789 A2 | 12/2012 |
| WO | WO-2012/169940 A2 | 12/2012 |

OTHER PUBLICATIONS

Alves, C.A., et al., "*hycu-hr6*, A large homologous region of the *Hypantria cunea* nucleopolyhedrovirus genome, as a powerful and versatile enhancer in insect expression systems", *Virus Genes, Kluwer Academic Publishers*, BO, vol. 39, No. 3, 2009, pp. 403-408.

Baek, J.O., et al., "Production and purification of human papillomavirus type 33 L1 virus-like particles from Spodoptera frugiperda 9 cells using two-step column chromatography", *Protein Expression and Purification*, vol. 75, No. 2, 2010, pp. 211-217.

Berger, I., et al., "Baculovirus expression system for heterologus multiprotein complexes", *Nature Biotechnology*, vol. 22, No. 12, 2004, pp. 1583-1587.

Bieniossek, C., et al.,"MultiBac: expanding the research toolbox for multiprotein complexes", *Trends in Biochemical Sciences*, vol. 37, No. 2, 2012, pp. 49-57.

Crouch, E.A., et al., "Effects of baculovirus transactivators IE-1 and IE-2 on the *Drosophila* heat shock 70 promoter in two insect cell lines", *Archives of Virology; Official Journal of the Virology Division of the International Union of Microbiological Societies*, Springer-Verlag VI, vol. 150, No. 8, 2005, pp. 1563-1578.

Dai, X., "The acidic activation domains of the baculovirus transactivators IE1 and IE0 are functional for transcriptional activation in both insect and mammalian cells", *Journal of General Virology*, vol. 85, No. 3, 2004, pp. 573-582.

Fan, H., et al., "Construction and immunogenicity of recombinant pseudotype baculovirus expressing the capsid protein of porcine circovirus type 2 in mice", *Journal of Virological Methods*, vol. 150, No. 1-2, 2008, pp. 21-26.

Gomez-Casado, E., et al., "Insect larvae biofactories as a platform for influenza vaccine production", *Protein Expression and Purification*, vol. 79, 2011, pp. 35-43.

(Continued)

*Primary Examiner* — Addison D Ault
(74) *Attorney, Agent, or Firm* — McCarter & English, LLP; Jill Ann Mello

(57) ABSTRACT

Reagents and methods are provided that allow for an improved expression of a recombinant protein. More specifically, the introduction of recombinant DNA elements into a host cell allows for the increased expression of a recombinant protein, an improvement of the correct folding of said protein and an increase in cell viability and proliferation of the host cell, These recombinant DNA elements can be introduced into host cells, for example, via a recombinant baculovirus, which has incorporated said elements. The recombinant DNA elements include nucleic acids encoding transcriptional regulators, such as IE-0 and IE-1, transcriptional enhancer elements, such as the homologous region (hr) and promoters.

7 Claims, 11 Drawing Sheets

(56) References Cited

OTHER PUBLICATIONS

Gomi, S., et al., "Sequence analysis of the genome of *Bombyx* mori nucleopolyhedrovirus", *Journal of General Virology*, vol. 80, No. 5, 1999, 1323-1337.
Guo, M., et al., "Expression and Self-Assembly in Baculovirus of Porcine Enteric Calicivirus Capsids into Virus-Like Particles and Their Use in an Enzyme-Linked Immunosorbent Assay for Antibody Detection in Swine", *Journal of Clinical Microbiology*, vol. 39, No. 4, 2001, pp. 1487-1493.
Hashimoto, Y., et al., "Ao38, a new cell line from eggs of the black witch moth, *Ascalapha odorata* (Lepidoptera: Noctuidae), is permissive for AcMNPV infection and produces high levels of recombinant proteins", *BMC Biotechnology*, vol. 10, 2010, p. 50.
Hill-Perkins, M.S., et al., "A baculovirus expression vector derived from the basic protein promoter of *Autographa californica* nuclear polyhedrosis virus", *Journal of General Virology*, vol. 71, 1990, pp. 971-976.
Hitchman, R.B., et al., "Baculovirus expression systems for recombinant protein production in insect cells", *Recent Patents on Biotechnology*, vol. 3, No. 1, 2009, pp. 46-54.
International Search Report and Written Opinion of PCT/EP2012/061081, dated Feb. 19, 2013.
International Search Report and Written Opinion of PCT/EP2012/061088, dated Mar. 6, 2013.
International Search Report and Written Opinion of PCT/EP2013/075812, dated Apr. 25, 2014.
Kang, W., "IE1 and hr facilitate the localization of *Bombyx mori* nucleopolyhedrovirus ORF8 to specific nuclear sites", *Journal of General Virology*, vol. 86, No. 11, 2005, pp. 3031-3038.
Kanginakudru, S., et al., "Targeting ie-1 gene by RNAi induces baculoviral resistance in lepidopteran cell lines and in transgenic silkworms", *Insect Molecular Biology*, vol. 16, No. 5, 2007, pp. 635-644.
Kawasaki, Y., "Analysis of baculovirus IE1 in living cells: dynamics and spatial relationships in viral structural proteins", *Journal of General Virology*, ol. 85, No. 12, 2004, pp. 3575-3583.
Lin, X., et al., "Baculovirus immediately early 1, a mediator for homologous regions enhancer function in trans", *Virology Journal*, vol. 7, No. 32, 2010.
Lo, H.-R., et aL, "Novel Baculovirus DNA Elements Strongly Stimulate Activities of Exogenous and Endogenous Promoters", *Journal of Biological Chemistry*, vol. 277, No. 7, 2002, pp. 5256-5264.
López-Vidal, J., et al., "Characterization of a Trichoplusia ni hexamerin-derived promoter in the AcMNPV baculovirus vector", *Journal of Biotechnology*, vol. 165, No. 3-4, 2013, pp. 201-208.
Majima, K., et al., "Divergence and evolution of homologous regions of *Bombyx mori* nuclear polyhedrosis virus", *Journal of Virology*, vol. 67, No. 12, 1993, pp. 7513-7521.
Nagai, S., et al., "Comparative transient expression assay analysis of *hycu-hr6-* and IE1-dependent regulation of baculovirus *gp64* early promoters in three insect cell lines", *Virus Research*, Amsterdam, NL, vol. 155, No. 1, 2011, pp. 83-90.
Nagamine, T., et al., "Focal Distribution of Baculovirus IE1 Triggered by its Binding to the hr DNA Elements", *Journal of Virology*, vol. 79, No. 1, 2004, pp. 39-46.
Nagamine, T., et al., "Induction of a sub-nuclear structure by the simultaneous expression of baculovirus proteins, IE1, LEF3, and P143 in the presence of hr", *Virology, Academic Press,* Orlando, US, vol. 352, No. 2, 2006, pp. 400-407.
Nettleship, J.E., et aL, "Recent advances in the production of proteins in insect and mammalian cells for structural biology", *Journal of Structural Biology, Academic Press*, US, vol. 172, No. 1, 2010, pp. 55-65.
Ogawa, S., et al., "Generation of a transgenic silkworm that secretes recombinant proteins in the sericin layer of cocoon: Production of recombinant human serum albumin", *Journal of Biotechnology,* Elsevier Science Publishers, vol. 128, No. 3, 2007, pp. 531-544.

Okano, L., et al., "Colocalization of baculovirus IE-1 and two DNA-binding proteins, DBF and LEF-3, to viral replication factories", *Journal of Virology*, vol. 73, No. 1, 1999, pp. 110-119.
Olson, V.A., et al., "The highly conserved basic domain I of baculovirus IE1 is required for hr enhancer DNA binding and hr-dependent transactivation", *Journal of Virology, The American Society for Microbiology*, US, vol. 77, No. 10, 2003, pp. 5668-5677.
Passarelli, A.L., et al., "Three baculovirus genes involved in late and very late gene expression: ie-1, ie-n, and lef-2", *Journal of Virology*, vol. 67, No. 4, 1993, pp. 2149-2158.
Perez-Filgueira, D.M., et al., "Development of a low-cost, insect larvae-derived recombinant subunit vaccine against RHDV", *Virology*, vol. 364, No. 2, 2007, pp. 422-430.
Radner, S., et al., "Transient transfection couples to baculovirus infection for rapid protein expression screening in insect cells", *Journal of Structural Biology*, vol. 179, No. 1, 2012, pp. 46-55.
Rodems, S. M., et al., "DNA-dependent transregulation by IE1 of *Autographa californica* nuclear polyhedrosis virus: IE1 domains required for transactivation and DNA binding", *Journal of Virology*, vol. 71, 1997, pp. 9270-9277.
Senger, T., et al., "Enhanced papillomavirus-like particle production in insect cells", *Virology*, vol. 388, No. 2, 2009, pp. 344-353.
Smith, G.E., et al., "Production of human beta interferon in insect cells infected with a baculovirus expression vector", *Molecular Cellular Biology*, vol. 3, 1983, pp. 2156-2165.
Taticek, R.A., el al., "Comparison of growth and recombinant protein expression in two different insect cells lines in attached and suspension culture", *Biotechnology Progress*, vol. 17, No. 4, 2001, pp. 676-684.
Tomita, M., et al., "A germline transgenic silkworm that secretes recombinant proteins in the sericin layer of cocoon", *Transgenic Research, Kluwer Academic Publishers-Plenum Publishers*, vol. 16, No. 4, 2007, pp. 449-465.
Valdes, V.J., et al., "Using double-stranded RNA to prevent in vitro and in vivo viral infections by recombinant baculovirus", *Journal of Biological Chemistry*, vol. 278, No. 21, 2003, pp. 19317-19324.
Venkaiah, B., et al., "An additional homologous region (hrl) sequence in the *Autographa californica* multinucleocapsid polyhedrosis virus genome promote hyperexpression of foreign genes," *Biochemistry*, vol. 43, No. 25, 2004, pp. 8143-8151.
Bryan et al., 2013, http://www.elsevierblogs.com/currentcomments/?p=962 Implications of protein fold switching, posted on Feb. 4, 2013, last retrieved on Aug. 19, 2015.
Chao et al., Issued_Patents_NA, Sequence 2, U.S. Appl. No. 11/851,042 (U.S. Pat. No. 8,105,827 B2), current filing date, Jan. 16, 2008, computer printout pp. 2-5.
Chattopadhyay et al., Effect of single amino acid mutations in the conserved GDNQ motif of L protein on Rinderpest virus on RNA synthesis in vitro and in vivo. *Virus Research*, 2004, vol. 99, pp. 139-145.
Lepidoptera—Wikipedia, the free encyclopedia pp. 1-29, downloaded on Aug. 30, 2016.
Morrison et al., 2007, N_Geneseq Accession No. AEX83551, computer printout pp. 71-73.
Pandey, Abstract of the 59th Southeast Regional Meeting of the American Chemical Society, Greenville, SC, United States, GEN-671, 2007. Publisher: American Chemical Society, Washington D.C.
Possee et al., 1994, Gen Embl Accession No. M75679, computer printout pp. 4-6.
Tomasinsig et al., The Cathelicidins—Structure, Function and Evolution. *Current Protein and Peptide Science*, 2005, vol. 6, pp. 23-34.
Guarino et al., Interspersed Homologous DNA of Autographa californica Nuclear Polyhedrosis Virus Enhances Delayed-Early Gene Expression. J Virol. Oct. 1986;60(1):215-23.
Gómez-Sebastián et al., Significant productivity improvement of the baculovirus expression vector system by engineering a novel expression cassette. PLoS One. May 13, 2014;9(5):e96562. 10 pages.
Kimchi-Sarfaty et al., A "silent" polymorphism in the MDR1 gene changes substrate specificity. Science. Jan. 26, 2007;315(5811):525-8.

(56) References Cited

OTHER PUBLICATIONS

Knebel et al., The promoter of the late p10 gene in the insect nuclear polyhedrosis virus Autographa californica: activation by viral gene products and sensitivity to DNA methylation. Embo J. May 1985;4(5):1301-6.

Lopez-Vidal et al., Insect-derived promoters for baculovirus vectors improvement. FEBS Journal. 2011;278(Suppl. 1):438, Abstract P33.15. 1 page.

Ngo et al., Computational Complexity, Protein Structure Prediction, and the Levinthal Paradox. The Protein Folding Problem and Tertiary Structure Prediction, Merz et al., (Eds.), Birkhauserm Boston, Boston, MA, pp. 433 and 492-495, 1994.

Prikhod'Ko et al., Induction of apoptosis by baculovirus transactivator IE1. J Virol. Oct. 1996;70(10):7116-24.

Rudinger, Characteristics of the amino acids as components of a peptide hormone sequence. Peptide Hormones, Parsons (Ed.), 1976, University Park Press, Baltimore, MD, Chapter 1, pp. 1-7.

Voet, et al., Biochemistry, 3rd Edition, John Wiley and Sons, New York, 1990, pp. 126-128.

Weyer et al., a baculovirus dual expression vector derived from the Autographa californica nuclear polyhedrosis virus polyhedrin and p10 promoters: co-expression of two influenza virus genes in insect cells. J Gen Virol. Dec. 1991;72(Pt 12):2967-74.

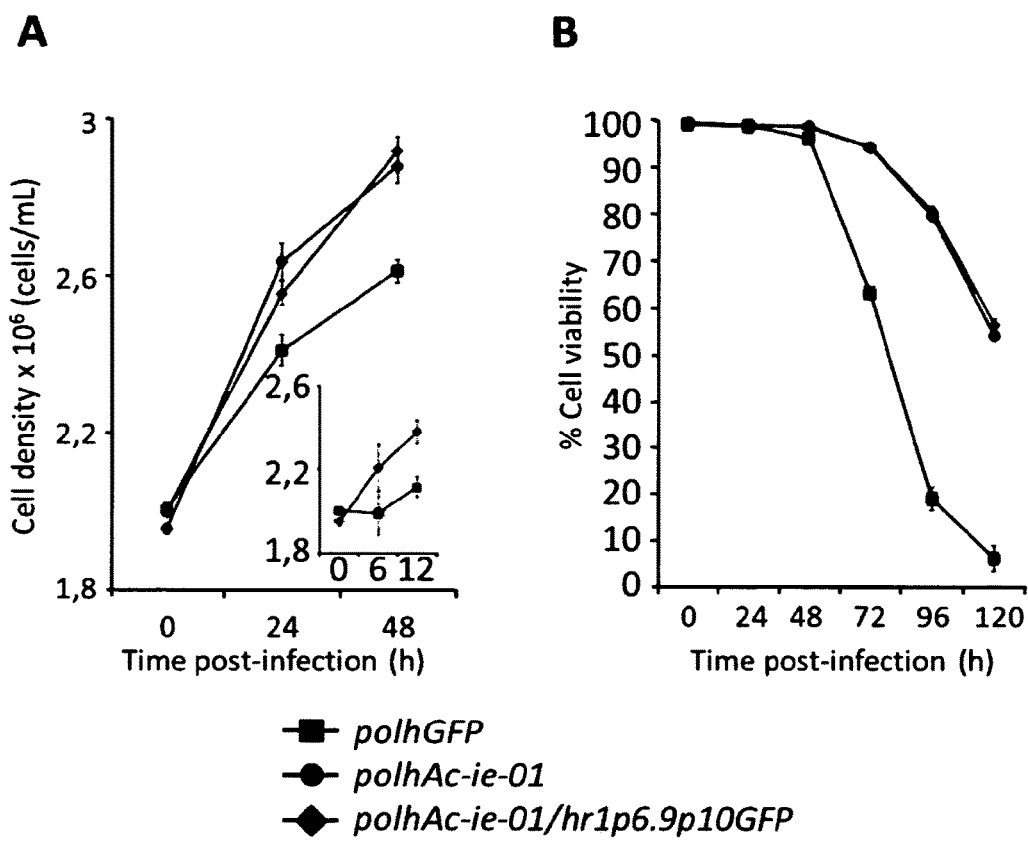
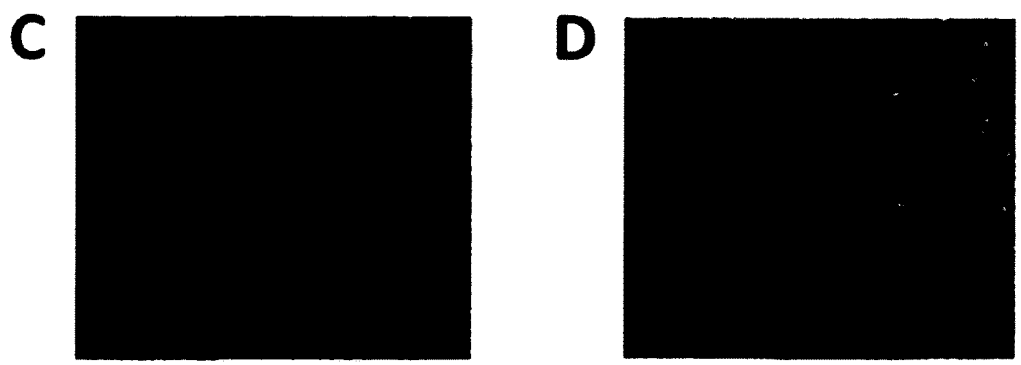
Figure 6

A

CTTGAATGTTAGTGAAACCCCCTGCGACACAAGTATTACATTCCTTAGTGCTTGAATCCTTAGGAAAGAAAAGCCAATTTT
                                                              Br-C
CAAAATCTTAGCACTTGTTAACTCGCGAAAAAGACCAACAGATTTCCCATACTACAATTCGACATTAGAAATGTAAACCCA
TTATCATTATTTACGCCTCATTTCCATCCAATAATAAGTTTAAGTACGTTGAGATAAAACTGGCTTACCTAGAACTTGACAT
GGCGACCTCTTGCACTCTGTATCTCAAGTCAACTTTCTCTATCCAAATATTTGATAACATTTGACATGATATTGAAGTAAGA
TTGTTACTAAGGCTTACATTGTAATATTACTGACGCAAGTTCTTATCAATAAAAAGCTGAAAACAAAAAAAAAAACATC
                                              EcR
GATTAGGGTGACTGAAGGTTACATTGGGGTAGGTTATGGTTAATACGTAATGGTTTAACACCAAAACGATATCATGGATT
GACTTTATAAATTTTATATAAGGTGTAATAATATTTTTAATGAGTGGACGCGTCGGGTCAATGTCCGCCTATTGACGTCAT
   Br-C                                                  EcR
AACATATTAGGTGATTATATTAAAAATACTCAAATATTACTTGCAAGTTTAAGTTTCATCATAATCTGATCATAAGTTTCACC
CAAACAGAAACCAAAAGCATAACTATCTGCTATTTGAATATCTTTAGCTTCCCATGAAGAAAGATTACCGTAACCATCACT
                        Br-C
AGGATTTTATACGATTGTAGAAAATAAAGTATTCTCAGTCTCTTTCAGTTTAAAATCTGCTGGCATTTTTACAAGTCGCTG
                                              EcR
TATCAGTCAATGTTTATACAATATGTCAATGTACTTCGTATTAATCAGAAAAAAATATTCTACTAGTTTTGATAAGCTATCA
                 EcR
CTTTTGTTACATTGTACTGCCCTTTACAGTTCATCAGGTATTTATGAATGACATATTGGAGAAACATCGTAATCAGTCCAGT
ATAAAAGGGGTGCATTCTCGGTAAGAGTACAGTTGAACTCACATCGAGTTAACTCCACG
                          ▲

B

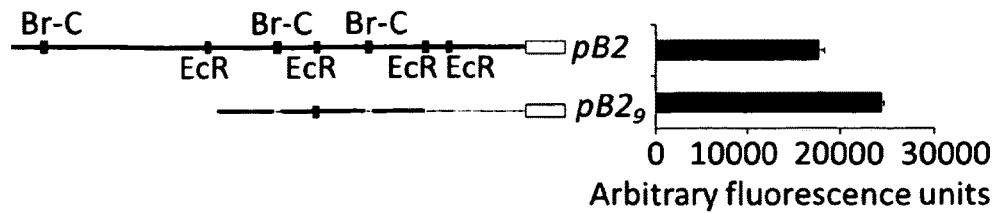

Figure 9

SEQUENCE LISTING

<160> NUMBER OF SEQ ID NOS: 41

<210> SEQ ID NO 1

<400> SEQUENCE: 1

000

<210> SEQ ID NO 2
<211> LENGTH: 1749
<212> TYPE: DNA
<213> ORGANISM: Autographa californica nucleopolyhedrovirus

<400> SEQUENCE: 2
atgactcaaa tcaacttcaa cgcttcctac acctctgcca gcactccctc tcgtgctagc          60

```
ttcgacaact catactcgga gttctgcgac aagcaaccta acgattactt gtcttactac    120
aaccacccaa ccccggacgg agctgatact gtcatctccg actctgaaac cgctgccgct    180
agcaacttcc tcgcctcagt taactcgctc actgacaacg atttggtgga gtgtctgctc    240
aagaccactg acaacctgga ggaagctgtg tcctctgcct actacagcga gtcactcgaa    300
cagccagtgg tcgaacaacc ctctcctagc tcagcttacc acgccgagtc cttcgaacac    360
tctgctggtg tcaaccagcc gtcggccaca ggcaccaaga ggaagttgga cgagtacctg    420
gataactccc agggagttgt gggtcaattc aacaagatca agttgagacc taagtacaag    480
aagagcacca tccagtcatg cgctacactg aacaaaccat caaccacaa cactaacatc    540
tgtacagtgg cttccaccca ggagatcact cactacttca caaacgactt cgcccctac    600
ctgatgaggt tcgacgataa cgactacaac tcgaacagat tctccgatca catgtctgaa    660
accggttact acatgttcgt cgttaagaag tccgaggtga agcctttcga aatcatcttc    720
gccaagtacg tctctaacgt ggtctacgag tacacaaaca actactacat ggttgacaac    780
cgtgtgttcg ttgtgacctt cgataagatc cgcttcatga tcagctacaa cctggttaag    840
gagactggca tcgaaatccc acactcacag gacgtctgca acgatgagac cgccgctcaa    900
aactgcaaga agtgtcactt cgtggacgtc caccacacat tcaaggccgc tctgacctcc    960
tacttcaacc tcgatatgta ctacgctcag acaaccttcg tgaccttgct gcaatcactc    1020
ggcgagcgta agtgtggatt cctcttgtcg aagttgtacg agatgtacca ggacaagaac    1080
ctcttcactt tgcccatcat gctgagccgc aaggaatcaa acgagatcga aaccgcctct    1140
aacaacttct tcgtctcgcc atacgtttcc cagatcctca agtactcgga gtccgtccaa    1200
ttcccggaca ccctcccaa caagtacgtc gttgataacc tgaacctcat cgtgaacaag    1260
aagagcactc tgacatacaa gtactcgtcc gtcgctaacc tgctcttcaa caactacaag    1320
taccacgaca acatcgcttc taacaacaac gccgagaacc tcaagaaggt caagaaggaa    1380
gacggaagca tgcacatcgt tgagcagtac ttgactcaaa acgtcgataa cgttaagggt    1440
cacaacttca tcgtgttgtc cttcaagaac gaggaaaggc tgaccatcgc taagaagaac    1500
aaggagttct actggatctc tggcgaaatc aaggacgttg atgtgagcca ggtcatccaa    1560
aagtacaaca gattcaagca ccacatgttc gtgatcggca aggtcaaccg tcgcgagtca    1620
actacactgc acaacaactt gctgaagctc ttggccttga tcctgcaggg actggtgcca    1680
ctctccgacg ccatcacatt cgccgagcaa aagctcaact gcaagtacaa gaagttcgag    1740
ttcaactaa                                                           1749

<210> SEQ ID NO 3
<211> LENGTH: 1911
<212> TYPE: DNA
<213> ORGANISM: Autographa californica nucleopolyhedrovirus

<400> SEQUENCE: 3
atgatccgta catccagcca cgtcctgaac gtccaagaaa acatcatgac ttccaactgt     60
gcttccagcc cctactcctg tgaggccact tcagcctgcg ctgaggccca gcaactgcag    120
gtggacacag gtggcgataa gatcgtgaac aaccaggtca cctgactca aatcaacttc    180
aacgcttcct acacctctgc cagcactccc tctcgtgcta gcttcgacaa ctcatactcg    240
gagttctgcg acaagcaacc taacgattac ttgtcttact acaaccaccc aaccccggac    300
ggagctgata ctgtcatctc cgactctgaa accgctgccg ctagcaactt cctcgcctca    360
gttaactcgc tcactgacaa cgatttggtg gagtgtctgc tcaagaccac tgacaacctg    420
```

```
gaggaagctg tgtcctctgc ctactacagc gagtcactcg aacagccagt ggtcgaacaa     480
ccctctccta gctcagctta ccacgccgag tccttcgaac actctgctgg tgtcaaccag     540
ccgtcggcca caggcaccaa gaggaagttg acgagtacc tggataactc ccagggagtt     600
gtgggtcaat tcaacaagat caagttgaga cctaagtaca agaagagcac catccagtca     660
tgcgctacac tggaacaaac catcaaccac aacactaaca tctgtacagt ggcttccacc     720
caggagatca ctcactactt cacaaacgac ttcgcccct acctgatgag gttcgacgat     780
aacgactaca actcgaacag attctccgat cacatgtctg aaaccggtta ctacatgttc     840
gtcgttaaga gtccgaggt gaagcctttc gaaatcatct tcgccaagta cgtctctaac     900
gtggtctacg agtacacaaa caactactac atggttgaca accgtgtgtt cgttgtgacc     960
ttcgataaga tccgcttcat gatcagctac aacctggtta aggagactgg catcgaaatc    1020
ccacactcac aggacgtctg caacgatgag accgccgctc aaaactgcaa gaagtgtcac    1080
ttcgtggacg tccaccacac attcaaggcc gctctgacct cctacttcaa cctcgatatg    1140
tactacgctc agacaacctt cgtgaccttg ctgcaatcac tcggcgagcg taagtgtgga    1200
ttcctcttgt cgaagttgta cgagatgtac caggacaaga acctcttcac tttgcccatc    1260
atgctgagcc gcaaggaatc aaacgagatc gaaaccgcct ctaacaactt cttcgtctcg    1320
ccatacgttt cccagatcct caagtactcg agtccgtcc aattcccgga caaccctccc     1380
aacaagtacg tcgttgataa cctgaacctc atcgtgaaca agaagagcac tctgacatac    1440
aagtactcgt ccgtcgctaa cctgctcttc aacaactaca agtaccacga caacatcgct    1500
tctaacaaca acgccgagaa cctcaagaag gtcaagaagg aagacggaag catgcacatc    1560
gttgagcagt acttgactca aaacgtcgat aacgttaagg gtcacaactt catcgtgttg    1620
tccttcaaga acgaggaaag gctgaccatc gctaagaaga acaaggagtt ctactggatc    1680
tctggcgaaa tcaaggacgt tgatgtgagc caggtcatcc aaaagtacaa cagattcaag    1740
caccacatgt tcgtgatcgg caaggtcaac cgtcgcgagt caactacact gcacaacaac    1800
ttgctgaagc tcttggcctt gatcctgcag ggactggtgc cactctccga cgccatcaca    1860
ttcgccgagc aaaagctcaa ctgcaagtac aagaagttcg agttcaacta a             1911
```

<210> SEQ ID NO 4
<211> LENGTH: 666
<212> TYPE: DNA
<213> ORGANISM: Autographa californica nucleopolyhedrovirus

<400> SEQUENCE: 4

```
atgactcaaa tcaacttcaa cgcttcctac acctctgcca gcactccctc tcgtgctagc      60
ttcgacaact catactcgga gttctgcgac aagcaaccta cgattactt gtcttactac     120 aaccaccaa ccccggacgg agctgatact gtcatctccg actctgaaac cgctgccgct    180
agcaacttcc tcgcctcagt taactcgctc actgacaacg atttggtgga gtgtctgctc    240
aagaccactg acaacctgga ggaagctgtg tcctctgcct actacagcga gtcactcgaa    300
cagccagtgg tcgaacaacc ctctcctagc tcagcttacc gcgccagatc cttcgaacac    360
tctgctggtg tcaaccagcc gtcggccaca ggcaccaaga ggaagttgga cgagtacctg    420
gataactccc agggagttgt gggtcaattc aacaagatca agttgagacc taagtacaag    480 aagagccacca tccagtcatg cgctacactg aacaaaccca tcaaccacaa cactaacatc    540
tgtacagtgg cttccaccca ggagatcact cactacttca aaacgactt cgccccctac    600
```

```
ctgatgaggt cgacgataa cgactacaac tcgaacagat tctccgatca catgtctgaa    660
accggt                                                              666

<210> SEQ ID NO 5
<211> LENGTH: 828
<212> TYPE: DNA
<213> ORGANISM: Autographa californica nucleopolyhedrovirus

<400> SEQUENCE: 5
atgatccgta catccagcca cgtcctgaac gtccaagaaa acatcatgac ttccaactgt     60
gcttccagcc cctactcctg tgaggccact tcagcctgcg ctgaggccca gcaactgcag    120
gtggacacag gtggcgataa gatcgtgaac aaccaggtca ccatgactca aatcaacttc    180
aacgcttcct acacctctgc cagcactccc tctcgtgcta gcttcgacaa ctcatactcg    240
gagttctgcg acaagcaacc taacgattac ttgtcttact acaaccaccc aaccccggac    300
ggagctgata ctgtcatctc cgactctgaa accgctgccg ctagcaactt cctcgcctca    360
gttaactcgc tcactgacaa cgatttggtg gagtgtctgc tcaagaccac tgacaacctg    420
gaggaagctg tgtcctctgc ctactacagc gagtcactcg aacagccagt ggtcgaacaa    480
ccctctccta gctcagctta ccacgccgag tccttcgaac actctgctgg tgtcaaccag    540
ccgtcggcca caggcaccaa gaggaagttg acgagtacc tggataactc ccaggagtt     600 gtgggtcaat tcaacaagat caagttgaga cctaagtaca agaagagcac catccagtca    660
tgcgctacac tggaacaaac catcaaccac aacactaaca tctgtacagt ggcttccacc    720
caggagatca ctcactactt cacaaacgac ttcgccccct acctgatgag gttcgacgat    780
aacgactaca actcgaacag attctccgat cacatgtctg aaaccggt              828

<210> SEQ ID NO 6
<211> LENGTH: 582
<212> TYPE: PRT
<213> ORGANISM: Autographa californica nucleopolyhedrovirus

<400> SEQUENCE: 6

Met Thr Gln Ile Asn Phe Asn Ala Ser Tyr Thr Ser Ala Ser Thr Pro
1               5                   10                  15

Ser Arg Ala Ser Phe Asp Asn Ser Tyr Ser Glu Phe Cys Asp Lys Gln
            20                  25                  30

Pro Asn Asp Tyr Leu Ser Tyr Tyr Asn His Pro Thr Pro Asp Gly Ala
        35                  40                  45

Asp Thr Val Ile Ser Asp Ser Glu Thr Ala Ala Ala Ser Asn Phe Leu
    50                  55                  60

Ala Ser Val Asn Ser Leu Thr Asp Asn Asp Leu Val Glu Cys Leu Leu
65                  70                  75                  80

Lys Thr Thr Asp Asn Leu Glu Glu Ala Val Ser Ser Ala Tyr Tyr Ser
                85                  90                  95

Glu Ser Leu Glu Gln Pro Val Val Glu Gln Pro Ser Pro Ser Ser Ala
            100                 105                 110

Tyr His Ala Glu Ser Phe Glu His Ser Ala Gly Val Asn Gln Pro Ser
        115                 120                 125

Ala Thr Gly Thr Lys Arg Lys Leu Asp Glu Tyr Leu Asp Asn Ser Gln
    130                 135                 140

Gly Val Val Gly Gln Phe Asn Lys Ile Lys Leu Arg Pro Lys Tyr Lys
145                 150                 155                 160

Lys Ser Thr Ile Gln Ser Cys Ala Thr Leu Glu Gln Thr Ile Asn His
```

```
                    165                 170                 175
Asn Thr Asn Ile Cys Thr Val Ala Ser Thr Gln Glu Ile Thr His Tyr
                180                 185                 190

Phe Thr Asn Asp Phe Ala Pro Tyr Leu Met Arg Phe Asp Asp Asn Asp
            195                 200                 205

Tyr Asn Ser Asn Arg Phe Ser Asp His Met Ser Glu Thr Gly Tyr Tyr
        210                 215                 220

Met Phe Val Val Lys Lys Ser Glu Val Lys Pro Phe Glu Ile Ile Phe
225                 230                 235                 240

Ala Lys Tyr Val Ser Asn Val Val Tyr Glu Tyr Thr Asn Asn Tyr Tyr
                245                 250                 255

Met Val Asp Asn Arg Val Phe Val Val Thr Phe Asp Lys Ile Arg Phe
                260                 265                 270

Met Ile Ser Tyr Asn Leu Val Lys Glu Thr Gly Ile Glu Ile Pro His
            275                 280                 285

Ser Gln Asp Val Cys Asn Asp Glu Thr Ala Ala Gln Asn Cys Lys Lys
        290                 295                 300

Cys His Phe Val Asp Val His His Thr Phe Lys Ala Ala Leu Thr Ser
305                 310                 315                 320

Tyr Phe Asn Leu Asp Met Tyr Tyr Ala Gln Thr Thr Phe Val Thr Leu
                325                 330                 335

Leu Gln Ser Leu Gly Glu Arg Lys Cys Gly Phe Leu Leu Ser Lys Leu
            340                 345                 350

Tyr Glu Met Tyr Gln Asp Lys Asn Leu Phe Thr Leu Pro Ile Met Leu
        355                 360                 365

Ser Arg Lys Glu Ser Asn Glu Ile Glu Thr Ala Ser Asn Asn Phe Phe
    370                 375                 380

Val Ser Pro Tyr Val Ser Gln Ile Leu Lys Tyr Ser Glu Ser Val Gln
385                 390                 395                 400

Phe Pro Asp Asn Pro Asn Lys Tyr Val Val Asp Asn Leu Asn Leu
                405                 410                 415

Ile Val Asn Lys Lys Ser Thr Leu Thr Tyr Lys Tyr Ser Ser Val Ala
                420                 425                 430

Asn Leu Leu Phe Asn Asn Tyr Lys Tyr His Asp Asn Ile Ala Ser Asn
            435                 440                 445

Asn Asn Ala Glu Asn Leu Lys Lys Val Lys Lys Glu Asp Gly Ser Met
        450                 455                 460

His Ile Val Glu Gln Tyr Leu Thr Gln Asn Val Asp Asn Val Lys Gly
465                 470                 475                 480

His Asn Phe Ile Val Leu Ser Phe Lys Asn Glu Glu Arg Leu Thr Ile
                485                 490                 495

Ala Lys Lys Asn Lys Glu Phe Tyr Trp Ile Ser Gly Glu Ile Lys Asp
            500                 505                 510

Val Asp Val Ser Gln Val Ile Gln Lys Tyr Asn Arg Phe Lys His His
        515                 520                 525

Met Phe Val Ile Gly Lys Val Asn Arg Arg Glu Ser Thr Thr Leu His
    530                 535                 540

Asn Asn Leu Leu Lys Leu Leu Ala Leu Ile Leu Gln Gly Leu Val Pro
545                 550                 555                 560

Leu Ser Asp Ala Ile Thr Phe Ala Glu Gln Lys Leu Asn Cys Lys Tyr
                565                 570                 575

Lys Lys Phe Glu Phe Asn
            580
```

<210> SEQ ID NO 7
<211> LENGTH: 636
<212> TYPE: PRT
<213> ORGANISM: Autographa californica nucleopolyhedrovirus

<400> SEQUENCE: 7

```
Met Ile Arg Thr Ser Ser His Val Leu Asn Val Gln Glu Asn Ile Met
1               5                   10                  15

Thr Ser Asn Cys Ala Ser Ser Pro Tyr Ser Cys Glu Ala Thr Ser Ala
            20                  25                  30

Cys Ala Glu Ala Gln Gln Leu Gln Val Asp Thr Gly Gly Asp Lys Ile
        35                  40                  45

Val Asn Asn Gln Val Thr Met Thr Gln Ile Asn Phe Asn Ala Ser Tyr
    50                  55                  60

Thr Ser Ala Ser Thr Pro Ser Arg Ala Ser Phe Asp Asn Ser Tyr Ser
65                  70                  75                  80

Glu Phe Cys Asp Lys Gln Pro Asn Asp Tyr Leu Ser Tyr Tyr Asn His
                85                  90                  95

Pro Thr Pro Asp Gly Ala Asp Thr Val Ile Ser Asp Ser Glu Thr Ala
            100                 105                 110

Ala Ala Ser Asn Phe Leu Ala Ser Val Asn Ser Leu Thr Asp Asn Asp
        115                 120                 125

Leu Val Glu Cys Leu Leu Lys Thr Thr Asp Asn Leu Glu Glu Ala Val
    130                 135                 140

Ser Ser Ala Tyr Tyr Ser Glu Ser Leu Glu Gln Pro Val Val Glu Gln
145                 150                 155                 160

Pro Ser Pro Ser Ser Ala Tyr His Ala Glu Ser Phe Glu His Ser Ala
                165                 170                 175

Gly Val Asn Gln Pro Ser Ala Thr Gly Thr Lys Arg Lys Leu Asp Glu
            180                 185                 190

Tyr Leu Asp Asn Ser Gln Gly Val Val Gly Gln Phe Asn Lys Ile Lys
        195                 200                 205

Leu Arg Pro Lys Tyr Lys Lys Ser Thr Ile Gln Ser Cys Ala Thr Leu
    210                 215                 220

Glu Gln Thr Ile Asn His Asn Thr Asn Ile Cys Thr Val Ala Ser Thr
225                 230                 235                 240

Gln Glu Ile Thr His Tyr Phe Thr Asn Asp Phe Ala Pro Tyr Leu Met
                245                 250                 255

Arg Phe Asp Asp Asn Asp Tyr Asn Ser Asn Arg Phe Ser Asp His Met
            260                 265                 270

Ser Glu Thr Gly Tyr Tyr Met Phe Val Val Lys Lys Ser Glu Val Lys
        275                 280                 285

Pro Phe Glu Ile Ile Phe Ala Lys Tyr Val Ser Asn Val Tyr Glu
    290                 295                 300

Tyr Thr Asn Asn Tyr Tyr Met Val Asp Asn Arg Val Phe Val Val Thr
305                 310                 315                 320

Phe Asp Lys Ile Arg Phe Met Ile Ser Tyr Asn Leu Val Lys Glu Thr
                325                 330                 335

Gly Ile Glu Ile Pro His Ser Gln Asp Val Cys Asn Asp Glu Thr Ala
            340                 345                 350

Ala Gln Asn Cys Lys Lys Cys His Phe Val Asp Val His His Thr Phe
        355                 360                 365

Lys Ala Ala Leu Thr Ser Tyr Phe Asn Leu Asp Met Tyr Tyr Ala Gln
```

```
                370                 375                 380
Thr Thr Phe Val Thr Leu Leu Gln Ser Leu Gly Glu Arg Lys Cys Gly
385                 390                 395                 400

Phe Leu Leu Ser Lys Leu Tyr Glu Met Tyr Gln Asp Lys Asn Leu Phe
                405                 410                 415

Thr Leu Pro Ile Met Leu Ser Arg Lys Glu Ser Asn Glu Ile Glu Thr
                420                 425                 430

Ala Ser Asn Asn Phe Phe Val Ser Pro Tyr Val Ser Gln Ile Leu Lys
                435                 440                 445

Tyr Ser Glu Ser Val Gln Phe Pro Asp Asn Pro Asn Lys Tyr Val
450                 455                 460

Val Asp Asn Leu Asn Leu Ile Val Asn Lys Lys Ser Thr Leu Thr Tyr
465                 470                 475                 480

Lys Tyr Ser Ser Val Ala Asn Leu Leu Phe Asn Asn Tyr Lys Tyr His
                485                 490                 495

Asp Asn Ile Ala Ser Asn Asn Ala Glu Asn Leu Lys Lys Val Lys
                500                 505                 510

Lys Glu Asp Gly Ser Met His Ile Val Glu Gln Tyr Leu Thr Gln Asn
                515                 520                 525

Val Asp Asn Val Lys Gly His Asn Phe Ile Val Leu Ser Phe Lys Asn
530                 535                 540

Glu Glu Arg Leu Thr Ile Ala Lys Lys Asn Lys Glu Phe Tyr Trp Ile
545                 550                 555                 560

Ser Gly Glu Ile Lys Asp Val Asp Val Ser Gln Val Ile Gln Lys Tyr
                565                 570                 575

Asn Arg Phe Lys His His Met Phe Val Ile Gly Lys Val Asn Arg Arg
                580                 585                 590

Glu Ser Thr Thr Leu His Asn Asn Leu Leu Lys Leu Leu Ala Leu Ile
                595                 600                 605

Leu Gln Gly Leu Val Pro Leu Ser Asp Ala Ile Thr Phe Ala Glu Gln
                610                 615                 620

Lys Leu Asn Cys Lys Tyr Lys Lys Phe Glu Phe Asn
625                 630                 635

<210> SEQ ID NO 8
<211> LENGTH: 222
<212> TYPE: PRT
<213> ORGANISM: Autographa californica nucleopolyhedrovirus

<400> SEQUENCE: 8

Met Thr Gln Ile Asn Phe Asn Ala Ser Tyr Thr Ser Ala Ser Thr Pro
1               5                   10                  15

Ser Arg Ala Ser Phe Asp Asn Ser Tyr Ser Glu Phe Cys Asp Lys Gln
                20                  25                  30

Pro Asn Asp Tyr Leu Ser Tyr Tyr Asn His Pro Thr Pro Asp Gly Ala
                35                  40                  45

Asp Thr Val Ile Ser Asp Ser Glu Thr Ala Ala Ser Asn Phe Leu
        50                  55                  60

Ala Ser Val Asn Ser Leu Thr Asp Asn Asp Leu Val Glu Cys Leu Leu
65                  70                  75                  80

Lys Thr Thr Asp Asn Leu Glu Glu Ala Val Ser Ser Ala Tyr Tyr Ser
                85                  90                  95

Glu Ser Leu Glu Gln Pro Val Val Glu Gln Pro Ser Pro Ser Ser Ala
                100                 105                 110
```

```
Tyr His Ala Glu Ser Phe Glu His Ser Ala Gly Val Asn Gln Pro Ser
            115                 120                 125

Ala Thr Gly Thr Lys Arg Lys Leu Asp Glu Tyr Leu Asp Asn Ser Gln
130                 135                 140

Gly Val Val Gly Gln Phe Asn Lys Ile Lys Leu Arg Pro Lys Tyr Lys
145                 150                 155                 160

Lys Ser Thr Ile Gln Ser Cys Ala Thr Leu Glu Gln Thr Ile Asn His
                165                 170                 175

Asn Thr Asn Ile Cys Thr Val Ala Ser Thr Gln Glu Ile Thr His Tyr
            180                 185                 190

Phe Thr Asn Asp Phe Ala Pro Tyr Leu Met Arg Phe Asp Asp Asn Asp
        195                 200                 205

Tyr Asn Ser Asn Arg Phe Ser Asp His Met Ser Glu Thr Gly
210                 215                 220
```

<210> SEQ ID NO 9
<211> LENGTH: 276
<212> TYPE: PRT
<213> ORGANISM: Autographa californica nucleopolyhedrovirus

<400> SEQUENCE: 9

```
Met Ile Arg Thr Ser Ser His Val Leu Asn Val Gln Glu Asn Ile Met
1               5                   10                  15

Thr Ser Asn Cys Ala Ser Ser Pro Tyr Ser Cys Glu Ala Thr Ser Ala
            20                  25                  30

Cys Ala Glu Ala Gln Gln Leu Gln Val Asp Thr Gly Gly Asp Lys Ile
        35                  40                  45

Val Asn Asn Gln Val Thr Met Thr Gln Ile Asn Phe Asn Ala Ser Tyr
50                  55                  60

Thr Ser Ala Ser Thr Pro Ser Arg Ala Ser Phe Asp Asn Ser Tyr Ser
65                  70                  75                  80

Glu Phe Cys Asp Lys Gln Pro Asn Asp Tyr Leu Ser Tyr Tyr Asn His
                85                  90                  95

Pro Thr Pro Asp Gly Ala Asp Thr Val Ile Ser Asp Ser Glu Thr Ala
            100                 105                 110

Ala Ala Ser Asn Phe Leu Ala Ser Val Asn Ser Leu Thr Asp Asn Asp
        115                 120                 125

Leu Val Glu Cys Leu Leu Lys Thr Thr Asp Asn Leu Glu Glu Ala Val
    130                 135                 140

Ser Ser Ala Tyr Tyr Ser Glu Ser Leu Glu Gln Pro Val Val Glu Gln
145                 150                 155                 160

Pro Ser Pro Ser Ser Ala Tyr His Ala Glu Ser Phe Glu His Ser Ala
                165                 170                 175

Gly Val Asn Gln Pro Ser Ala Thr Gly Thr Lys Arg Lys Leu Asp Glu
            180                 185                 190

Tyr Leu Asp Asn Ser Gln Gly Val Val Gly Gln Phe Asn Lys Ile Lys
        195                 200                 205

Leu Arg Pro Lys Tyr Lys Lys Ser Thr Ile Gln Ser Cys Ala Thr Leu
    210                 215                 220

Glu Gln Thr Ile Asn His Asn Thr Asn Ile Cys Thr Val Ala Ser Thr
225                 230                 235                 240

Gln Glu Ile Thr His Tyr Phe Thr Asn Asp Phe Ala Pro Tyr Leu Met
                245                 250                 255

Arg Phe Asp Asp Asn Asp Tyr Asn Ser Asn Arg Phe Ser Asp His Met
            260                 265                 270
```

Ser Glu Thr Gly
    275

<210> SEQ ID NO 10
<211> LENGTH: 128
<212> TYPE: DNA
<213> ORGANISM: Autographa californica nucleopolyhedrovirus

<400> SEQUENCE: 10
atcatggaga taattaaaat gataaccatc tcgcaaataa ataagtattt tactgttttc      60
gtaacagttt tgtaataaaa aaacctataa atattccgga ttattcatac cgtcccacca     120
tcgggcgc                                                             128

<210> SEQ ID NO 11
<211> LENGTH: 122
<212> TYPE: DNA
<213> ORGANISM: Autographa californica nucleopolyhedrovirus

<400> SEQUENCE: 11
atacggacct ttaattcaac ccaacacaat atattatagt taaataagaa ttattatcaa      60
atcatttgta tattaattaa aatactatac tgtaaattac attttattta caatcactcg     120
ac                                                                   122

<210> SEQ ID NO 12
<211> LENGTH: 571
<212> TYPE: DNA
<213> ORGANISM: Artificial Sequence
<220> FEATURE:
<223> OTHER INFORMATION: Description of Artificial Sequence: Synthetic
      Recombinant chimeric promoter

<400> SEQUENCE: 12
aaaaacatcg attagggtga ctgaaggtta cattggggta ggttatggtt aatacgtaat      60
ggtttaacac caaaacgata tcatggattt tatataaggt gtaataatat ttttaatgag     120
tggacgcgtc gggtcaatgt cctgcctatt gacgtcataa catattaggt gattatatta     180
aaaatagttt aaactcaaat attacttgca agtttaagtt tcatcataat ctgatcataa     240
gtttcaccca aacagaaacc aaaagcataa ctatcgaata tctttagctt cccatgaaga     300
aagattaccg taaccatcac taggatttta tacgattgta gaaaataaag tattctcagt     360
ctcttttcag agcgctataa aaagggggtgc attctcggta agagtacagt gaactcaca     420 tcgagttaac tccacgctgc agtctcgaga tacggacctt taattcaacc caacacaata     480
tattatagtt aaataagaat tattatcaaa tcatttgtat attaattaaa atactatact     540
gtaaattaca ttttatttac aatcactcga c                                   571

<210> SEQ ID NO 13
<211> LENGTH: 465
<212> TYPE: DNA
<213> ORGANISM: Artificial Sequence
<220> FEATURE:
<223> OTHER INFORMATION: Description of Artificial Sequence: Synthetic
      Recombinant chimeric promoter

<400> SEQUENCE: 13
ggtaccaaat tccgttttgc gacgatgcag agtttttgaa caggctgctc aaacacatag      60
atccgtaccc gctcagtcgg atgtattaca atgcagccaa taccatgttt tacacgacta     120
tggaaaacta tgccgtgtcc aattgcaagt tcaacattga ggattacaat aacatattta     180

```
aggtgatgga aaatattagg aaacacagca acaaaaattc aaacgaccaa gacgagttaa    240
acatatattt gggagttcag tcgtcgaatg caaagcgtaa aaaatattaa taaggtaaaa    300
attacagcta cataaattac acaatttaaa ctgcagtctg gagatacgga cctttaattc    360
aacccaacac aatatattat agttaaataa gaattattat caaatcattt gtatattaat    420
taaaatacta tactgtaaat tacattttat ttacaatcac tcgac                    465

<210> SEQ ID NO 14
<211> LENGTH: 436
<212> TYPE: DNA
<213> ORGANISM: Autographa californica nucleopolyhedrovirus

<400> SEQUENCE: 14
aaaaacatcg attagggtga ctgaaggtta cattggggta ggttatggtt aatacgtaat     60
ggtttaacac caaaacgata tcatggattt tatataaggt gtaataatat ttttaatgag    120
tggacgcgtc gggtcaatgt cctgcctatt gacgtcataa catattaggt gattatatta    180
aaaatagttt aaactcaaat attacttgca gtttaagtt tcatcataat ctgatcataa    240
gtttcaccca aacagaaacc aaaagcataa ctatcgaata tctttagctt cccatgaaga    300
aagattaccg taaccatcac taggatttta tacgattgta gaaaataaag tattctcagt    360
ctcttttcag agcgctataa aaggggtgc attctcggta agagtacagt tgaactcaca    420
tcgagttaac tccacg                                                    436

<210> SEQ ID NO 15
<211> LENGTH: 1176
<212> TYPE: DNA
<213> ORGANISM: Artificial Sequence
<220> FEATURE:
<223> OTHER INFORMATION: Description of Artificial Sequence: Synthetic
      Recombinant chimeric promoter

<400> SEQUENCE: 15
cttgaatgtt agtgaaaccc cctgcgacac aagtattaca ttccttagtg cttgaatcct     60
ttaggaaaga aaagccaatt ttcaaaatct tagcacttgt taactcgcga aaaagaccaa    120
cagatttccc atactacaat tcgacattag aaatgtaaac ccattatcat tatttacgcc    180
tcatttccat ccaataataa gtttaagtac gttgagataa aactggctta cctagaactt    240
gacatggcga cctcttgcac tctgtatctc aagtcaactt tctctatcca aatatttgat    300
aacatttgac atgatattga agtaagattg ttactaaggc ttacattgta atattactga    360
cgcaagttct ttatcaataa aatagctgaa acaaaaaaa aaaacatcga ttagggtgac    420
tgaaggttac attggggtag gttatggtta atacgtaatg gtttaacacc aaaacgatat    480
catggattga ctttataaat tttatataag gtgtaataat attttaatg agtggacgcg    540 tcgggtcaat gtcctgccta ttgacgtcat aacatattag gtgattatat taaaaatact    600
caaatattac ttgcaagttt aagtttcatc ataatctgat cataagtttc acccaaacag    660
aaaccaaaag cataactatc tgctatttga atatctttag cttcccatga agaaagatta    720
ccgtaaccat cactaggatt ttatacgatt gtagaaaata agtattctc agtctctttt    780 cagtttaaaa tctgctggca ttttacaag tcgctgtatc agtcaatgtt tatacaatat    840
gtcaatgtac tttcgtatta atcagaaaaa aatattctac tagttttgat aagctatcac    900
ttttgttaca ttgtactgcc ctttacagtt catcaggtat ttatgaatga catattggag    960
aaacatcgta atcagtccag tataaaaagg ggtgcattct cggtaagagt acagttgaac   1020
```

```
tcacatcgag ttaactccac gctgcagtct cgagatacgg acctttaatt caacccaaca    1080
caatatatta tagttaaata agaattatta tcaaatcatt tgtatattaa ttaaaatact    1140
atactgtaaa ttacatttta tttacaatca ctcgac                              1176
```

<210> SEQ ID NO 16
<211> LENGTH: 250
<212> TYPE: DNA
<213> ORGANISM: Artificial Sequence
<220> FEATURE:
<223> OTHER INFORMATION: Description of Artificial Sequence: Synthetic
      Recombinant chimeric promoter

<400> SEQUENCE: 16

```
atcatggaga taattaaaat gataaccatc tcgcaaataa ataagtattt tactgttttc      60
gtaacagttt tgtaataaaa aaacctataa atattccgga ttattcatac cgtcccacca     120
tcgggcgcat acggaccttt aattcaaccc aacacaatat attatagtta ataagaatt      180 attatcaaat catttgtata ttaattaaaa tactatactg taaattacat tttatttaca    240
atcactcgac                                                            250
```

<210> SEQ ID NO 17
<211> LENGTH: 3163
<212> TYPE: DNA
<213> ORGANISM: Artificial Sequence
<220> FEATURE:
<223> OTHER INFORMATION: Description of Artificial Sequence: Synthetic
      Recombinant expression cassette

<400> SEQUENCE: 17

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag ccttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactt gaggatctgg gaaacgtatg gcgagacgaa     600
gaagttgtta gaggcggttt cgatctcgtt tgattccttg cggctcagca tgatgggcaa     660
agtgaagagg ttcttgtcct ggtacatctc gtacaacttc gacaagagga atccacactt     720
acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
cttgcagttt tgagcggcgg tctcatcgtt gcagacgtcc tgtgagtgtg ggatttcgat     900
gccagtctcc ttaaccaggt tgtagctgat catgaagcgg atcttatcga aggtcacaac     960
gaacacacgg ttgtcaacca tgtagtagtt gtttgtgtac tcgtagacca cgttagagac    1020
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg taggggcga agtcgttgt gaagtagtga gtgatctcct gggtggaagc     1200
```

| | |
|---|---|
| cactgtacag atgttagtgt tgtggttgat ggtttgttcc agtgtagcgc atgactggat | 1260 |
| ggtgctcttc ttgtacttag gtctcaactt gatcttgttg aattgaccca caactccctg | 1320 |
| ggagttatcc aggtactcgt ccaacttcct cttggtgcct gtggccgacg gctggttgac | 1380 |
| accagcagag tgttcgaagg actcggcgtg gtaagctgag ctaggagagg gttgttcgac | 1440 |
| cactggctgt tcgagtgact cgctgtagta ggcagaggac acagcttcct ccaggttgtc | 1500 |
| agtggtcttg agcagacact ccaccaaatc gttgtcagtg agcgagttaa ctgaggcgag | 1560 |
| gaagttgcta gcggcagcgg tttcagagtc ggagatgaca gtatcagctc cgtccggggt | 1620 |
| tgggtggttg tagtaagaca agtaatcgtt aggttgcttg tcgcagaact ccgagtatga | 1680 |
| gttgtcgaag ctagcacgag agggagtgct ggcagaggtg taggaagcgt tgaagttgat | 1740 |
| ttgagtcatg gtgacctggt tgttcacgat cttatcgcca cctgtgtcca cctgcagttg | 1800 |
| ctgggcctca gcgcaggctg aagtggcctc acaggagtag gggctggaag cacagttgga | 1860 |
| agtcatgatg ttttcttgga cgttcaggac gtggctggat gtacggatca tagatctatt | 1920 |
| gggtcatcta gattcgaaag cggccgcgac tagtgagctc gtcgacgtag gcctttgaat | 1980 |
| tccgcgcgct tcggaccggg atccgcgccc gatggtggga cggtatgaat aatccggaat | 2040 |
| atttataggt tttttttatta caaaactgtt acgaaaacag taaaatactt atttatttgc | 2100 |
| gagatggtta tcattttaat tatctccatg atctattaat attccggagt atacatcgat | 2160 |
| gttgacccca caaaagatt tataattaat cataatcacg aacaacaaca agtcaatgaa | 2220 |
| acaaataaac aagttgtcga taaaacattc ataaatgaca cagcaacata caattcttgc | 2280 |
| ataataaaaa tttaaatgac atcatatttg agaataacaa atgacattat ccctcgattg | 2340 |
| tgttttacaa gtagaattct acccgtaaag cgagtttagt tttgaaaaac aaatgacatc | 2400 |
| atttgtataa tgacatcatc ccctgattgt gttttacaag tagaattcta tccgtaaagc | 2460 |
| gagttcagtt ttgaaaacaa atgagtcata cctaaacacg ttaataatct tctgatatca | 2520 |
| gcttatgact caagttatga gccgtgtgca aacatgaga taagtttatg acatcatcca | 2580 |
| ctgatcgtgc gttacaagta gaattctact cgtaaagcca gttcggttat gagccgtgtg | 2640 |
| caaaacatga catcagctta tgactcatac ttgattgtgt tttacgcgta gaattctact | 2700 |
| cgtaaagcga gttcggttat gagccgtgtg caaaacatga catcagctta tgagtcataa | 2760 |
| ttaatcgtgc gttacaagta gaattctact cgtaaagcga gttgaaggat catatttagt | 2820 |
| tgcgtttatg agataagatt gaaagcacgt gtaaaatgtt tcccgcgcgt tggcacaact | 2880 |
| atttacaatg cggccaagtt ataaaagatt ctaatctgat atgttttaaa acacctttgc | 2940 |
| ggcccgagtt gtttgcgtac gtgactagcg aagaagatgt gtggaccgca gaacagatag | 3000 |
| taaaacaaaa ccctagtatt ggagcaataa tcgatgagct catacggacc tttaattcaa | 3060 |
| cccaacacaa tatattatag ttaaataaga attattatca aatcatttgt atattaatta | 3120 |
| aaatactata ctgtaaatta cattttattt acaatcactc gac | 3163 |

<210> SEQ ID NO 18
<211> LENGTH: 3656
<212> TYPE: DNA
<213> ORGANISM: Artificial Sequence
<220> FEATURE:
<223> OTHER INFORMATION: Description of Artificial Sequence: Synthetic
Recombinant expression cassette

<400> SEQUENCE: 18

| | |
|---|---|
| ttagttgaac tcgaacttct tgtacttgca gttgagcttt tgctcggcga atgtgatggc | 60 |

```
gtcggagagt ggcaccagtc cctgcaggat caaggccaag agcttcagca agttgttgtg      120
cagtgtagtt gactcgcgac ggttgacctt gccgatcacg aacatgtggt gcttgaatct      180
gttgtacttt tggatgacct ggctcacatc aacgtccttg atttcgccag agatccagta      240
gaactccttg ttcttcttag cgatggtcag cctttcctcg ttcttgaagg acaaacgat       300 gaagttgtga cccttaacgt tatcgacgtt ttgagtcaag tactgctcaa cgatgtgcat      360
gcttccgtct ccttcttga ccttcttgag gttctcggcg ttgttgttag aagcgatgtt       420
gtcgtggtac ttgtagttgt tgaagagcag gttagcgacg acgagtact tgtatgtcag       480 agtgctcttc ttgttcacga tgaggttcag gttatcaacg acgtacttgt gggagggtt      540 gtccgggaat tggacggact ccgagtactt gaggatctgg gaaacgtatg gcgagacgaa      600
gaagttgtta gaggcggttt cgatctcgtt tgattccttg cggctcagca tgatgggcaa      660
agtgaagagg ttcttgtcct ggtacatctc gtacaacttc gacaagagga atccacactt      720
acgctcgccg agtgattgca gcaaggtcac gaaggttgtc tgagcgtagt acatatcgag      780
gttgaagtag gaggtcagag cggccttgaa tgtgtggtgg acgtccacga agtgacactt      840
cttgcagttt tgagcggcgg tctcatcgtt gcagacgtcc tgtgagtgtg ggatttcgat      900
gccagtctcc ttaaccaggt tgtagctgat catgaagcgg atcttatcga aggtcacaac      960
gaacacacgg ttgtcaacca tgtagtagtt gtttgtgtac tcgtagacca cgttagagac     1020
gtacttggcg aagatgattt cgaaaggctt cacctcggac ttcttaacga cgaacatgta     1080
gtaaccggtt tcagacatgt gatcggagaa tctgttcgag ttgtagtcgt tatcgtcgaa     1140
cctcatcagg taggggcga agtcgttgt gaagtagtga gtgatctcct gggtggaagc      1200
cactgtacag atgttagtgt tgtggttgat ggtttgttcc agtgtagcgc atgactggat     1260
ggtgctcttc ttgtacttag gtctcaactt gatcttgttg aattgaccca caactccctg     1320
ggagttatcc aggtactcgt ccaacttcct cttggtgcct gtggccgacg gctggttgac     1380
accagcagag tgttcgaagg actcggcgtg gtaagctgag ctaggagagg gttgttcgac     1440
cactggctgt tcgagtgact cgctgtagta ggcagaggac acagcttcct ccaggttgtc     1500
agtggtcttg agcagacact ccaccaaatc gttgtcagtg agcgagttaa ctgaggcgag     1560
gaagttgcta gcggcagcgg tttcagagtc ggagatgaca gtatcagctc cgtccgggt     1620 tgggtggtta tagtaagaca agtaatcgtt aggttgcttg tcgcagaact ccgagtatga     1680
gttgtcgaag ctagcacgag agggagtgct ggcagaggtg taggaagcgt tgaagttgat     1740
ttgagtcatg gtgacctggt tgttcacgat cttatcgcca cctgtgtcca cctgcagttg     1800
ctgggcctca gcgcaggctg aagtggcctc acaggagtag gggctggaag cacagttgga     1860
agtcatgatg ttttcttgga cgttcaggac gtggctggat gtacggatca tagatctatt     1920
gggtcatcta gattcgaaag cggccgcgac tagtgagctc gtcgacgtag gccttgaat     1980 tccgcgcgct tcggaccggg atccgcgccc gatggtggga cggtatgaat aatccggaat     2040
atttataggt ttttttatta caaaactgtt acgaaaacag taaatactt atttatttgc      2100 gagatggtta tcattttaat tatctccatg atctattaat attccggagt atacatcgat     2160
gttgacccca acaaaagatt tataattaat cataatcacg acaacaaca agtcaatgaa      2220 acaaataaac aagttgtcga taaaacattc ataatgaca cagcaacata caattcttgc      2280
ataataaaaa tttaaatgac atcatatttg agaataacaa atgacattat ccctcgattg     2340
tgttttacaa gtagaattct acccgtaaag cgagtttagt tttgaaaaac aaatgacatc     2400
atttgtataa tgacatcatc ccctgattgt gttttacaag tagaattcta tccgtaaagc     2460
```

-continued

```
gagttcagtt ttgaaaacaa atgagtcata cctaaacacg ttaataatct tctgatatca    2520
gcttatgact caagttatga gccgtgtgca aacatgaga taagtttatg acatcatcca     2580
ctgatcgtgc gttacaagta gaattctact cgtaaagcca gttcggttat gagccgtgtg    2640
caaaacatga catcagctta tgactcatac ttgattgtgt tttacgcgta gaattctact    2700
cgtaaagcga gttcggttat gagccgtgtg caaaacatga catcagctta tgagtcataa    2760
ttaatcgtgc gttacaagta gaattctact cgtaaagcga gttgaaggat catatttagt    2820
tgcgtttatg agataagatt gaaagcacgt gtaaatgtt tcccgcgcgt tggcacaact     2880
atttacaatg cggccaagtt ataaaagatt ctaatctgat atgttttaaa acacctttgc    2940
ggcccgagtt gtttgcgtac gtgactagcg aagaagatgt gtggaccgca gaacagatag    3000
taaaacaaaa ccctagtatt ggagcaataa tcgatgagct cgtcgacgta ggcctttgaa    3060
ttccgcgcgc ttcggaccgg gatccaaaaa catcgattag ggtgactgaa ggttacattg    3120
gggtaggtta tggttaatac gtaatggttt aacaccaaaa cgatatcatg gattttatat    3180
aaggtgtaat aatattttta atgagtggac gcgtcgggtc aatgtcctgc ctattgacgt    3240
cataacatat taggtgatta tattaaaaat agtttaaact caaatattac ttgcaagttt    3300
aagtttcatc ataatctgat cataagtttc acccaaacag aaaccaaaag cataactatc    3360
gaatatcttt agcttcccat gaagaaagat taccgtaacc atcactagga ttttatacga    3420
ttgtagaaaa taaagtattc tcagtctctt ttcagagcgc tataaaaagg ggtgcattct    3480
cggtaagagt acagttgaac tcacatcgag ttaactccac gctgcagtct cgagatacgg    3540
acctttaatt caacccaaca caatatatta tagttaaata agaattatta tcaaatcatt    3600
tgtatattaa ttaaaatact atactgtaaa ttacatttta tttacaatca ctcgac        3656
```

<210> SEQ ID NO 19
<211> LENGTH: 3541
<212> TYPE: DNA
<213> ORGANISM: Artificial Sequence
<220> FEATURE:
<223> OTHER INFORMATION: Description of Artificial Sequence: Synthetic Recombinant expression cassette

<400> SEQUENCE: 19

```
ttagttgaac tcgaacttct tgtacttgca gttgagcttt tgctcggcga atgtgatggc     60
gtcggagagt ggcaccagtc cctgcaggat caaggccaag agcttcagca agttgttgtg    120
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg cgagacgaa     600 gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
```

```
cttgcagttt tgagcggcgg tctcatcgtt gcagacgtcc tgtgagtgtg ggatttcgat      900
gccagtctcc ttaaccaggt tgtagctgat catgaagcgg atcttatcga aggtcacaac      960
gaacacacgg ttgtcaacca tgtagtagtt gtttgtgtac tcgtagacca cgttagagac     1020
gtacttggcg aagatgattt cgaaaggctt cacctcggac ttcttaacga cgaacatgta     1080
gtaaccggtt tcagacatgt gatcggagaa tctgttcgag ttgtagtcgt tatcgtcgaa     1140
cctcatcagg taggggcga agtcgtttgt gaagtagtga gtgatctcct gggtggaagc     1200
cactgtacag atgttagtgt tgtggttgat ggtttgttcc agtgtagcgc atgactggat     1260
ggtgctcttc ttgtacttag gtctcaactt gatcttgttg aattgaccca caactccctg     1320
ggagttatcc aggtactcgt ccaacttcct cttggtgcct gtggccgacg gctggttgac     1380
accagcagag tgttcgaagg actcggcgtg gtaagctgag ctaggagagg gttgttcgac     1440
cactggctgt tcgagtgact cgctgtagta ggcagaggac acagcttcct ccaggttgtc     1500
agtggtcttg agcagacact ccaccaaatc gttgtcagtg agcgagttaa ctgaggcgag     1560
gaagttgcta gcggcagcgg tttcagagtc ggagatgaca gtatcagctc cgtccgggt     1620
tgggtggtta tagtaagaca agtaatcgtt aggttgcttg tcgcagaact ccgagtatga     1680
gttgtcgaag ctagcacgag agggagtgct ggcagaggtg taggaagcgt tgaagttgat     1740
ttgagtcatg gtgacctggt tgttcacgat cttatcgcca cctgtgtcca cctgcagttg     1800
ctgggcctca gcgcaggctg aagtggcctc acaggagtag gggctggaag cacagttgga     1860
agtcatgatg ttttcttgga cgttcaggac gtggctggat gtacggatca tagatctatc     1920
tagattcgaa agcggccgcg actagtgagc tcgtcgacgt aggcctttga attccgcgcg     1980
cttcggaccg ggatccgcgc ccgatggtgg gacggtatga ataatccgga atatttatag     2040
gttttttat tacaaaactg ttacgaaaac agtaaaatac ttatttattt gcgagatggt     2100
tatcatttta attatctcca tgatctatta atattccgga gtatacatcg atgttgaccc     2160
caacaaaaga tttataatta atcataatca cgaacaacaa caagtcaatg aaacaaataa     2220
acaagttgtc gataaaacat tcataaatga cacagcaaca tacaattctt gcataataaa     2280
aatttaaatg acatcatatt tgagaataac aaatgacatt atccctcgat tgtgttttac     2340
aagtagaatt ctacccgtaa agcgagttta gttttgaaaa acaaatgaca tcatttgtat     2400
aatgacatca tcccctgatt gtgttttaca agtagaattc tatccgtaaa gcgagttcag     2460
ttttgaaaac aaatgagtca tacctaaaca cgttaataat cttctgatat cagcttatga     2520
ctcaagttat gagccgtgtg caaaacatga gataagttta tgacatcatc cactgatcgt     2580
gcgttacaag tagaattcta ctcgtaaagc cagttcggtt atgagccgtg tgcaaaacat     2640
gacatcagct tatgactcat acttgattgt gttttacgcg tagaattcta ctcgtaaagc     2700
gagttcggtt atgagccgtg tgcaaaacat gacatcagct tatgagtcat aattaatcgt     2760
gcgttacaag tagaattcta ctcgtaaagc gagttgaagg atcatattta gttgcgttta     2820
tgagataaga ttgaaagcac gtgtaaaatg tttcccgcgc gttggcacaa ctatttacaa     2880
tgcggccaag ttataaaaga ttctaatctg atatgtttta aaacaccttt gcggcccgag     2940
ttgtttgcgt acgtgactag cgaagaagat gtgtggaccg cagaacagat agtaaaacaa     3000
aaccctagta ttggagcaat aatcgatgag ctcgtcgacg taggcctttg aattccgcgc     3060
gcttcggacc gggatcggta ccaaattccg ttttgcgacg atgcagagtt tttgaacagg     3120
ctgctcaaac acatagatcc gtacccgctc agtcggatgt attacaatgc agccaatacc     3180
```

-continued

| | |
|---|---|
| atgtttttaca cgactatgga aaactatgcc gtgtccaatt gcaagttcaa cattgaggat | 3240 |
| tacaataaca tatttaaggt gatggaaaat attaggaaac acagcaacaa aaattcaaac | 3300 |
| gaccaagacg agttaaacat atatttggga gttcagtcgt cgaatgcaaa gcgtaaaaaa | 3360 |
| tattaataag gtaaaaatta cagctacata aattacacaa tttaaactgc agtctggaga | 3420 |
| tacggacctt taattcaacc caacacaata tattatagtt aaataagaat tattatcaaa | 3480 |
| tcatttgtat attaattaaa atactatact gtaaattaca ttttatttac aatcactcga | 3540 |
| c | 3541 |

<210> SEQ ID NO 20
<211> LENGTH: 3512
<212> TYPE: DNA
<213> ORGANISM: Artificial Sequence
<220> FEATURE:
<223> OTHER INFORMATION: Description of Artificial Sequence: Synthetic
      Recombinant expression cassette

<400> SEQUENCE: 20

| | |
|---|---|
| ttagttgaac tcgaacttct tgtacttgca gttgagcttt tgctcggcga atgtgatggc | 60 |
| gtcggagagt ggcaccagtc cctgcaggat caaggccaag agcttcagca agttgttgtg | 120 |
| cagtgtagtt gactcgcgac ggttgacctt gccgatcacg aacatgtggt gcttgaatct | 180 |
| gttgtacttt tggatgacct ggctcacatc aacgtccttg atttcgccag agatccagta | 240 |
| gaactccttg ttcttcttag cgatggtcag cctttcctcg ttcttgaagg acaacacgat | 300 |
| gaagttgtga cccttaacgt tatcgacgtt ttgagtcaag tactgctcaa cgatgtgcat | 360 |
| gcttccgtct tccttcttga ccttcttgag gttctcggcg ttgttgttag aagcgatgtt | 420 |
| gtcgtggtac ttgtagttgt tgaagagcag gttagcgacg gacgagtact tgtatgtcag | 480 |
| agtgctcttc ttgttcacga tgaggttcag gttatcaacg acgtacttgt tgggagggtt | 540 |
| gtccgggaat tggacggact ccgagtactt gaggatctgg gaaacgtatg gcagacgaa | 600 |
| gaagttgtta gaggcggttt cgatctcgtt tgattccttg cggctcagca tgatgggcaa | 660 |
| agtgaagagg ttcttgtcct ggtacatctc gtacaacttc gacaagagga atccacactt | 720 |
| acgctcgccg agtgattgca gcaaggtcac gaaggttgtc tgagcgtagt acatatcgag | 780 |
| gttgaagtag gaggtcagag cggccttgaa tgtgtggtgg acgtccacga agtgacactt | 840 |
| cttgcagttt tgagcggcgg tctcatcgtt gcagacgtcc tgtgagtgtg ggatttcgat | 900 |
| gccagtctcc ttaaccaggt tgtagctgat catgaagcgg atcttatcga aggtcacaac | 960 |
| gaacacacgg ttgtcaacca tgtagtagtt gtttgtgtac tcgtagacca cgttagagac | 1020 |
| gtacttggcg aagatgattt cgaaaggctt cacctcggac ttcttaacga cgaacatgta | 1080 |
| gtaaccggtt tcagacatgt gatcggagaa tctgttcgag ttgtagtcgt tatcgtcgaa | 1140 |
| cctcatcagg taggggcga agtcgtttgt gaagtagtga gtgatctcct gggtggaagc | 1200 |
| cactgtacag atgttagtgt tgtggttgat ggttgttcc agtgtagcgc atgactggat | 1260 |
| ggtgctcttc ttgtacttag gtctcaactt gatcttgttg aattgaccca caactccctg | 1320 |
| ggagttatcc aggtactcgt ccaacttcct cttggtgcct gtggccgacg gctggttgac | 1380 |
| accagcagag tgttcgaagg actcggcgtg gtaagctgag ctaggagagg gttgttcgac | 1440 |
| cactggctgt tcgagtgact cgctgtagta ggcagaggac acagcttcct ccaggttgtc | 1500 |
| agtggtcttg agcagacact ccaccaaatc gttgtcagtg agcgagttaa ctgaggcgag | 1560 |
| gaagttgcta gcggcagcgg tttcagagtc ggagatgaca gtatcagctc cgtccgggt | 1620 |

```
tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatc    1920
tagatgcatt cgcgaggtac cgagctcgaa ttcactggcc gtcgttttac aacgtcgtga    1980
ctgggaaaac cctggcgtta cccaacttaa tcgccttgca gcacatcccc ctttcgccag    2040
ctgctagcac catggctcga gcgtggagtt aactcgatgt gagttcaact gtactcttac    2100
cgagaatgca ccccttttta tagcgctctg aaaagagact gagaatactt tattttctac    2160
aatcgtataa aatcctagtg atggttacgg taatctttct tcatgggaag ctaaagatat    2220
tcgatagtta tgcttttggt ttctgtttgg gtgaaactta tgatcagatt atgatgaaac    2280
ttaaacttgc aagtaatatt tgagtttaaa ctatttttaa tataatcacc taatatgtta    2340
tgacgtcaat aggcaggaca ttgacccgac gcgtccactc attaaaaata ttattacacc    2400
ttatataaaa tccatgatat cgttttggtg ttaaaccatt acgtattaac cataacctac    2460
cccaatgtaa ccttcagtca ccctaatcga tgttttgta tacatcgatg ttgaccccaa    2520
caaaagattt ataattaatc ataatcacga acaacaacaa gtcaatgaaa caaataaaca    2580
agttgtcgat aaaacattca taaatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaaatgttt cccgcgcgtt ggcacaacta tttacaatgc    3240
ggccaagtta taaagattc taatctgata tgttttaaaa cacctttgcg gcccgagttg    3300
tttgcgtacg tgactagcga agaagatgtg tggaccgcag aacagatagt aaaacaaaac    3360
cctagtattg gagcaataat cgatgagctc atacggacct taattcaac ccaacacaat    3420 atattatagt taaataagaa ttattatcaa atcatttgta tattaattaa aatactatac    3480
tgtaaattac attttatta caatcactcg ac                                   3512
```

<210> SEQ ID NO 21
<211> LENGTH: 4005
<212> TYPE: DNA
<213> ORGANISM: Artificial Sequence
<220> FEATURE:
<223> OTHER INFORMATION: Description of Artificial Sequence: Synthetic
      Recombinant expression cassette

<400> SEQUENCE: 21

```
ttagttgaac tcgaacttct tgtacttgca gttgagcttt tgctcggcga atgtgatggc     60
gtcggagagt ggcaccagtc cctgcaggat caaggccaag agcttcagca agttgttgtg    120
```

```
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga cctccttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcagacgaa     600 gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg gttgttcgac   1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccggggt   1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatc   1920
tagatgcatt cgcgaggtac cgagctcgaa ttcactggcc gtcgttttac aacgtcgtga   1980
ctgggaaaac cctggcgtta cccaacttaa tcgccttgca gcacatcccc ctttcgccag   2040
ctgctagcac catggctcga gcgtggagtt aactcgatgt gagttcaact gtactcttac   2100
cgagaatgca ccccttttta tagcgctctg aaaagagact gagaatactt tattttctac   2160
aatcgtataa aatcctagtg atggttacgg taatctttct tcatgggaag ctaaagatat   2220
tcgatagtta tgcttttggt ttctgttttgg gtgaaactta tgatcagatt atgatgaaac   2280
ttaaacttgc aagtaatatt tgagtttaaa ctattttaa tataatcacc taatatgtta   2340
tgacgtcaat aggcaggaca ttgacccgac gcgtccactc attaaaaata ttattacacc   2400
ttatataaaa tccatgatat cgttttggtg ttaaaccatt acgtattaac cataacctac   2460
cccaatgtaa ccttcagtca ccctaatcga tgtttttgta tacatcgatg ttgaccccaa   2520
```

```
caaaagattt ataattaatc ataatcacga caacaacaa gtcaatgaaa caaataaaca    2580
agttgtcgat aaaacattca taaatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaaatgttt cccgcgcgtt ggcacaacta tttacaatgc    3240
ggccaagtta taaaagattc taatctgata tgttttaaaa cacctttgcg gcccgagttg    3300
tttgcgtacg tgactagcga agaagatgtg tggaccgcag aacagatagt aaaacaaaac    3360
cctagtattg gagcaataat cgatgagctc gtcgacgtag gcctttgaat tccgcgcgct    3420
tcggaccggg atccaaaaac atcgattagg gtgactgaag gttacattgg ggtaggttat    3480
ggttaatacg taatggttta acaccaaaac gatatcatgg attttatata aggtgtaata    3540
atatttttaa tgagtggacg cgtcgggtca atgtcctgcc tattgacgtc ataacatatt    3600
aggtgattat attaaaaata gtttaaactc aaatattact gcaagtttta gtttcatca    3660 taatctgatc ataagtttca cccaaacaga aaccaaaagc ataactatcg aatatcttta    3720
gcttcccatg aagaaagatt accgtaacca tcactaggat tttatacgat tgtagaaaat    3780
aaagtattct cagtctcttt tcagagcgct ataaaaaggg gtgcattctc ggtaagagta    3840
cagttgaact cacatcgagt taactccacg ctgcagtctc gagatacgga cctttaattc    3900
aacccaacac aatatattat agttaaataa gaattattat caaatcattt gtatattaat    3960
taaaatacta tactgtaaat tacattttat ttacaatcac tcgac                  4005
```

<210> SEQ ID NO 22  
<211> LENGTH: 3898  
<212> TYPE: DNA  
<213> ORGANISM: Artificial Sequence  
<220> FEATURE:  
<223> OTHER INFORMATION: Description of Artificial Sequence: Synthetic Recombinant expression cassette

<400> SEQUENCE: 22

```
ttagttgaac tcgaacttct gtacttgca gttgagcttt tgctcggcga atgtgatggc      60
gtcggagagt ggcaccagtc cctgcaggat caaggccaag agcttcagca agttgttgtg    120
cagtgtagtt gactcgcgac ggttgacctt gccgatcacg acatgtggt gcttgaatct    180 gttgtactt tggatgacct ggctcacatc aacgtccttg atttcgccag agatccagta    240
gaactccttg ttcttcttag cgatggtcag ccttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
```

-continued

```
gtccgggaat tggacggact ccgagtactt gaggatctgg gaaacgtatg gcgagacgaa      600
gaagttgtta gaggcggttt cgatctcgtt tgattccttg cggctcagca tgatgggcaa      660
agtgaagagg ttcttgtcct ggtacatctc gtacaacttc gacaagagga atccacactt      720
acgctcgccg agtgattgca gcaaggtcac gaaggttgtc tgagcgtagt acatatcgag      780
gttgaagtag gaggtcagag cggccttgaa tgtgtggtgg acgtccacga agtgacactt      840
cttgcagttt tgagcggcgg tctcatcgtt gcagacgtcc tgtgagtgtg ggatttcgat      900
gccagtctcc ttaaccaggt tgtagctgat catgaagcgg atcttatcga aggtcacaac      960
gaacacacgg ttgtcaacca tgtagtagtt gttttgtgtac tcgtagacca cgttagagac     1020
gtacttggcg aagatgattt cgaaaggctt cacctcggac ttcttaacga cgaacatgta     1080
gtaaccggtt tcagacatgt gatcggagaa tctgttcgag ttgtagtcgt tatcgtcgaa     1140
cctcatcagg taggggcga agtcgtttgt gaagtagtga gtgatctcct gggtggaagc      1200
cactgtacag atgttagtgt tgtggttgat ggtttgttcc agtgtagcgc atgactggat     1260
ggtgctcttc ttgtacttag gtctcaactt gatcttgttg aattgaccca caactccctg     1320
ggagttatcc aggtactcgt ccaacttcct cttggtgcct gtggccgacg gctggttgac     1380
accagcagag tgttcgaagg actcggcgtg gtaagctgag ctaggagagg ttgttcgac      1440 cactggctgt tcgagtgact cgctgtagta ggcagaggac acagcttcct ccaggttgtc     1500
agtggtcttg agcagacact ccaccaaatc gttgtcagtg agcgagttaa ctgaggcgag     1560
gaagttgcta gcggcagcgg tttcagagtc ggagatgaca gtatcagctc cgtccgggt      1620 tgggtggttg tagtaagaca agtaatcgtt aggttgcttg tcgcagaact ccgagtatga     1680
gttgtcgaag ctagcacgag agggagtgct ggcagaggtg taggaagcgt tgaagttgat     1740
ttgagtcatg gtgacctggt tgttcacgat cttatcgcca cctgtgtcca cctgcagttg     1800
ctgggcctca gcgcaggctg aagtggcctc acaggagtag gggctggaag cacagttgga     1860
agtcatgatg ttttcttgga cgttcaggac gtggctggat gtacggatca tagatctatc     1920
tagatgcatt cgcgaggtac cgagctcgaa ttcactggcc gtcgttttac aacgtcgtga     1980
ctgggaaaac cctggcgtta cccaacttaa tcgccttgca gcacatcccc ctttcgccag     2040
ctgctagcac catggctcga gcgtggagtt aactcgatgt gagttcaact gtactcttac     2100
cgagaatgca ccccttttta tagcgctctg aaaagagact gagaatactt tattttctac     2160
aatcgtataa aatcctagtg atggttacgg taatctttct tcatgggaag ctaaagatat     2220
tcgatagtta tgcttttggt ttctgtttgg gtgaaactta tgatcagatt atgatgaaac     2280
ttaaacttgc aagtaatatt tgagtttaaa ctatttttaa tataatcacc taatatgtta     2340
tgacgtcaat aggcaggaca ttgacccgac gcgtccactc attaaaaata ttattacacc     2400
ttatataaaa tccatgatat cgttttggtg ttaaaccatt acgtattaac cataacctac     2460
cccaatgtaa ccttcagtca ccctaatcga tgtttttgta tacatcgatg ttgaccccaa     2520
caaaagattt ataattaatc ataatcacga acaacaacaa gtcaatgaaa caaataaaca     2580
agttgtcgat aaaacattca taatgacac agcaacatac aattcttgca taataaaaat      2640
ttaaatgaca tcatatttga gaataacaaa tgacattatc cctcgattgt gttttacaag     2700
tagaattcta cccgtaaagc gagtttagtt ttgaaaaaca aatgacatca tttgtataat     2760
gacatcatcc cctgattgtg ttttacaagt agaattctat ccgtaaagcg agttcagttt     2820
tgaaaacaaa tgagtcatac ctaaacacgt taataatctt ctgatatcag cttatgactc     2880
```

```
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaaatgttt cccgcgcgtt ggcacaacta tttacaatgc    3240
ggccaagtta taaaagattc taatctgata tgttttaaaa cacctttgcg gcccgagttg    3300
tttgcgtacg tgactagcga agaagatgtg tggaccgcag aacagatagt aaaacaaaac    3360
cctagtattg gagcaataat cgatgagctc gtcgacgtag gcctttgaat tccgcgcgct    3420
tcggaccggg atcggtacca aattccgttt tgcgacgatg cagagttttt gaacaggctg    3480
ctcaaacaca tagatccgta cccgctcagt cggatgtatt acaatgcagc aataccatg    3540 ttttacacga ctatggaaaa ctatgccgtg tccaattgca agttcaacat tgaggattac    3600
aataacatat ttaaggtgat ggaaaatatt aggaaacaca gcaacaaaaa ttcaaacgac    3660
caagacgagt taaacatata tttgggagtt cagtcgtcga atgcaaagcg taaaaaatat    3720
taataaggta aaaattacag ctacataaat tacacaattt aaactgcagt ctggagatac    3780
ggacctttaa ttcaacccaa cacaatatat tatagttaaa taagaattat tatcaaatca    3840
tttgtatatt aattaaaata ctatactgta aattacattt tatttacaat cactcgac     3898
```

<210> SEQ ID NO 23
<211> LENGTH: 3179
<212> TYPE: DNA
<213> ORGANISM: Artificial Sequence
<220> FEATURE:
<223> OTHER INFORMATION: Description of Artificial Sequence: Synthetic
      Recombinant expression cassette

<400> SEQUENCE: 23

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg acgagtact tgtatgtcag      480 agtgctcttc ttgttcacga tgaggttcag gttatcaacg acgtacttgt tgggagggtt     540
gtccgggaat tggacggact ccgagtactt gaggatctgg gaaacgtatg gcgagacgaa     600
gaagttgtta gaggcggttt cgatctcgtt tgattccttg cggctcagca tgatgggcaa     660
agtgaagagg ttcttgtcct ggtacatctc gtacaacttc gacaagagga atccacactt     720
acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
cttgcagttt tgagcggcgg tctcatcgtt gcagacgtcc tgtgagtgtg ggatttcgat     900
gccagtctcc ttaaccaggt tgtagctgat catgaagcgg atcttatcga aggtcacaac     960
gaacacacgg ttgtcaacca tgtagtagtt gtttgtgtac tcgtagacca cgttagagac    1020
```

```
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg tagggggcga agtcgtttgt gaagtagtga gtgatctcct gggtggaagc    1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg gtaagctgag ctaggagagg ttgttcgac     1440
cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcgcagcgg tttcagagtc ggagatgaca gtatcagctc cgtccgggt     1620
tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatt    1920
gggtcatcta gattcgaaag cggccgcgac tagtgagctc gtcgacgtag gcctttgaat    1980
tccgcgcgct tcggaccggg atccgcgccc gatggtggga cggtatgaat aatccggaat    2040
atttataggt tttttttatta caaaactgtt acgaaaacag taaaatactt atttatttgc    2100
gagatggtta tcattttaat tatctccatg atctattaat attccggagt atacatcgat    2160
gttgaccca acaaaagatt tataattaat cataatcacg aacaacaaca agtcaatgaa    2220
acaaataaac aagttgtcga taaaacattc ataaatgaca cagcaacata caattcttgc    2280
ataataaaaa tttaaatgac atcatatttg agaataacaa atgacattat ccctcgattg    2340
tgttttacaa gtagaattct acccgtaaag cgagtttagt tttgaaaaac aaatgacatc    2400
atttgtataa tgacatcatc ccctgattgt gttttacaag tagaattcta tccgtaaagc    2460
gagttcagtt ttgaaaacaa atgagtcata cctaaacacg ttaataatct tctgatatca    2520
gcttatgact caagttatga gccgtgtgca aaacatgaga taagtttatg acatcatcca    2580
ctgatcgtgc gttacaagta gaattctact cgtaaagcca gttcggttat gagccgtgtg    2640
caaaacatga catcagctta tgactcatac ttgattgtgt tttacgcgta gaattctact    2700
cgtaaagcga gttcggttat gagccgtgtg caaaacatga catcagctta tgagtcataa    2760
ttaatcgtgc gttacaagta gaattctact cgtaaagcga gttgaaggat catatttagt    2820
tgcgtttatg agataagatt gaaagcacgt gtaaatgtt  tcccgcgcgt tggcacaact    2880
atttacaatg cggccaagtt ataaaagatt ctaatctgat atgttttaaa acacctttgc    2940
ggcccgagtt gtttgcgtac gtgactagcg aagaagatgt gtggaccgca gaacagatag    3000
taaaacaaaa ccctagtatt ggagcaataa tcgattccgg aatattaata gatcatggag    3060
ataattaaaa tgataaccat ctcgcaaata aataagtatt ttactgtttt cgtaacagtt    3120
ttgtaataaa aaaacctata aatattccgg attattcata ccgtcccacc atcgggcgc     3179
```

<210> SEQ ID NO 24
<211> LENGTH: 3528
<212> TYPE: DNA
<213> ORGANISM: Artificial Sequence
<220> FEATURE:
<223> OTHER INFORMATION: Description of Artificial Sequence: Synthetic Recombinant expression cassette

<400> SEQUENCE: 24

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactt gaggatctgg aaacgtatg gcgagacgaa      600
gaagttgtta gaggcggttt cgatctcgtt tgattccttg cggctcagca tgatgggcaa     660
agtgaagagg ttcttgtcct ggtacatctc gtacaacttc gacaagagga atccacactt     720
acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
cttgcagttt tgagcggcgg tctcatcgtt gcagacgtcc tgtgagtgtg ggatttcgat     900
gccagtctcc ttaaccaggt tgtagctgat catgaagcgg atcttatcga aggtcacaac     960
gaacacacgg ttgtcaacca tgtagtagtt gtttgtgtac tcgtagacca cgttagagac    1020
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg tagggggcga agtcgtttgt gaagtagtga gtgatctcct gggtggaagc    1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg gtaagctgag ctaggagagg ttgttcgac     1440
cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccgggt     1620
tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatc    1920
tagatgcatt cgcgaggtac cgagctcgaa ttcactggcc gtcgttttac aacgtcgtga    1980
ctgggaaaac cctggcgtta cccaacttaa tcgccttgca gcacatcccc ctttcgccag    2040
ctgctagcac catggctcga gcgtggagtt aactcgatgt gagttcaact gtactcttac    2100
cgagaatgca ccccttttta tagcgctctg aaaagagact gagaatactt tattttctac    2160
aatcgtataa aatcctagtg atggttacgg taatctttct tcatgggaag ctaaagatat    2220
tcgatagtta tgcttttggt ttctgtttgg gtgaaactta tgatcagatt atgatgaaac    2280
```

```
ttaaacttgc aagtaatatt tgagtttaaa ctatttttaa tataatcacc taatatgtta    2340
tgacgtcaat aggcaggaca ttgacccgac gcgtccactc attaaaaata ttattacacc    2400
ttatataaaa tccatgatat cgttttggtg ttaaaccatt acgtattaac cataacctac    2460
cccaatgtaa ccttcagtca ccctaatcga tgttttgta tacatcgatg ttgaccccaa     2520
caaaagattt ataattaatc ataatcacga acaacaacaa gtcaatgaaa caaataaaca    2580
agttgtcgat aaaacattca taatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg     2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaaatgttt cccgcgcgtt ggcacaacta tttacaatgc    3240
ggccaagtta taaaagattc taatctgata tgttttaaaa cacctttgcg gcccgagttg    3300
tttgcgtacg tgactagcga agaagatgtg tggaccgcag aacagatagt aaaacaaaac    3360
cctagtattg gagcaataat cgattccgga atattaatag atcatggaga taattaaaat    3420
gataaccatc tcgcaaataa ataagtattt tactgttttc gtaacagttt tgtaataaaa    3480
aaacctataa atattccgga ttattcatac cgtcccacca tcgggcgc                 3528
```

<210> SEQ ID NO 25
<211> LENGTH: 3291
<212> TYPE: DNA
<213> ORGANISM: Artificial Sequence
<220> FEATURE:
<223> OTHER INFORMATION: Description of Artificial Sequence: Synthetic Recombinant expression cassette

<400> SEQUENCE: 25

```
ttagttgaac tcgaacttct tgtacttgca gttgagcttt tgctcggcga atgtgatggc    60
gtcggagagt ggcaccagtc cctgcaggat caaggccaag agcttcagca agttgttgtg    120
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg acgagtact tgtatgtcag     480 agtgctcttc ttgttcacga tgaggttcag gttatcaacg acgtacttgt tgggagggtt    540
gtccgggaat tggacggact ccgagtactt gaggatctgg gaaacgtatg cgagacgaa     600 gaagttgtta gaggcggttt cgatctcgtt tgattccttg cggctcagca tgatgggcaa    660
agtgaagagg ttcttgtcct ggtacatctc gtacaacttc acaagagga atccacactt    720 acgctcgccg agtgattgca gcaaggtcac gaaggttgtc tgagcgtagt acatatcgag    780
```

```
gttgaagtag gaggtcagag cggccttgaa tgtgtggtgg acgtccacga agtgacactt      840
cttgcagttt tgagcggcgg tctcatcgtt gcagacgtcc tgtgagtgtg ggatttcgat      900
gccagtctcc ttaaccaggt tgtagctgat catgaagcgg atcttatcga aggtcacaac      960
gaacacacgg ttgtcaacca tgtagtagtt gtttgtgtac tcgtagacca cgttagagac     1020
gtacttggcg aagatgattt cgaaaggctt cacctcggac ttcttaacga cgaacatgta     1080
gtaaccggtt tcagacatgt gatcggagaa tctgttcgag ttgtagtcgt tatcgtcgaa     1140
cctcatcagg tagggggcga agtcgtttgt gaagtagtga gtgatctcct gggtggaagc     1200
cactgtacag atgttagtgt tgtggttgat ggtttgttcc agtgtagcgc atgactggat     1260
ggtgctcttc ttgtacttag gtctcaactt gatcttgttg aattgaccca caactccctg     1320
ggagttatcc aggtactcgt ccaacttcct cttggtgcct gtggccgacg gctggttgac     1380
accagcagag tgttcgaagg actcggcgtg gtaagctgag ctaggagagg ttgttcgac      1440 cactggctgt tcgagtgact cgctgtagta ggcagaggac acagcttcct ccaggttgtc     1500
agtggtcttg agcagacact ccaccaaatc gttgtcagtg agcgagttaa ctgaggcgag     1560
gaagttgcta gcggcagcgg tttcagagtc ggagatgaca gtatcagctc cgtccgggt      1620 tgggtggttg tagtaagaca agtaatcgtt aggttgcttg tcgcagaact ccgagtatga     1680
gttgtcgaag ctagcacgag agggagtgct ggcagaggtg taggaagcgt tgaagttgat     1740
ttgagtcatg gtgacctggt tgttcacgat cttatcgcca cctgtgtcca cctgcagttg     1800
ctgggcctca gcgcaggctg aagtggcctc acaggagtag gggctggaag cacagttgga     1860
agtcatgatg ttttcttgga cgttcaggac gtggctggat gtacggatca tagatctatt     1920
gggtcatcta gattcgaaag cggccgcgac tagtgagctc gtcgacgtag gcctttgaat     1980
tccgcgcgct tcggaccggg atccgcgccc gatggtggga cggtatgaat aatccggaat     2040
atttataggt ttttttatta caaaactgtt acgaaaacag taaaatactt atttatttgc     2100
gagatggtta tcattttaat tatctccatg atctattaat attccggagt atacatcgat     2160
gttgacccca acaaaagatt tataattaat cataatcacg aacaacaaca agtcaatgaa     2220
acaaataaac aagttgtcga taaaacattc ataaatgaca cagcaacata caattcttgc     2280
ataataaaaa tttaaatgac atcatatttg agaataacaa atgacattat ccctcgattg     2340
tgttttacaa gtagaattct acccgtaaag cgagtttagt tttgaaaaac aaatgacatc     2400
atttgtataa tgacatcatc ccctgattgt gttttacaag tagaattcta tccgtaaagc     2460
gagttcagtt ttgaaaacaa atgagtcata cctaaacacg ttaataatct tctgatatca     2520
gcttatgact caagttatga gccgtgtgca aaacatgaga taagtttatg acatcatcca     2580
ctgatcgtgc gttacaagta gaattctact cgtaaagcca gttcggttat gagccgtgtg     2640
caaaacatga catcagctta tgactcatac ttgattgtgt tttacgcgta gaattctact     2700
cgtaaagcga gttcggttat gagccgtgtg caaaacatga catcagctta tgagtcataa     2760
ttaatcgtgc gttacaagta gaattctact cgtaaagcga gttgaaggat catatttagt     2820
tgcgtttatg agataagatt gaaagcacgt gtaaatgtt tcccgcgcgt tggcacaact      2880
atttacaatg cggccaagtt ataaaagatt ctaatctgat atgtttaaa acacctttgc      2940 ggcccgagtt gtttgcgtac gtgactagcg aagaagatgt gtggaccgca gaacagatag     3000
taaaacaaaa ccctagtatt ggagcaataa tcgatgagct catcatggag ataattaaaa     3060
tgataaccat ctcgcaaata aataagtatt ttactgtttt cgtaacagtt ttgtaataaa     3120
```

```
aaaacctata aatattccgg attattcata ccgtcccacc atcgggcgca tacggacctt    3180
taattcaacc caacacaata tattatagtt aaataagaat tattatcaaa tcatttgtat    3240
attaattaaa atactatact gtaaattaca ttttatttac aatcactcga c             3291
```

<210> SEQ ID NO 26
<211> LENGTH: 3640
<212> TYPE: DNA
<213> ORGANISM: Artificial Sequence
<220> FEATURE:
<223> OTHER INFORMATION: Description of Artificial Sequence: Synthetic
      Recombinant expression cassette

<400> SEQUENCE: 26

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactt gaggatctgg gaaacgtatg gcagacgaa      600 gaagttgtta gaggcggttt cgatctcgtt tgattccttg cggctcagca tgatgggcaa     660
agtgaagagg ttcttgtcct ggtacatctc gtacaacttc gacaagagga atccacactt     720
acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
cttgcagttt tgagcggcgg tctcatcgtt gcagacgtcc tgtgagtgtg ggatttcgat     900
gccagtctcc ttaaccaggt tgtagctgat catgaagcgg atcttatcga aggtcacaac     960
gaacacacgg ttgtcaacca tgtagtagtt gtttgtgtac tcgtagacca cgttagagac    1020
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg taggggcga agtcgtttgt gaagtagtga gtgatctcct gggtggaagc    1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg gtaagctgag ctaggagagg ttgttcgac     1440 cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccgggt     1620 tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
```

```
agtcatgatg tttctcttgga cgttcaggac gtggctggat gtacggatca tagatctatc   1920
tagatgcatt cgcgaggtac cgagctcgaa ttcactggcc gtcgttttac aacgtcgtga   1980
ctgggaaaac cctggcgtta cccaacttaa tcgccttgca gcacatcccc ctttcgccag   2040
ctgctagcac catggctcga gcgtggagtt aactcgatgt gagttcaact gtactcttac   2100
cgagaatgca cccctttta tagcgctctg aaaagagact gagaatactt tattttctac   2160
aatcgtataa atcctagtg atggttacgg taatctttct tcatgggaag ctaaagatat   2220
tcgatagtta tgcttttggt ttctgtttgg gtgaaactta tgatcagatt atgatgaaac   2280
ttaaacttgc aagtaatatt tgagtttaaa ctattttaa tataatcacc taatatgtta   2340
tgacgtcaat aggcaggaca ttgacccgac gcgtccactc attaaaaata ttattacacc   2400
ttatataaaa tccatgatat cgttttggtg ttaaaccatt acgtattaac cataacctac   2460
cccaatgtaa ccttcagtca ccctaatcga tgttttgta tacatcgatg ttgaccccaa   2520
caaaagattt ataattaatc ataatcacga acaacaacaa gtcaatgaaa caaataaaca   2580
agttgtcgat aaaacattca taaatgacac agcaacatac aattcttgca taataaaaat   2640
ttaaatgaca tcatatttga gaataacaaa tgacattatc cctcgattgt gttttacaag   2700
tagaattcta cccgtaaagc gagtttagtt ttgaaaaaca aatgacatca tttgtataat   2760
gacatcatcc cctgattgtg ttttacaagt agaattctat ccgtaaagcg agttcagttt   2820
tgaaaacaaa tgagtcatac ctaaacacgt taataatctt ctgatatcag cttatgactc   2880
aagttatgag ccgtgtgcaa acatgagat aagtttatga catcatccac tgatcgtgcg   2940
ttacaagtag aattctactc gtaaagccag ttcggttatg agccgtgtgc aaaacatgac   3000
atcagcttat gactcatact tgattgtgtt ttacgcgtag aattctactc gtaaagcgag   3060
ttcggttatg agccgtgtgc aaaacatgac atcagcttat gagtcataat taatcgtgcg   3120
ttacaagtag aattctactc gtaaagcgag ttgaaggatc atatttagtt gcgtttatga   3180
gataagattg aaagcacgtg taaaatgttt cccgcgcgtt ggcacaacta tttacaatgc   3240
ggccaagtta taaagattc taatctgata tgttttaaaa caccttcgcg gcccgagttg   3300
tttgcgtacg tgactagcga agaagatgtg tggaccgcag aacagatagt aaaacaaaac   3360
cctagtattg gagcaataat cgatgagctc atcatggaga taattaaaat gataaccatc   3420
tcgcaaataa ataagtattt tactgttttc gtaacagttt tgtaataaaa aaacctataa   3480
atattccgga ttattcatac cgtcccacca tcgggcgcat acggaccttt aattcaaccc   3540
aacacaatat attatagtta aataagaatt attatcaaat catttgtata ttaattaaaa   3600
tactatactg taaattacat tttatttaca atcactcgac                         3640
```

<210> SEQ ID NO 27
<211> LENGTH: 881
<212> TYPE: DNA
<213> ORGANISM: Autographa californica nucleopolyhedrovirus

<400> SEQUENCE: 27

```
atcgatgttg accccaacaa aagatttata attaatcata atcacgaaca acaacaagtc    60
aatgaaacaa ataaacaagt tgtcgataaa acattcataa atgacacagc aacatacaat   120
tcttgcataa taaaaattta atgacatca tatttgagaa taacaaatga cattatccct   180
cgattgtgtt ttacaagtag aattctaccc gtaaagcgag tttagttttg aaaacaaat   240 gacatcattt gtaatgacac atcatcccct gattgtgttt tacaagtaga attctatccg   300
taaagcgagt tcagttttga aaacaaatga gtcataccta aacacgttaa taatcttctg   360
```

```
atatcagctt atgactcaag ttatgagccg tgtgcaaaac atgagataag tttatgacat      420
catccactga tcgtgcgtta caagtagaat tctactcgta aagccagttc ggttatgagc      480
cgtgtgcaaa acatgacatc agcttatgac tcatacttga ttgtgtttta cgcgtagaat      540
tctactcgta aagcgagttc ggttatgagc cgtgtgcaaa acatgacatc agcttatgag      600
tcataattaa tcgtgcgtta caagtagaat tctactcgta aagcgagttg aaggatcata      660
tttagttgcg tttatgagat aagattgaaa gcacgtgtaa aatgtttccc gcgcgttggc      720
acaactattt acaatgcggc caagttataa aagattctaa tctgatatgt tttaaaacac      780
ctttgcggcc cgagttgttt gcgtacgtga ctagcgaaga agatgtgtgg accgcagaac      840
agatagtaaa acaaaaccct agtattggag caataatcga t                          881
```

<210> SEQ ID NO 28
<211> LENGTH: 2124
<212> TYPE: DNA
<213> ORGANISM: Artificial Sequence
<220> FEATURE:
<223> OTHER INFORMATION: Description of Artificial Sequence: Synthetic Recombinant DNA construct fusing the Ac-ie-01 cDNA to the polh promoter

<400> SEQUENCE: 28

```
atcatggaga taattaaaat gataaccatc tcgcaaataa ataagtattt tactgttttc       60
gtaacagttt tgtaataaaa aaacctataa atattccgga ttattcatac cgtcccacca      120
tcgggcgcgg atcccggtcc gaagcgcgcg gaattcaaag gcctacgtcg acgagctcac      180
tagtcgcggc cgctttcgaa tctagataga tctatgatcc gtacatccag ccacgtcctg      240
aacgtccaag aaaacatcat gacttccaac tgtgcttcca gcccctactc ctgtgaggcc      300
acttcagcct gcgctgaggc ccagcaactg caggtggaca caggtggcga taagatcgtg      360
aacaaccagg tcaccatgac tcaaatcaac ttcaacgctt cctacacctc tgccagcact      420
ccctctcgtg ctagcttcga caactcatac tcggagttct gcgacaagca acctaacgat      480
tacttgtctt actacaacca cccaaccccg gacggagctg atactgtcat ctccgactct      540
gaaaccgctg ccgctagcaa cttcctcgcc tcagttaact cgctcactga caacgatttg      600
gtggagtgtc tgctcaagac cactgacaac ctggaggaag ctgtgtcctc tgcctactac      660
agcgagtcac tcgaacagcc agtggtcgaa caaccctctc ctagctcagc ttaccacgcc      720
gagtccttcg aacactctgc tggtgtcaac cagccgtcgg ccacaggcac caagaggaag      780
ttggacgagt acctggataa ctcccaggga gttgtgggtc aattcaacaa gatcaagttg      840
agacctaagt acaagaagag caccatccag tcatgcgcta cactggaaca aaccatcaac      900
cacaacacta acatctgtac agtggcttcc acccaggaga tcactcacta cttcacaaac      960
gacttcgccc cctacctgat gaggttcgac gataacgact acaactcgaa cagattctcc     1020
gatcacatgt ctgaaaccgg ttactacatg ttcgtcgtta agaagtccga ggtgaagcct     1080
ttcgaaatca tcttcgccaa gtacgtctct aacgtggtct acgagtacac aaacaactac     1140
tacatggttg acaaccgtgt gttcgttgtg accttcgata agatccgctt catgatcagc     1200
tacaacctgg ttaaggagac tggcatcgaa atcccacact cacaggacgt ctgcaacgat     1260
gagaccgccg ctcaaaactg caagaagtgt cacttcgtgg acgtccacca cacattcaag     1320
gccgctctga cctcctactt caacctcgat atgtactacg ctcagacaac cttcgtgacc     1380
ttgctgcaat cactcggcga gcgtaagtgt ggattcctct tgtcgaagtt gtacgagatg     1440
```

```
taccaggaca agaacctctt cactttgccc atcatgctga gccgcaagga atcaaacgag    1500
atcgaaaccg cctctaacaa cttcttcgtc tcgccatacg tttcccagat cctcaagtac    1560
tcggagtccg tccaattccc ggacaaccct cccaacaagt acgtcgttga taacctgaac    1620
ctcatcgtga acaagaagag cactctgaca tacaagtact cgtccgtcgc taacctgctc    1680
ttcaacaact acaagtacca cgacaacatc gcttctaaca caacgccga gaacctcaag    1740 aaggtcaaga aggaagacgg aagcatgcac atcgttgagc agtacttgac tcaaaacgtc    1800
gataacgtta agggtcacaa cttcatcgtg ttgtccttca agaacgagga aaggctgacc    1860
atcgctaaga agaacaagga gttctactgg atctctggcg aaatcaagga cgttgatgtg    1920
agccaggtca tccaaaagta caacagattc aagcaccaca tgttcgtgat cggcaaggtc    1980
aaccgtcgcg agtcaactac actgcacaac aacttgctga agctcttggc cttgatcctg    2040
cagggactgg tgccactctc cgacgccatc acattcgccg agcaaaagct caactgcaag    2100
tacaagaagt tcgagttcaa ctaa                                          2124

<210> SEQ ID NO 29
<211> LENGTH: 911
<212> TYPE: DNA
<213> ORGANISM: Artificial Sequence
<220> FEATURE:
<223> OTHER INFORMATION: Description of Artificial Sequence: Synthetic
      Recombinant DNA construct fusing the GFP cDNA to the
      polh promoter

<400> SEQUENCE: 29
atcatggaga taattaaaat gataaccatc tcgcaaataa ataagtattt tactgttttc      60
gtaacagttt tgtaataaaa aaacctataa atattccgga ttattcatac cgtcccacca    120
tcgggcgcgg atccaaggcc actagtgcgg ccgctctgca gtctcgagca tgcggtacca    180
agcttgaatt catggtgagc aagggcgagg agctgttcac cggggtggtg cccatcctgg    240
tcgagctgga cggcgacgta aacggccaca agttcagcgt gtccggcgag ggcgagggcg    300
atgccaccta cggcaagctg accctgaagt tcatctgcac caccggcaag ctgcccgtgc    360
cctggcccac cctcgtgacc accctgacct acggcgtgca gtgcttcagc cgctaccccg    420
accacatgaa gcagcacgac ttcttcaagt ccgccatgcc cgaaggctac gtccaggagc    480
gcaccatctt cttcaaggac gacggcaact acaagacccg cgccgaggtg aagttcgagg    540
gcgacaccct ggtgaaccgc atcgagctga agggcatcga cttcaaggag gacggcaaca    600
tcctggggca caagctggag tacaactaca acagccacaa cgtctatatc atggccgaca    660
agcagaagaa cggcatcatg gtgaacttca agatccgcca acatcgag acggcagcg       720 tgcagctcgc cgaccactac cagcagaaca cccccatcgg cgacggcccc gtgctgctgc    780
ccgacaacca ctacctgagc acccagtccg ccctgagcaa agaccccaac gagaagcgcg    840
atcacatggt cctgctggag ttcgtgaccg ccgccgggat cactctcggc atggacgagc    900
tgtacaagta a                                                         911

<210> SEQ ID NO 30
<211> LENGTH: 1201
<212> TYPE: DNA
<213> ORGANISM: Artificial Sequence
<220> FEATURE:
<223> OTHER INFORMATION: Description of Artificial Sequence: Synthetic
      Recombinant chimeric promoter

<400> SEQUENCE: 30
```

```
atacggacct taattcaac ccaacacaat atattatagt taaataagaa ttattatcaa    60
atcatttgta tattaattaa aatactatac tgtaaattac attttattta caatcactcg   120
acggatccaa ggccactagt gcggccgcgg gaattcgatt cttgaatgtt agtgaaaccc   180
cctgcgacac aagtattaca ttccttagtg cttgaatcct ttaggaaaga aaagccaatt   240
ttcaaaatct tagcacttgt taactcgcga aaaagaccaa cagatttccc atactacaat   300
tcgacattag aaatgtaaac ccattatcat tatttacgcc tcatttccat ccaataataa   360
gtttaagtac gttgagataa aactggctta cctagaactt gacatggcga cctcttgcac   420
tctgtatctc aagtcaactt tctctatcca aatatttgat aacatttgac atgatattga   480
agtaagattg ttactaaggc ttacattgta atattactga cgcaagttct ttatcaataa   540
aatagctgaa aacaaaaaaa aaaacatcga ttagggtgac tgaaggttac attggggtag   600
gttatggtta atacgtaatg gtttaacacc aaaacgatat catggattga ctttataaat   660
tttatataag gtgtaataat atttttaatg agtggacgcg tcgggtcaat gtcctgccta   720
ttgacgtcat aacatattag gtgattatat taaaaatact caaatattac ttgcaagttt   780
aagtttcatc ataatctgat cataagtttc acccaaacag aaaccaaaag cataactatc   840
tgctatttga atatctttag cttcccatga agaaagatta ccgtaaccat cactaggatt   900
ttatacgatt gtagaaaata aagtattctc agtctctttt cagtttaaaa tctgctggca   960
tttttacaag tcgctgtatc agtcaatgtt tatacaatat gtcaatgtac tttcgtatta  1020
atcagaaaaa aatattctac tagttttgat aagctatcac ttttgttaca ttgtactgcc  1080
ctttacagtt catcaggtat ttatgaatga catattggag aaacatcgta atcagtccag  1140
tataaaaagg ggtgcattct cggtaagagt acagttgaac tcacatcgag ttaactccac  1200
g                                                                 1201
```

<210> SEQ ID NO 31
<211> LENGTH: 1207
<212> TYPE: DNA
<213> ORGANISM: Artificial Sequence
<220> FEATURE:
<223> OTHER INFORMATION: Description of Artificial Sequence: Synthetic
      Recombinant chimeric promoter

<400> SEQUENCE: 31

```
atcatggaga taattaaaat gataaccatc tcgcaaataa ataagtattt tactgttttc    60
gtaacagttt tgtaataaaa aaacctataa atattccgga ttattcatac cgtcccacca   120
tcgggcgcgg atccaaggcc actagtgcgg ccgcgggaat tcgattcttg aatgttagtg   180
aaaccccctg cgacacaagt attacattcc ttagtgcttg aatcctttag gaaagaaaag   240
ccaattttca aaatcttagc acttgttaac tcgcgaaaaa gaccaacaga tttcccatac   300
tacaattcga cattagaaat gtaaacccat tatcattatt tacgcctcat tccatccaa   360 taataagttt aagtacgttg agataaaact ggcttaccta gaacttgaca tggcgacctc   420
ttgcactctg tatctcaagt caactttctc tatccaaata tttgataaca tttgacatga   480
tattgaagta agattgttac taaggcttac attgtaatat tactgacgca agttctttat   540
caataaaata gctgaaaaca aaaaaaaaaa catcgattag ggtgactgaa ggttacattg   600
gggtaggtta tggttaatac gtaatggttt aacaccaaaa cgatatcatg gattgacttt   660 ataaattta tataaggtgt aataatatttt ttaatgagtg gacgcgtcgg gtcaatgtcc   720
tgcctattga cgtcataaca tattaggtga ttatattaaa aatactcaaa tattacttgc   780
```

```
aagtttaagt tcatcataa tctgatcata agtttcaccc aaacagaaac caaaagcata    840
actatctgct atttgaatat ctttagcttc ccatgaagaa agattaccgt aaccatcact    900
aggattttat acgattgtag aaaataaagt attctcagtc tcttttcagt ttaaaatctg    960
ctggcatttt tacaagtcgc tgtatcagtc aatgtttata caatatgtca atgtactttc   1020
gtattaatca gaaaaaaata ttctactagt tttgataagc tatcactttt gttacattgt   1080
actgcccttt acagttcatc aggtatttat gaatgacata ttggagaaac atcgtaatca   1140
gtccagtata aaaggggtg cattctcggt aagagtacag ttgaactcac atcgagttaa    1200
ctccacg                                                             1207
```

<210> SEQ ID NO 32
<211> LENGTH: 1205
<212> TYPE: DNA
<213> ORGANISM: Artificial Sequence
<220> FEATURE:
<223> OTHER INFORMATION: Description of Artificial Sequence: Synthetic
      Recombinant chimeric promoter

<400> SEQUENCE: 32

```
cttgaatgtt agtgaaaccc cctgcgacac aagtattaca ttccttagtg cttgaatcct     60
ttaggaaaga aagccaatt tcaaaatct tagcacttgt taactcgcga aaaagaccaa     120
cagatttccc atactacaat tcgacattag aaatgtaaac ccattatcat tatttacgcc    180
tcatttccat ccaataataa gtttaagtac gttgagataa aactggctta cctagaactt    240
gacatggcga cctcttgcac tctgtatctc aagtcaactt tctctatcca aatatttgat    300
aacatttgac atgatattga agtaagattg ttactaaggc ttacattgta atattactga    360
cgcaagttct ttatcaataa aatagctgaa acaaaaaaa aaaacatcga ttagggtgac    420
tgaaggttac attggggtag gttatggtta atacgtaatg gtttaacacc aaaacgatat    480
catggattga ctttataaat tttatataag gtgtaataat attttaatg agtggacgcg    540 tcgggtcaat gtcctgccta ttgacgtcat aacatattag gtgattatat taaaaatact    600
caaatattac ttgcaagttt aagtttcatc ataatctgat cataagtttc acccaaacag    660
aaaccaaaag cataactatc tgctatttga atatctttag cttcccatga agaagatta    720 ccgtaaccat cactaggatt ttatacgatt gtagaaaata agtattctc agtctctttt    780 cagttttaaa tctgctggca tttttacaag tcgctgtatc agtcaatgtt tatacaatat    840
gtcaatgtac tttcgtatta atcagaaaaa aatattctac tagttttgat aagctatcac    900
ttttgttaca ttgtactgcc ctttacagtt catcaggtat ttatgaatga catattggag    960
aaacatcgta atcagtccag tataaaaagg ggtgcattct cggtaagagt acagttgaac   1020
tcacatcgag ttaactccac gaatcactag tgaattcgcg gccgctgcag tctcgagatc   1080
atggagataa ttaaaatgat aaccatctcg caaataaata agtattttac tgttttcgta   1140
acagttttgt aataaaaaa cctataaata ttccggatta ttcataccgt cccaccatcg   1200
ggcgc                                                              1205
```

<210> SEQ ID NO 33
<211> LENGTH: 564
<212> TYPE: DNA
<213> ORGANISM: Artificial Sequence
<220> FEATURE:
<223> OTHER INFORMATION: Description of Artificial Sequence: Synthetic
      Recombinant chimeric promoter

<400> SEQUENCE: 33

```
aaaaacatcg attagggtga ctgaaggtta cattggggta ggttatggtt aatacgtaat      60
ggtttaacac caaaacgata tcatggattt tatataaggt gtaataatat ttttaatgag     120
tggacgcgtc gggtcaatgt cctgcctatt gacgtcataa catattaggt gattatatta     180
aaaatagttt aaactcaaat attacttgca agtttaagtt tcatcataat ctgatcataa     240
gtttcaccca aacagaaacc aaaagcataa ctatcgaata tctttagctt cccatgaaga     300
aagattaccg taaccatcac taggatttta tacgattgta gaaataaag tattctcagt      360 ctcttttcag agcgctataa aaggggtgc attctcggta agagtacagt tgaactcaca      420
tcgagttaac tccacgcatc atggagataa ttaaaatgat aaccatctcg caaataaata     480
agtattttac tgttttcgta acagttttgt aataaaaaaa cctataaata ttccggatta     540
ttcataccgt cccaccatcg ggcg                                            564

<210> SEQ ID NO 34
<211> LENGTH: 1041
<212> TYPE: DNA
<213> ORGANISM: Autographa californica nucleopolyhedrovirus

<400> SEQUENCE: 34
cttgaatgtt agtgaaaccc cctgcgacac aagtattaca ttccttagtg cttgaatcct      60
ttaggaaaga aaagccaatt ttcaaaatct tagcacttgt taactcgcga aaaagaccaa     120
cagatttccc atactacaat tcgacattag aaatgtaaac ccattatcat tatttacgcc     180
tcatttccat ccaataataa gtttaagtac gttgagataa aactggctta cctagaactt     240
gacatggcga cctcttgcac tctgtatctc aagtcaactt tctctatcca aatatttgat     300
aacatttgac atgatattga agtaagattg ttactaaggc ttacattgta atattactga     360
cgcaagttct ttatcaataa aatagctgaa acaaaaaaaa aaaacatcga ttagggtgac     420
tgaaggttac attggggtag gttatggtta atacgtaatg gtttaacacc aaaacgatat     480
catggattga ctttataaat tttatataag gtgtaataat attttttaatg agtggacgcg     540 tcgggtcaat gtcctgccta ttgacgtcat aacatattag gtgattatat taaaaatact     600
caaatattac ttgcaagttt aagtttcatc ataatctgat cataagtttc acccaaacag     660
aaaccaaaag cataactatc tgctatttga atatctttag cttcccatga agaaagatta     720
ccgtaaccat cactaggatt ttatacgatt gtagaaaata agtattctc agtctctttt      780 cagtttaaaa tctgctggca ttttacaag tcgctgtatc agtcaatgtt tatacaatat      840
gtcaatgtac tttcgtatta atcagaaaaa aatattctac tagttttgat aagctatcac     900
ttttgttaca ttgtactgcc ctttacagtt catcaggtat ttatgaatga catattggag     960
aaacatcgta atcagtccag tataaaagg ggtgcattct cggtaagagt acagttgaac    1020
tcacatcgag ttaactccac g                                             1041

<210> SEQ ID NO 35
<211> LENGTH: 2110
<212> TYPE: DNA
<213> ORGANISM: Artificial Sequence
<220> FEATURE:
<223> OTHER INFORMATION: Description of Artificial Sequence: Synthetic
      Recombinant expression cassette

<400> SEQUENCE: 35
atcgatgttg accccaacaa agatttata attaatcata atcacgaaca acaacaagtc       60
aatgaaacaa ataaacaagt tgtcgataaa acattcataa atgacacagc aacatacaat    120
```

```
tcttgcataa taaaaattta aatgacatca tatttgagaa taacaaatga cattatccct      180
cgattgtgtt ttacaagtag aattctaccc gtaaagcgag tttagttttg aaaaacaaat      240
gacatcattt gtataatgac atcatccccct gattgtgttt tacaagtaga attctatccg     300
taaagcgagt tcagttttga aaacaaatga gtcataccta aacacgttaa taatcttctg      360
atatcagctt atgactcaag ttatgagccg tgtgcaaaac atgagataag tttatgacat      420
catccactga tcgtgcgtta caagtagaat tctactcgta aagccagttc ggttatgagc      480
cgtgtgcaaa acatgacatc agcttatgac tcatacttga ttgtgtttta cgcgtagaat      540
tctactcgta aagcgagttc ggttatgagc cgtgtgcaaa acatgacatc agcttatgag      600
tcataattaa tcgtgcgtta caagtagaat tctactcgta aagcgagttg aaggatcata      660
tttagttgcg tttatgagat aagattgaaa gcacgtgtaa aatgtttccc gcgcgttggc      720
acaactattt acaatgcggc caagttataa aagattctaa tctgatatgt tttaaaacac      780
ctttgcggcc cgagttgttt gcgtacgtga ctagcgaaga agatgtgtgg accgcagaac      840
agatagtaaa acaaaaccct agtattggag caataatcga tgtatactcc ggaatattaa      900
tagatcatgg agataattaa aatgataacc atctcgcaaa taaataagta ttttactgtt      960
ttcgtaacag ttttgtaata aaaaaaccta taaatattcc ggattattca taccgtccca     1020
ccatcgggcg cggatccaag gccactagtg cggccgcggg aattcgattc ttgaatgtta     1080
gtgaaacccc ctgcgacaca agtattacat tccttagtgc ttgaatcctt taggaaagaa     1140
aagccaattt tcaaaatctt agcacttgtt aactcgcgaa aaagaccaac agatttccca     1200
tactacaatt cgacattaga aatgtaaacc cattatcatt atttacgcct catttccatc     1260
caataataag tttaagtacg ttgagataaa actggcttac ctagaacttg acatggcgac     1320
ctcttgcact ctgtatctca agtcaacttt ctctatccaa atatttgata acatttgaca     1380
tgatattgaa gtaagattgt tactaaggct tacattgtaa tattactgac gcaagttctt     1440
tatcaataaa atagctgaaa acaaaaaaaa aaacatcgat tagggtgact gaaggttaca     1500
ttggggtagg ttatggttaa tacgtaatgg tttaacacca aaacgatatc atggattgac     1560
tttataaatt ttatataagg tgtaataata ttttttaatga gtggacgcgt cgggtcaatg     1620
tcctgcctat tgacgtcata acatattagg tgattatatt aaaaatactc aaatattact     1680
tgcaagttta agtttcatca taatctgatc ataagtttca cccaaacaga aaccaaaagc     1740
ataactatct gctatttgaa tatctttagc ttcccatgaa gaaagattac cgtaaccatc     1800
actaggattt tatacgattg tagaaaataa agtattctca gtctcttttc agtttaaaat     1860
ctgctggcat ttttacaagt cgctgtatca gtcaatgttt atacaatatg tcaatgtact     1920
ttcgtattaa tcagaaaaaa atattctact agttttgata agctatcact tttgttacat     1980
tgtactgccc tttacagttc atcaggtatt tatgaatgac atattggaga aacatcgtaa     2040
tcagtccagt ataaaagggg gtgcattctc ggtaagagta cagttgaact cacatcgagt     2100
taactccacg                                                           2110
```

<210> SEQ ID NO 36
<211> LENGTH: 2168
<212> TYPE: DNA
<213> ORGANISM: Artificial Sequence
<220> FEATURE:
<223> OTHER INFORMATION: Description of Artificial Sequence: Synthetic Recombinant expression cassette

<400> SEQUENCE: 36

```
atcgatgttg accccaacaa aagatttata attaatcata atcacgaaca acaacaagtc      60
aatgaaacaa ataaacaagt tgtcgataaa acattcataa atgacacagc aacatacaat     120
tcttgcataa taaaaattta aatgacatca tatttgagaa taacaaatga cattatccct     180
cgattgtgtt ttacaagtag aattctaccc gtaaagcgag tttagttttg aaaaacaaat     240
gacatcattt gtataatgac atcatcccct gattgtgttt tacaagtaga attctatccg     300
taaagcgagt tcagttttga aaacaaatga gtcatacctr aacacgttaa taatcttctg     360
atatcagctt atgactcaag ttatgagccg tgtgcaaaac atgagataag tttatgacat     420
catccactga tcgtgcgtta caagtagaat tctactcgta aagccagttc ggttatgagc     480
cgtgtgcaaa acatgacatc agcttatgac tcatacttga ttgtgtttta cgcgtagaat     540
tctactcgta aagcgagttc ggttatgagc cgtgtgcaaa acatgacatc agcttatgag     600
tcataattaa tcgtgcgtta caagtagaat tctactcgta aagcgagttg aaggatcata     660
tttagttgcg tttatgagat aagattgaaa gcacgtgtaa aatgtttccc gcgcgttggc     720
acaactattt acaatgcggc caagttataa aagattctaa tctgatatgt tttaaaacac     780
ctttgcggcc cgagttgttt gcgtacgtga ctagcgaaga gatgtgtgg accgcagaac     840
agatagtaaa acaaaaccct agtattggag caataatcga tgagctcgtc gacgtaggcc     900
tttgaattcc gcgcgcttcg gaccgggatc caaggccact agtgcggccg cgggaattcg     960
attcttgaat gttagtgaaa cccctgcga cacaagtatt acattcctta gtgcttgaat    1020
cctttaggaa agaaaagcca attttcaaaa tcttagcact tgttaactcg cgaaaaagac    1080
caacagattt cccatactac aattcgacat tagaaatgta aacccattat cattattac    1140
gcctcatttc catccaataa taagtttaag tacgttgaga taaactggc ttacctagaa    1200
cttgacatgg cgacctcttg cactctgtat ctcaagtcaa ctttctctat ccaaatattt    1260
gataacattt gacatgatat tgaagtaaga ttgttactaa ggcttacatt gtaatattac    1320
tgacgcaagt tctttatcaa taaaatagct gaaaacaaaa aaaaaaacat cgattagggt    1380
gactgaaggt tacattgggg taggttatgg ttaatacgta atggtttaac accaaaacga    1440
tatcatggat tgactttata aattttatat aaggtgtaat aatatttta atgagtggac    1500
gcgtcgggtc aatgtcctgc ctattgacgt cataacatat taggtgatta tattaaaat    1560
actcaaatat tacttgcaag tttaagtttc atcataatct gatcataagt ttcacccaaa    1620
cagaaaccaa aagcataact atctgctatt tgaatatctt tagcttccca tgaagaaaga    1680
ttaccgtaac catcactagg attttatacg attgtagaaa ataaagtatt ctcagtctct    1740
tttcagttta aaatctgctg gcatttttac aagtcgctgt atcagtcaat gtttatacaa    1800
tatgtcaatg tactttcgta ttaatcagaa aaaatattc tactagtttt gataagctat    1860
cacttttgtt acattgtact gcccttaca gttcatcagg tatttatgaa tgacatattg    1920
gagaaacatc gtaatcagtc cagtataaaa aggggtgcat tctcggtaag agtacagttg    1980
aactcacatc gagttaactc cacgaatcac tagtgaattc gcggccgctg cagtctcgag    2040
atcatggaga taattaaaat gataaccatc tcgcaaataa ataagtattt tactgttttc    2100
gtaacagttt tgtaataaaa aaacctataa atattccgga ttattcatac cgtcccacca    2160
tcgggcgc                                                            2168
```

<210> SEQ ID NO 37
<211> LENGTH: 2088
<212> TYPE: DNA

<213> ORGANISM: Artificial Sequence
<220> FEATURE:
<223> OTHER INFORMATION: Description of Artificial Sequence: Synthetic Recombinant expression cassette

<400> SEQUENCE: 37

```
atcgatgttg accccaacaa aagatttata attaatcata atcacgaaca acaacaagtc      60
aatgaaacaa ataaacaagt tgtcgataaa acattcataa atgacacagc aacatacaat     120
tcttgcataa taaaaattta aatgacatca tatttgagaa taacaaatga cattatccct     180
cgattgtgtt ttacaagtag aattctaccc gtaaagcgag tttagttttg aaaaacaaat     240
gacatcattt gtataatgac atcatcccct gattgtgttt tacaagtaga attctatccg     300
taaagcgagt tcagttttga aaacaaatga gtcataccta aacacgttaa taatcttctg     360
atatcagctt atgactcaag ttatgagccg tgtgcaaaac atgagataag tttatgacat     420
catccactga tcgtgcgtta caagtagaat tctactcgta aagccagttc ggttatgagc     480
cgtgtgcaaa acatgacatc agcttatgac tcatacttga ttgtgtttta cgcgtagaat     540
tctactcgta aagcgagttc ggttatgagc cgtgtgcaaa acatgacatc agcttatgag     600
tcataattaa tcgtgcgtta caagtagaat tctactcgta aagcgagttg aaggatcata     660
tttagttgcg tttatgagat aagattgaaa gcacgtgtaa aatgtttccc gcgcgttggc     720
acaactattt acaatgcggc caagttataa aagattctaa tctgatatgt tttaaaacac     780
ctttgcggcc cgagttgttt gcgtacgtga ctagcgaaga agatgtgtgg accgcagaac     840
agatagtaaa acaaaaccct agtattggag caataatcga tgagctcata cggaccttta     900
attcaaccca acacaatata ttatagttaa ataagaatta ttatcaaatc atttgtatat     960
taattaaaat actatactgt aaattacatt ttatttacaa tcactcgacg gatccaaggc    1020
cactagtgcg gccgcgggaa ttcgattctt gaatgttagt gaaacccccct gcgacacaag    1080
tattacattc cttagtgctt gaatccttta ggaaagaaaa gccaattttc aaaatcttag    1140
cacttgttaa ctcgcgaaaa agaccaacag atttcccata ctacaattcg acattagaaa    1200
tgtaaaccca ttatcattat ttacgcctca tttccatcca ataataagtt taagtacgtt    1260
gagataaaac tggcttacct agaacttgac atggcgacct cttgcactct gtatctcaag    1320
tcaactttct ctatccaaat atttgataac atttgacatg atattgaagt aagattgtta    1380
ctaaggctta cattgtaata ttactgacgc aagttcttta tcaataaaat agctgaaaac    1440
aaaaaaaaaa acatcgatta gggtgactga aggttacatt ggggtaggtt atggttaata    1500
cgtaatggtt taacaccaaa acgatatcat ggattgactt tataaatttt atataaggtg    1560
taataatatt tttaatgagt ggacgcgtcg ggtcaatgtc ctgcctattg acgtcataac    1620
atattaggtg attatattaa aaatactcaa atattacttg caagtttaag tttcatcata    1680
atctgatcat aagtttcacc caaacagaaa ccaaaagcat aactatctgc tatttgaata    1740
tctttagctt cccatgaaga aagattaccg taaccatcac taggatttta tacgattgta    1800
gaaaataaag tattctcagt ctcttttcag tttaaaatct gctggcattt ttacaagtcg    1860
ctgtatcagt caatgtttat acaatatgtc aatgtacttt cgtattaatc agaaaaaaat    1920
attctactag ttttgataag ctatcacttt tgttacattg tactgcccctt tacagttcat    1980
caggtattta tgaatgacat attggagaaa catcgtaatc agtccagtat aaaaagggggt   2040
gcattctcgg taagagtaca gttgaactca catcgagtta actccacg                 2088
```

<210> SEQ ID NO 38

<211> LENGTH: 2162
<212> TYPE: DNA
<213> ORGANISM: Artificial Sequence
<220> FEATURE:
<223> OTHER INFORMATION: Description of Artificial Sequence: Synthetic Recombinant expression cassette

<400> SEQUENCE: 38

| | | | | | |
|---|---|---|---|---|---|
| atcgatgttg | accccaacaa | aagatttata | attaatcata | atcacgaaca | acaacaagtc | 60 |
| aatgaaacaa | ataaacaagt | tgtcgataaa | acattcataa | atgacacagc | aacatacaat | 120 |
| tcttgcataa | taaaaattta | aatgacatca | tatttgagaa | taacaaatga | cattatccct | 180 |
| cgattgtgtt | ttacaagtag | aattctaccc | gtaaagcgag | tttagttttg | aaaaacaaat | 240 |
| gacatcattt | gtaatgac | atcatcccct | gattgtgttt | tacaagtaga | attctatccg | 300 |
| taaagcgagt | tcagttttga | aaacaaatga | gtcatacca | aacacgttaa | taatcttctg | 360 |
| atatcagctt | atgactcaag | ttatgagccg | tgtgcaaaac | atgagataag | tttatgacat | 420 |
| catccactga | tcgtgcgtta | caagtagaat | tctactcgta | aagccagttc | ggttatgagc | 480 |
| cgtgtgcaaa | acatgacatc | agcttatgac | tcatacttga | ttgtgtttta | cgcgtagaat | 540 |
| tctactcgta | aagcgagttc | ggttatgagc | cgtgtgcaaa | acatgacatc | agcttatgag | 600 |
| tcataattaa | tcgtgcgtta | caagtagaat | tctactcgta | aagcgagttg | aaggatcata | 660 |
| tttagttgcg | tttatgagat | aagattgaaa | gcacgtgtaa | aatgtttccc | gcgcgttggc | 720 |
| acaactattt | acaatgcggc | caagttataa | aagattctaa | tctgatatgt | tttaaaacac | 780 |
| ctttgcggcc | cgagttgttt | gcgtacgtga | ctagcgaaga | agatgtgtgg | accgcagaac | 840 |
| agatagtaaa | acaaaaccct | agtattggag | caataatcga | tgagctcgtc | gacgtaggcc | 900 |
| tttgaattcc | gcgcgcttcg | gaccgggatc | caaggccact | agtgcggccg | cgggaattcg | 960 |
| attcttgaat | gttagtgaaa | cccctgcga | cacaagtatt | acattcctta | gtgcttgaat | 1020 |
| cctttaggaa | agaaaagcca | attttcaaaa | tcttagcact | tgttaactcg | cgaaaaagac | 1080 |
| caacagattt | cccatactac | aattcgacat | tagaaatgta | aacccattat | cattatttac | 1140 |
| gcctcatttc | catccaataa | taagtttaag | tacgttgaga | taaaactggc | ttacctagaa | 1200 |
| cttgacatgg | cgacctcttg | cactctgtat | ctcaagtcaa | ctttctctat | ccaaatattt | 1260 |
| gataacattt | gacatgatat | tgaagtaaga | ttgttactaa | ggcttacatt | gtaatattac | 1320 |
| tgacgcaagt | tctttatcaa | taaaatagct | gaaaacaaaa | aaaaaacat | cgattagggt | 1380 |
| gactgaaggt | tacattgggg | taggttatgg | ttaatacgta | atggtttaac | accaaaacga | 1440 |
| tatcatggat | tgactttata | aatttttatat | aaggtgtaat | aatattttta | atgagtggac | 1500 |
| gcgtcgggtc | aatgtcctgc | ctattgacgt | cataacatat | taggtgatta | tattaaaaat | 1560 |
| actcaaatat | tacttgcaag | tttaagtttc | atcataatct | gatcataagt | ttcacccaaa | 1620 |
| cagaaaccaa | aagcataact | atctgctatt | tgaatatctt | tagcttccca | tgaagaaaga | 1680 |
| ttaccgtaac | catcactagg | attttatacg | attgtagaaa | ataaagtatt | ctcagtctct | 1740 |
| tttcagttta | aaatctgctg | gcatttttac | aagtcgctgt | atcagtcaat | gtttatacaa | 1800 |
| tatgtcaatg | tactttcgta | ttaatcagaa | aaaatattc | tactagtttt | gataagctat | 1860 |
| cacttttgtt | acattgtact | gcccttaca | gttcatcagg | tatttatgaa | tgacatattg | 1920 |
| gagaaacatc | gtaatcagtc | cagtataaaa | aggggtgcat | tctcggtaag | agtacagttg | 1980 |
| aactcacatc | gagttaactc | cacgaatcac | tagtgaattc | gcggccgctg | cagtctcgag | 2040 |
| atacggacct | ttaattcaac | ccaacacaat | atattatagt | taaataagaa | ttattatcaa | 2100 |

```
atcatttgta tattaattaa aatactatac tgtaaattac attttattta caatcactcg    2160
ac                                                                    2162

<210> SEQ ID NO 39
<211> LENGTH: 1508
<212> TYPE: DNA
<213> ORGANISM: Artificial Sequence
<220> FEATURE:
<223> OTHER INFORMATION: Description of Artificial Sequence: Synthetic
      Recombinant expression cassette

<400> SEQUENCE: 39
atcgatgttg accccaacaa aagatttata attaatcata atcacgaaca acaacaagtc      60
aatgaaacaa ataaacaagt tgtcgataaa acattcataa atgacacagc aacatacaat     120
tcttgcataa taaaaattta aatgacatca tatttgagaa taacaaatga cattatccct     180
cgattgtgtt ttacaagtag aattctaccc gtaaagcgag tttagttttg aaaaacaaat     240
gacatcattt gtataatgac atcatcccct gattgtgttt tacaagtaga attctatccg     300
taaagcgagt tcagttttga aaacaaatga gtcataccta aacacgttaa taatcttctg     360
atatcagctt atgactcaag ttatgagccg tgtgcaaaac atgagataag tttatgacat     420
catccactga tcgtgcgtta caagtagaat tctactcgta aagccagttc ggttatgagc     480
cgtgtgcaaa acatgacatc agcttatgac tcatacttga ttgtgtttta cgcgtagaat     540
tctactcgta aagcgagttc ggttatgagc cgtgtgcaaa acatgacatc agcttatgag     600
tcataattaa tcgtgcgtta caagtagaat tctactcgta aagcgagttg aaggatcata     660
tttagttgcg tttatgagat aagattgaaa gcacgtgtaa aatgtttccc gcgcgttggc     720
acaactattt acaatgcggc caagttataa aagattctaa tctgatatgt tttaaaacac     780
ctttgcggcc cgagttgttt gcgtacgtga ctagcgaaga agatgtgtgg accgcagaac     840
agatagtaaa acaaaaccct agtattggag caataatcga tgagctcgtc gacgtaggcc     900
tttgaattcc gcgcgcttcg gaccgggatc caaaaacatc gattagggtg actgaaggtt     960
acattggggt aggttatggt taatacgtaa tggtttaaca ccaaaacgat atcatggatt    1020
ttatataagg tgtaataata tttttaatga gtggacgcgt cgggtcaatg tcctgcctat    1080
tgacgtcata acatattagg tgattatatt aaaaatagtt taaactcaaa tattacttgc    1140
aagtttaagt ttcatcataa tctgatcata agtttcaccc aaacagaaac caaaagcata    1200
actatcgaat atctttagct tcccatgaag aaagattacc gtaaccatca ctaggatttt    1260
atacgattgt agaaaataaa gtattctcag tctcttttca gagcgctata aaaaggggtg    1320
cattctcggt aagagtacag ttgaactcac atcgagttaa ctccacgctg cagtctcgag    1380
atcatggaga taattaaaat gataaccatc tcgcaaataa ataagtattt tactgttttc    1440
gtaacagttt tgtaataaaa aaacctataa atattccgga ttattcatac cgtcccacca    1500
tcgggcgc                                                             1508

<210> SEQ ID NO 40
<211> LENGTH: 1502
<212> TYPE: DNA
<213> ORGANISM: Artificial Sequence
<220> FEATURE:
<223> OTHER INFORMATION: Description of Artificial Sequence: Synthetic
      Recombinant expression cassette
```

```
<400> SEQUENCE: 40
atcgatgttg accccaacaa aagatttata attaatcata atcacgaaca acaacaagtc      60
aatgaaacaa ataaacaagt tgtcgataaa acattcataa atgacacagc aacatacaat     120
tcttgcataa taaaaattta aatgacatca tatttgagaa taacaaatga cattatccct     180
cgattgtgtt ttacaagtag aattctaccc gtaaagcgag tttagttttg aaaaacaaat     240
gacatcattt gtataatgac atcatcccct gattgtgttt tacaagtaga attctatccg     300
taaagcgagt tcagttttga aaacaaatga gtcatatccta aacacgttaa taatcttctg    360
atatcagctt atgactcaag ttatgagccg tgtgcaaaac atgagataag tttatgacat     420
catccactga tcgtgcgtta caagtagaat tctactcgta aagccagttc ggttatgagc     480
cgtgtgcaaa acatgacatc agcttatgac tcatacttga ttgtgtttta cgcgtagaat     540
tctactcgta aagcgagttc ggttatgagc cgtgtgcaaa acatgacatc agcttatgag     600
tcataattaa tcgtgcgtta caagtagaat tctactcgta aagcgagttg aaggatcata     660
tttagttgcg tttatgagat aagattgaaa gcacgtgtaa aatgtttccc gcgcgttggc     720
acaactattt acaatgcggc caagttataa aagattctaa tctgatatgt tttaaaacac     780
ctttgcggcc cgagttgttt gcgtacgtga ctagcgaaga agatgtgtgg accgcagaac     840
agatagtaaa acaaaaccct agtattggag caataatcga tgagctcgtc gacgtaggcc     900
tttgaattcc gcgcgcttcg gaccgggatc caaaaacatc gattagggtg actgaaggtt     960
acattggggt aggttatggt taatacgtaa tggtttaaca ccaaaacgat atcatggatt    1020
ttatataagg tgtaataata ttttaatga gtggacgcgt cgggtcaatg tcctgcctat    1080
tgacgtcata acatattagg tgattatatt aaaaatagtt taaactcaaa tattacttgc    1140
aagtttaagt ttcatcataa tctgatcata agtttcaccc aaacagaaac caaaagcata    1200
actatcgaat atctttagct tcccatgaag aaagattacc gtaaccatca ctaggatttt    1260
atacgattgt agaaaataaa gtattctcag tctcttttca gagcgctata aaaaggggtg    1320
cattctcggt aagagtacag ttgaactcac atcgagttaa ctccacgctg cagtctcgag    1380 atacggaccct ttaattcaac ccaacacaat atattatagt taaataagaa ttattatcaa    1440
atcatttgta tattaattaa aatactatac tgtaaattac attttattta caatcactcg    1500
ac                                                                  1502

<210> SEQ ID NO 41
<211> LENGTH: 4
<212> TYPE: PRT
<213> ORGANISM: Unknown
<220> FEATURE:
<223> OTHER INFORMATION: Description of Unknown:
      retention signal peptide sequence

<400> SEQUENCE: 41

Lys Asp Glu Leu
1
```

BACULOVIRAL DNA ELEMENTS FOR THE EXPRESSION OF RECOMBINANT PROTEINS IN A HOST CELL

SEQUENCE LISTING

The instant application contains a Sequence Listing which has been submitted electronically in ASCII format and is hereby incorporated by reference in its entirety. Said ASCII copy, created on Jan. 17, 2017, is named 117814_27101_SL.txt and is 106,325 bytes in size.

RELATED APPLICATIONS

This application is a 35 U.S.C. § 371 national stage filing of International Application No. PCT/EP2012/061081, filed on Jun. 12, 2012, the entire contents of which are explicitly incorporated herein by reference.

FIELD OF THE INVENTION

The present invention may be included in the field of biotechnology and it covers nucleic acid sequences comprising such as promoters, homologous regions (hr) as enhancers, and sequences encoding transcriptional regulators, for example, the baculovirus Ac-ie-01 cDNA, or any combination thereof, which are able to increase the quality and efficiency of recombinant protein production. Moreover, the present invention is also directed to the vectors themselves comprising the above mentioned nucleic acid sequences of the invention, cells infected, transformed or transfected with those sequences or vectors, and methods for producing proteins by using the aforesaid sequences, vectors or cells.

STATE OF THE ART

The baculovirus expression vector system (BEVS) is a well-established method for the production of recombinant proteins to be used as vaccines, therapeutic molecules or diagnostic reagents. With its potential for over-expression and rapid speed of development, BEVS is one of the most attractive choices for producing recombinant proteins for any purpose. The most employed baculovirus used in industry for recombinant protein expression is based on *Autographa californica* multinuclear polyhedrosis virus (AcMNPV) with *Spodoptera frugiperda* 9 (Sf9) or 21 (Sf21) insect cells as suitable expression hosts (1), as well as *Trichoplusia ni* (*T. ni*) insect larvae as living biofactories (2). Since the BEVS was developed in the 80's (3), hundreds of recombinant proteins, ranging from cytosolic enzymes to membrane-bound proteins, have been successfully produced in baculovirus-infected insect cells.

Efforts have been made to increase BEVS productivity (4). A variety of transfer vectors are available for the construction of recombinant baculoviruses, encoding resident fusion proteins, which have been reported to improve protein expression, including maltose binding protein, glutathione S transferase, SUMO and KDEL retention signal (SEQ ID NO: 41). Other attempts related to improve the stability of expressed proteins have been investigated focusing on two genes in the baculovirus genome, which are not essential for growth of the virus in cell culture, namely chiA (chitinase) and cath (cathepsin). ChiA deletion appears to improve the production of secreted proteins by accumulating the protein in the endoplasmic reticulum and processing the proteins through the secretory pathway of the cells. Additionally, the prevention of the formation of cathepsin protease may also contribute to improved product stability from chiA- viruses. Novel insect cell lines, such as High-FiveTM (Hi-5) or BTI-TnAo38 cell lines from *T. ni*, have recently been developed to increase the baculovirus productivity with significant improvements in the final amount of heterologous protein recovery (5, 6).

Accelerating recombinant protein expression, so that protein expression takes place before the machinery of insect cells is severely impaired by the baculovirus infection, would be an important improvement of the BEVS. Late expression, driven by the conventional strong virus promoters of polyhedrin (polh) or p10 genes, has serious disadvantages in the foreign protein post-translational modifications. Baculovirus promoters that allow for earlier expression than the conventionally used polh or p10 promoters have been characterized and been used for heterologous protein production, but showed a reduced productivity (7).

Another possibility for improving the BEVS would be to increase preservation of cell integrity at late times post-infection by reducing the virus-induced cell death. Reduction in the severe impairment of the insect cell machinery at late times post-infection caused by REVS should not only increase the time frame for producing and accumulating recombinant proteins (secreted or not), but also allow more time for the folding of complex proteins or any post-translational modification of the produced proteins.

Some baculovirus DNA elements have been determined to be involved in the activation of late expression factor genes, which are necessary for virus propagation. One of them is the immediate early (ie) protein IE-1 and its splice variant IE-0 from AcMNPV (*Autographa californica* multinuclear polyhedrosis virus). Translation of the AcMNPV mRNAs encoded by Ac-ie-01 gene results in both IE-0 and IE-1 due to internal translation initiation. Both are thought to be critical mediators of baculovirus gene expression due to their potency as transcriptional regulators (8). Synthesized very early during infection, AcMNPV IE-1 is a 67-kDa dimeric DNA-binding protein that stimulates transcription in plasmid transfection assays through the activity of its N-terminal acidic domain (9, 10). IE-1 accumulates within the nucleus, where it is maintained through late times (11). Transactivation by IE-1 is enhanced by its binding as a homodimer to the baculovirus homologous region (hr) sequences, which function as transcriptional enhancers and origins of viral DNA replication. AcMNPV IE-0 is a 72.6-kDa 636 amino acid protein composed of 38 amino acids encoded by orf141 (exon0), 16 amino acids encoded by the upstream nontranslated leader of ie1, and the entire 582 amino acid IE-1 protein. The final product is therefore identical to IE-1 except for the additional 54 amino acids fused to the N-terminus. Presumably due to their common sequences, IE-0 and IE-1 share biochemical activities, including hr enhancer binding and transcriptional regulation.

There is a need of novel alternative BEVSs that allow a) stronger expression than the commercial BEVS that use the polh or p10 promoters and b) long-term expression in the baculovirus system by reducing virus-induced cell damage.

SUMMARY OF THE INVENTION

The present invention provides products and methods for the improved expression of recombinant proteins using the BEVS.

The following items are preferred embodiments for allowing this improved expression:

1. Recombinant baculovirus comprising a nucleic acid sequence that allows for the expression above endogenous levels of the proteins IE-1, IE-0 and/or fragments thereof functioning as transcriptional regulators, wherein the nucleic acid is selected from the group consisting of:
   (a) a nucleic acid containing the nucleotide sequence indicated in any of SEQ ID NO: 2-5;
   (b) a nucleic acid sequence having a sequence identity of at least 70%, preferably at least 75%, more preferably at least 80%, more preferably at least 85%, more preferably at least 90% and most preferably at least 95% with the nucleotide sequence indicated in any of SEQ ID NO: 2-5 and encoding a protein able to function as a transcriptional regulator in a recombinant baculovirus;
   (c) a nucleic acid sequence encoding an amino acid containing the amino acid sequence indicated in any of SEQ ID NO: 6-9; and
   (d) a nucleic acid sequence encoding an amino acid sequence having a sequence similarity of at least 70%, preferably at least 75%, more preferably at least 80%, more preferably at least 85%, more preferably at least 90% and most preferably at least 95% with the amino acid sequence indicated in any of SEQ ID NO: 6-9 and able to function as a transcriptional regulator in a recombinant baculovirus.
2. Recombinant baculovirus according to item 1, further comprising at least one recombinant homologous region (hr) as enhancer region, operably linked to any promoter that is suitable for driving the expression of a recombinant protein.
3. Recombinant baculovirus according to item 2, wherein the recombinant homologous region (hr) is the sequence indicated in SEQ ID NO: 27 (hr1).
4. Recombinant baculovirus according to item 2 or 3, wherein the promoter operably linked to the homologous region (hr) is selected from the group of nucleic acids comprising:
   (a) a nucleic acid containing the nucleotide sequence indicated in any of SEQ ID NO: 10-16; and
   (b) a nucleic acid sequence able to function as a promoter in a recombinant baculovirus and having a sequence identity of at least 70%, preferably at least 75%, more preferably at least 80%, more preferably at least 85%, more preferably at least 90% and most preferably at least 95% with the nucleotide sequence indicated in any of SEQ ID NO: 10-16.
5. Recombinant baculovirus according to any of the items 1-4, comprising a nucleic acid sequence that comprises combinations of recombinant promoters, sequences encoding transcriptional regulators and enhancer regions selected from the group comprising SEQ ID NO: 17-26.
6. Recombinant baculovirus according to any of the items 1-5, further comprising a nucleic acid sequence encoding a recombinant protein, wherein said nucleic acid sequence is operably linked to a nucleic acid sequence selected from the group consisting of the nucleic acid sequences of items 1-5.
7. Transfer vector suitable for producing a recombinant baculovirus according to any of the items 1-6, comprising said sequence for expression above endogenous levels of the proteins IE-0, IE-1 and/or fragments thereof functioning as transcriptional regulators, further comprising a nucleic acid sequence suitable for integration or transposition in a baculovirus.
8. Transfer vector according to item 7, further comprising at least one recombinant homologous region (hr) as enhancer region, operably linked to any promoter that is suitable for driving the expression of a recombinant protein.
9. Transfer vector according to item 8, wherein the recombinant homologous region (hr) is the sequence indicated in SEQ ID NO: 27 (hr1).
10. Transfer vector according to item 8 or 9, wherein the promoter operably linked to the homologous region (hr) is selected from the group of nucleic acids comprising:
    (a) a nucleic acid containing the nucleotide sequence indicated in any of SEQ ID NO: 10-16; and
    (b) a nucleic acid sequence able to function as a promoter in a recombinant baculovirus and having a sequence identity of at least 70%, preferably at least 75%, more preferably at least 80%, more preferably at least 85%, more preferably at least 90% and most preferably at least 95% with the nucleotide sequence indicated in any of SEQ ID NO: 10-16.
11. Transfer vector according to any of the items 7-10, comprising a nucleic acid sequence that comprises combinations of recombinant promoters, sequences encoding transcriptional regulators and enhancer regions selected from the group comprising SEQ ID NO: 17-26.
12. Transfer vector according to any of the items 7-11, further comprising a nucleic acid sequence encoding a recombinant protein, wherein said nucleic acid sequence is operably linked to a nucleic acid sequence selected from the group consisting of the nucleic acid sequences of items 7-11.
13. Transfer vector according to any of the items 7-11, lacking a nucleic acid sequence encoding a recombinant protein.
14. Transfer vector according to any of the items 7-13, characterized in that the transfer vector is a bacmid.
15. Transfer vector according to any of the items 7-14, characterized in that the transfer vector is derived from any of the baculovirus expression systems "Bac-to-Bac®" (Invitrogen™), "BacPAK™" (Clontech™), "FlashBAC™" (Oxford Expression Technologies™), "BacuVance™" (GenScript™), "Bac-N-Blue DNA™" (Invitrogen™), "BaculoDirect™" (Invitrogen™), "BacVector®" 1000, 2000, 3000 (Novagen®), "DiamondBac™" (Sigma-Aldrich®) or "BaculoGold™" (BD Biosciences™).
16. Cloning vector suitable for producing a recombinant baculovirus or transfer vector according to any of the items 1-15, comprising said sequence for expression above endogenous levels of the proteins IE-0, IE-1 and/or fragments thereof functioning as transcriptional regulators, which is further suitable for bacterial replication.
17. Cloning vector according to item 16, further comprising at least one recombinant homologous region (hr) as enhancer region, operably linked to any promoter that is suitable for driving the expression of a recombinant protein.
18. Cloning vector according to item 17, wherein the recombinant homologous region (hr) is the sequence indicated in SEQ ID NO: 27 (hr1).
19. Cloning vector according to item 17 or 18, wherein the promoter operably linked to the homologous region (hr) is selected from the group of nucleic acids comprising:

(a) a nucleic acid containing the nucleotide sequence indicated in any of SEQ ID NO: 10-16; and
(b) a nucleic acid sequence able to function as a promoter in a recombinant baculovirus and having a sequence identity of at least 70%, preferably at least 75%, more preferably at least 80%, more preferably at least 85%, more preferably at least 90% and most preferably at least 95% with the nucleotide sequence indicated in any of SEQ ID NO: 10-16.

20. Cloning vector according to any of the items 16-19, comprising a nucleic acid sequence that comprises combinations of recombinant promoters, sequences encoding transcriptional regulators and enhancer regions selected from the group comprising SEQ ID NO: 17-26.

21. Cloning vector according to any of the items 16-20, further comprising a nucleic acid sequence encoding a recombinant protein, wherein said nucleic acid sequence is operably linked to a nucleic acid sequence selected from the group consisting of the nucleic acid sequences of items 16-20.

22. Cloning vector according to any of the items 16-20, lacking a nucleic acid sequence encoding a recombinant protein.

23. Nucleic acid sequence suitable for producing a recombinant baculovirus, transfer vector or cloning vector according to any of the items 1-22, comprising said sequence for expression above endogenous levels of the proteins IE-0, IE-1 and/or fragments thereof functioning as transcriptional regulators.

24. Nucleic acid sequence according to item 23, further comprising at least one recombinant homologous region (hr) as enhancer region, operably linked to any promoter that is suitable for driving the expression of a recombinant protein.

25. Nucleic acid sequence according to item 24, wherein the recombinant homologous region (hr) is the sequence indicated in SEQ ID NO: 27 (hr1).

26. Nucleic acid sequence according to item 24 or 25, wherein the promoter operably linked to the homologous region (hr) is selected from the group of nucleic acids comprising:
(a) a nucleic acid containing the nucleotide sequence indicated in any of SEQ ID NO: 10-16; and
(b) a nucleic acid sequence able to function as a promoter in a recombinant baculovirus and having a sequence identity of at least 70%, preferably at least 75%, more preferably at least 80%, more preferably at least 85%, more preferably at least 90% and most preferably at least 95% with the nucleotide sequence indicated in any of SEQ ID NO: 10-16.

27. Nucleic acid sequence according to any of the items 23-26, comprising a nucleic acid sequence that comprises combinations of recombinant promoters, sequences encoding transcriptional regulators and enhancer regions selected from the group comprising SEQ ID NO: 17-26.

28. Nucleic acid sequence according to any of the items 23-27, further comprising a nucleic acid sequence encoding a recombinant protein, wherein said nucleic acid sequence is operably linked to a nucleic acid sequence selected from the group consisting of the nucleic acid sequences of items 23-27.

29. Nucleic acid sequence according to any of the items 23-27, lacking a nucleic acid sequence encoding a recombinant protein.

30. A host cell infected, transfected, transduced or transformed with the recombinant baculovirus, transfer vector, cloning vector or nucleic acid sequence of any of the items 1-29.

31. Infected, transfected, transduced or transformed host cell according to item 30, characterized in that it is an insect cell line.

32. Infected, transfected, transduced or transformed host cell according to item 30 or 31, characterized in that it is derived from an insect belonging to the *Lepidoptera* or *Diptera* genus.

33. Infected, transfected, transduced or transformed host cell according to any of the items 30-32, characterized in that it is derived from *Trichoplusia ni, Spodoptera frugiperda, Ascalapha odorata, Bornbyx mori, Drosophila melanogaster* or *Aedes aegypti*.

34. Infected, transfected, transduced or transformed host cell according to any of the items 30-33, characterized in that it is a cell line selected from the group consisting of Hi-5™, Sf9, Sf21, BTI-Tn5B-1, Tn368, ExpresSf+ ®, BTI-TnAo38, ATC-10 and Schneider's *Drosophila* Line 2.

35. Culture medium comprising the recombinant baculovirus, transfer vector, cloning vector or nucleic acid sequence of any of the items 1-29.

36. Method for producing a recombinant protein that comprises the infected, transfected, transduced or transformed host cell according to items 30-34 and the extraction and purification of the recombinant protein by conventional means.

37. Method for producing a recombinant protein according to item 36, wherein the recombinant protein is selected from the group comprising subunit monomeric vaccine, subunit multimeric vaccine, virus like particle, therapeutic protein, antibody, enzyme, cytokine, blood clotting factor, anticoagulant, receptor, hormone and diagnostic protein reagent.

38. Use of the transfer vector according to any of the items 7-15 for producing a recombinant baculovirus according to any of the items 1-6.

39. Use of the cloning vector according to any of the items 16-22 for producing a recombinant baculovirus or transfer vector according to any of the items 1-15.

40. Use of the nucleic acid sequence according to any of the items 23-29 for producing a recombinant baculovirus, transfer vector or cloning vector according to any of the items 1-22.

41. Transgenic cell line comprising a transgene, which is a nucleic acid selected from the group consisting of:
(a) a nucleic acid containing the nucleotide sequence indicated in any of SEQ ID NO: 2-5;
(b) a nucleic acid sequence having a sequence identity of at least 70%, preferably at least 75%, more preferably at least 80%, more preferably at least 85%, more preferably at least 90% and most preferably at least 95% with the nucleotide sequence indicated in any of SEQ ID NO: 2-5 and encoding a protein able to function as a transcriptional regulator in a recombinant baculovirus;
(c) a nucleic acid sequence encoding an amino acid containing the amino acid sequence indicated in any of SEQ ID NO: 6-9; and
(d) a nucleic acid sequence encoding an amino acid sequence having a sequence similarity of at least 70%, preferably at least 75%, more preferably at least 80%, more preferably at least 85%, more preferably at least 90% and most preferably at least 95% with the amino acid sequence indicated in any of SEQ ID NO: 6-9 and able to function as a transcriptional regulator in a recombinant baculovirus.

42. Transgenic cell line according to item 41, which is of insect, avian or mammalian origin.

43. Method for producing a recombinant protein that comprises growth of a transgenic cell line according to item 41 or 42 and the extraction and purification of the recombinant protein by conventional means.

44. Nucleic acid sequence comprising a nucleic acid sequence functioning as a promoter in a recombinant baculovirus, wherein the nucleic acid sequence is selected from the group consisting of:
   (a) a nucleic acid containing the nucleotide sequence indicated in SEQ ID NO: 12, 14 or 15; and
   (b) a nucleic acid sequence having a sequence identity of at least 70%, preferably at least 75%, more preferably at least 80%, more preferably at least 85%, more preferably at least 90% and most preferably at least 95% with the nucleotide sequence indicated in SEQ ID NO: 12, 14 or 15.

BRIEF DESCRIPTION OF THE FIGURES

FIG. 6. Sf9 insect cells were cultured in suspension and infected by a baculovirus overexpressing the Ac-ie-01 cDNA under the control of polh or by a baculovirus expressing a reporter protein GFP in the context of the baculovirus expression cassette polhAc-ie-01/hr1p6.9p10GFP of the present invention to assess the cell density (A) and viability (B) of these cells. As a control, a conventional baculovirus expressing the GFP protein under the control of polh was used. Cells were infected in suspension at a MOI of 0.1. (A) The cells were counted at different times post-infection (0, 24 and 48 hours) to calculate the cell density. A more detailed analysis of the precise moment in which cell proliferation is produced by the overexpression of the Ac-ie-01 cDNA is shown in the insert for cells infected with polhGFP or polhAc-ie-01/hr1p6.9p10GFP. (B) Cell viability was assessed by Trypan blue staining (dilution 1:1 of suspended cells and colorant at 0.4% in PBS buffer). This staining allows the differentiation between live and death cells. Cell viability was calculated by the percentage of living cells with respect to the total number of cells at different times post-infection (from 0 to 120 hours). Micrographs of Hi-5™ insect cell monolayers infected at a MOI of 5 with a control conventional baculovirus overexpressing the reporter protein GFP under the polh promoter (C) or with a baculovirus overexpressing the Ac-ie-01 cDNA under the control of the polh promoter (D). Micrographs were obtained at 96 hours post-infection at a 20× magnification in an inverted microscope Leica™ DMIL™.

FIG. 9: Sequence analysis of the pB2 promoter isolated from *T. ni* and determination of the transcriptional regulatory element pB29 sequence (SEQ ID NO: 34). A) Nucleotide sequence of the pB2 promoter region of BJHSP2 (Genbank accession no U41640) isolated from *T. ni*. The previously described transcription start site is indicated by a triangle, whereas the TATA box is underlined and the potential cis-acting elements are enclosed in boxes in the pB2 sequence. Shaded nucleotide residues indicate the sequence incorporated into the pB29 promoter. The predicted Br-C and EcR putative binding sites are also indicated in the figure by transparent boxes B) Schematic illustration of the pB2 DNA fragment and its derivative promoter pB29. Their promoter activity was analyzed by fluorimetric analysis using the GFP protein as the reporter gene. The GFP expression was quantified 72 hours post-infection in all experiments and is indicated as the arithmetic media with standard deviations of three independent experiments.

DETAILED DESCRIPTION OF THE INVENTION

Figure 1:
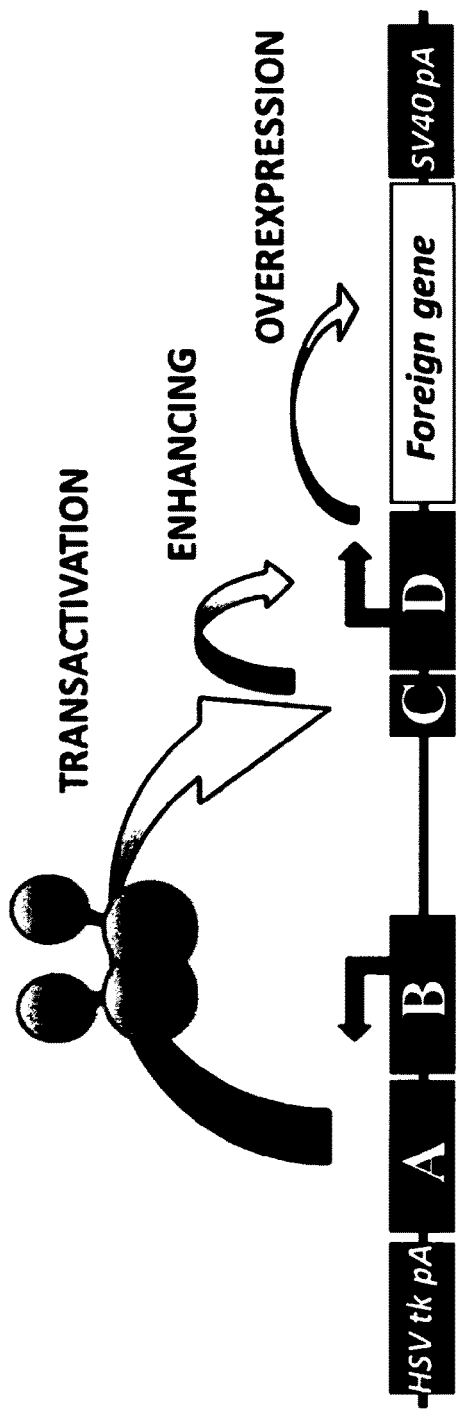
FIG. 1: Schematic representation of the baculovirus recombinant DNA elements of the invention, comprising four principal elements: a sequence encoding for transcriptional regulators (A; e.g. IE0 and IE1), which expression is driven by a promoter (B; e.g. polh or pB2$_9$); an enhancer homologous region (hr) sequence (C; e.g. hr1), upstream of the promoters (D; e.g. p10, polh, pB2$_9$p10 or p6.9p10) driving the expression of the foreign gene coding for the recombinant protein. The scheme shows the theoretical mechanism of interaction between the recombinant DNA elements of the present invention that results in the unprecedented overexpression of the recombinant protein.

The present invention improves the expression of recombinant proteins in the BEVS by means of the introduction of recombinant DNA elements into baculoviruses.

The recombinant DNA elements of the present invention are sequences that cause the expression of baculovirus transcriptional regulators above endogenous levels and optionally enhancer homologous regions (hr) and promoters operably linked to these aforementioned elements.

Furthermore, the recombinant DNA elements may form part of an expression cassette.

"Expression cassette" refers to a nucleic acid sequence that contains recombinant DNA elements, which control (e.g. the promoter) and/or are required (e.g. the gene itself) for gene expression. The expression cassette can be introduced in a recombinant vector or baculovirus.

The recombinant DNA elements may be incorporated in a single nucleic acid sequence, cloning vector, transfer vector, recombinant baculovirus or cell. However, they can also be present in different nucleic acid sequences, cloning vectors, transfer vectors or recombinant baculoviruses and be introduced into the same cell.

The present invention surprisingly shows that introduction of sequences that cause the expression of baculovirus transcriptional regulators above endogenous levels and optionally the introduction of an enhancer homologous region Or) sequence, a promoter or a combination of promoters is able to increase the production of a recombinant protein to unprecedented levels from early (6 to 8 hours post-infection) to late (48 to 96-120 hours post-infection) times post-infection.

Additionally, the introduction of these recombinant DNA elements also increases the proliferation of baculovirus-infected cells (particularly at early times post-infection), the viability at late times post-infection and the integrity of the molecular cell machinery and morphology of said baculovirus-infected cells. An improvement in the integrity of cell functions during baculovirus infections also contributes to the correct post-translational processing of the recombinant protein.

Introduction of these recombinant DNA elements also increases the recombinant protein production in host cells compared to the conventional polh or p10 promoters.

Thus, one aspect of the invention relates to a recombinant baculovirus that contains a nucleic acid sequence that allows for the expression above endogenous levels of transcriptional regulators. In a preferred embodiment, the transcriptional regulators are IE-1, IE-0 and/or fragments thereof.

"Baculovirus" refers to a family of infectious viruses for invertebrates, mainly infecting insects and arthropods. A "recombinant baculovirus" has further introduced recombinant DNA through, for example, homologous recombination or transposition. The recombinant baculovirus preferably originates from AcMNPV.

"Recombinant DNA" refers to a form of artificial DNA that is engineered through the combination or insertion of one or more DNA strands, thereby combining DNA that would normally not occur together.

"Recombinant DNA element" refers to a functional element within recombinant DNA, such as a promoter, enhancer or a gene. As mentioned above, the recombinant DNA elements of the present invention are sequences that cause the expression of baculovirus transcriptional regulators above endogenous levels, enhancer homologous regions (hr) and promoters operably linked to these aforementioned elements.

"Transcriptional regulator" refers to a regulatory protein that has the ability to modulate the transcription of specific genes by, for example, binding to enhancer or repressor regions and/or recruiting further proteins that are involved in transcription.

IE-1 and its splice variant IE-0 are transcriptional regulators that are endogenously expressed during baculovirus infection. According to the present invention, IE-1, IE-0 and/or fragments thereof are recombinantly expressed to increase the total level of these proteins above endogenous levels. This can be achieved through, for example, introducing further copies of the endogenous gene or manipulating the expression of the promoter of the endogenous gene. Further, copies of the endogenous genes can be introduced as transgenes under the control of a suitable promoter such as polh or $pB2_9$.

The expression level of the proteins IE-1, IE-0 and/or fragments thereof can be determined at both the mRNA and at the protein level with methods conventionally known to the person skilled in the art, such as quantitative PCR and Western Blot analysis.

According to the invention, IE-1, IE-0 and fragments thereof are encoded by the nucleic acids of SEQ ID NO: 2 (also referred to as Ac-ie-01) to SEQ ID NO: 5. SEQ ID NO: 3 is the Ac-ie-01 cDNA that encodes both IE-1 and IE-0, SEQ ID NO: 2 is the coding sequence (CDS) of IE-1 and SEQ ID NO: 3 is the CDS of IE-0. SEQ ID NO: 4 and 5 are the CDSs of the N-terminal domains of IE-1 and IE-0 respectively that retain the catalytic transcriptional regulator activity. The proteins that are encoded by SEQ ID NO: 2-5 are represented by SEQ ID NO: 6-9 respectively.

The present invention furthermore discloses variants of SEQ ID NO: 2-9 that are or encode amino acids that are able to function as a transcriptional regulator. These variants are nucleic or amino acids whose nucleotide or amino acid sequence differs in one or more positions from these parental nucleic or amino acids, whereby differences might be additions, deletions and/or substitutions of nucleotides or amino acid residues.

Nucleic and amino acid sequences of the present invention shall be distinguished from other nucleic and amino acid sequences by their degree of sequence identity or similarity respectively as determined using EMBOSS Needle with the default parameters. Methods for the generation of such variants include random or site directed mutagenesis, site-saturation mutagenesis, PCR-based fragment assembly, DNA shuffling, homologous recombination in vitro or in vivo, and methods of gene-synthesis.

The sequence of the variants of SEQ ID NO: 2-5 is at least 70%, preferably at least 75%, more preferably at least 80%, more preferably at least 85%, more preferably at least 90% and most preferably at least 95% identical to the sequences of SEQ ID NO: 2-5.

The sequence of the variants of SEQ ID NO: 6-9 is at least 70%, preferably at least 75%, more preferably at least 80%, more preferably at least 85%, more preferably at least 90% and most preferably at least 95% similar to the sequences of SEQ ID NO: 6-9.

In a preferred embodiment, the recombinant baculovirus of the present invention further contains, in addition to the nucleic acid sequence that allows for the expression above endogenous levels of the proteins IE-1, IE-0 and/or fragments thereof, a recombinant homologous region (hr) that can enhance the expression of a recombinant protein by being operably linked to the respective promoter.

Homologous regions, hr, are comprised of repeated units of about 70-bp with an imperfect 30-bp palindrome near their center, Homologous regions are repeated at eight locations in the AcMNPV genome with 2 to 8 repeats at each side. Homologous regions have been implicated as both transcriptional enhancers and origins of baculovirus DNA replication.

"Enhancer region" refers to a control sequence, whose binding by transcriptional regulators increases the level of transcription of associated genes.

"Recombinant protein" refers to a protein that originates from recombinant DNA. Such proteins can be used for the benefit of humans and animals and may have industrial, commercial or therapeutic application.

"Being operably linked" refers to two nucleic acid sequences that are connected in a way that one influences the other in terms of, for example, transcriptional regulation.

"Promoter" refers to a DNA sequence to which RNA polymerase can bind to initiate transcription. The sequence may further contain binding sites for various proteins that regulate transcription, such as transcription factors. The promoter sequence may be composed of different promoter fragments (either different or the same fragments) that are localized closely in the DNA sequence and may be separated by linkers or spacer. Such promoters are referred to as chimeric promoters.

The enhancer homologous region sequence hr upstream of the promoter/s is preferably hr1 (SEQ ID NO: 27). The promoters that drive the expression of the recombinant protein are preferably selected from the group comprising SEQ ID NO: 1046 or a sequence that is able to function as a promoter and has at least 70%, preferably at least 75%, more preferably at least 80%, more preferably at least 85%, more preferably at least 90% and most preferably at least 95% identity with the nucleotide sequence indicated in any of SEQ ID NO: 10-16.

In a preferred embodiment, the nucleic acid sequence comprises combinations of recombinant promoters, sequences encoding transcriptional regulators and enhancer regions selected from the group comprising SEQ ID NO: 17-26.

As indicated above, the recombinant promoters, sequences encoding transcriptional regulators and enhancer regions of the present invention do not need to form part of a single molecule, instead these sequences may form part of distinct molecules as long as they are operably linked, i.e. contained within the same cells.

The recombinant baculovirus of the present invention preferably comprises a nucleic acid sequence encoding a recombinant protein. This nucleic acid sequence is operably linked to the nucleic acid sequence that allows for the expression above endogenous levels of the proteins IE-1, IE-0 and/or fragments thereof and optionally to a homologous region (hr).

In one embodiment, the present invention discloses a host cell that is infected, transfected, transduced or transformed with the recombinant baculovirus, transfer vector, cloning vector or nucleic acid sequence of the present invention. Preferably, the host cell is kept in cell culture. The host cell is preferably an insect cell line, more preferably a cell line derived from an insect belonging to the *Lepidoptera* or *Diptera* genus, more preferably the host cell is derived from the group consisting of *Trichoplusia ni, Spodoptera frugiperda, Ascalapha odorata, Bombyx mori, Drosophila melanogaster* and *Aedes aegypti* and most preferably it is selected from the group of insect cell lines consisting of Hi-5™, Sf9, Sf21, BTI-Tn5B-1, Tn368, ExpresSf+®, BTI-TnAo38, ATC-10 and Schneider's *Drosophila* Line 2. The host cell may be cultured in monolayer or in suspension.

In a further aspect the invention discloses methods for producing a recombinant protein using the host cell of the invention. After expression of the recombinant protein, extraction and purification of the recombinant protein is done by conventional means.

In a preferred embodiment for protein production, the host cells are cultured in suspension (bioreactors), at densities between $2 \times 10^6$ to $8 \times 10^6$ cells per ml, depending on the cell line and the fermentation procedure used. Furthermore, cells are infected at a MOI of 0.1 to 1.

The recombinant protein that is preferably produced by the methods of the present invention is a protein selected from the group comprising subunit monomeric vaccine, subunit multimeric vaccine, virus like particle, therapeutic protein, antibody, enzyme, cytokine, blood clotting factor, anticoagulant, receptor, hormone and diagnostic protein reagent.

One aspect of the invention relates to the use of the recombinant baculovirus, transfer vector, cloning vector or nucleic acid sequence of the present invention in a culture medium. In a preferred embodiment the culture medium comprises a baculovirus of the present invention.

The present invention discloses a transfer vector that can be used to produce the recombinant baculovirus of the present invention and comprises said sequence for expression above endogenous levels of the proteins IE-0, IE-1 and/or fragments thereof, in addition to a sequence suitable for integration or transposition in a baculovirus.

Transfer vectors generally permit the insertion of genetic information into a baculovirus.

The transfer vector preferably contains in addition to (i) the sequence for expression above endogenous levels of the proteins IE-0, IE-1 and/or fragments thereof, (ii) a recombinant homologous region (hr) linked to (iii) a suitable promoter for driving the expression of a recombinant protein. The preferred combinations of these recombinant DNA elements are as described above for the recombinant baculovirus.

In one preferred aspect, the transfer vector comprises a nucleic acid sequence encoding said recombinant protein, whereas in another preferred embodiment the transfer vector lacks such sequence.

In a preferred embodiment, the transfer vector is a bacmid.

"Bacmid" refers to a plasmid construct which contains the DNA sequence sufficient for generating a baculovirus when transfected into a cell.

In a further preferred embodiment, the transfer vector is derived from any of the commercially available baculovirus expression systems "Bac-to-Bac®" (Invitrogen™), "BacPAK™" (Clontech™), "FlashBAC™" (Oxford Expression Technologies™), "BacuVance™" (GenScript™), "Bac-N-Blue DNA™" (Invitrogen™), "BaculoDirect™" (Invitrogen™), "BacVector®" 1000, 2000, 3000 (Novagen®), "DiamondBac™" (SigmaAldrich®) or "BaculoGold™" (BD Biosciences™).

The present invention discloses a cloning vector that can be used to produce the recombinant baculovirus and/or transfer vector of the present invention and comprises said sequence for expression above endogenous levels of the proteins IE-0, IE-1 and/or fragments thereof, which is further suitable for bacterial replication.

"Cloning vector" refers to any vector that is suitable for cloning, which generally involves the presence of restriction sites, an origin of replication for bacterial propagation and a selectable marker.

The cloning vector preferably contains in addition to (i) the sequence for expression above endogenous levels of the proteins IE-0, IE-1 and/or fragments thereof, (ii) a recombinant homologous region (hr) linked to (iii) a suitable promoter for driving the expression of a recombinant protein. The preferred combinations of these recombinant DNA elements are as described above for the recombinant baculovirus.

In one preferred aspect, the cloning vector comprises a nucleic acid sequence encoding said recombinant protein (also referred to as the "donor vector"), whereas in another preferred embodiment the cloning vector lacks such sequence.

The present invention discloses a nucleic acid sequence that can be used to produce the recombinant baculovirus, transfer vector and/or cloning vector of the present invention and comprises said sequence for expression above endogenous levels of the proteins IE-0, IE-1 and/or fragments thereof.

The nucleic acid sequence preferably contains in addition to (i) the sequence for expression above endogenous levels of the proteins IE-0, IE-1 and/or fragments thereof, (ii) a recombinant homologous region (hr) linked to (iii) a suitable promoter for driving the expression of a recombinant protein. The preferred combinations of these recombinant DNA elements are as described above for the recombinant baculovirus.

In one preferred aspect, the nucleic acid sequence comprises a nucleic acid sequence encoding said recombinant protein, whereas in another preferred embodiment the nucleic acid sequence lacks such sequence.

The transient expression of the Ac-ie-01 cDNA by a baculovirus system surprisingly confers unique properties of virus resistance and cell proliferation to the cells. This suggests that the overexpression of the transcriptional regulators encoded by this gene activates other virus or cellular genes which may be responsible for such interesting biotechnology applications related to the productivity increase and resistance to different cellular stresses. A potential application derived from this study could be the generation of insect, avian or mammalian transgenic cells which may represent highly productive cell lines to be used for recombinant protein production or virus propagation with potential use in the production of conventional vaccines based on attenuated or inactivated viruses.

Hence, one aspect of the invention relates to a transgenic cell line that carries as a transgene the sequences of SEQ ID NO: 2-5 or variants thereof or sequences that encode the proteins of SEQ ID NO: 6-9 or variants thereof as defined above. The transgenic cell line is preferably of mammalian, avian or insect origin. In a further embodiment, the transgenic cell line of the invention can be used for the production of a recombinant protein, which is extracted and purified by conventional means.

"Transgenic cell line" refers to a cell line that contains a gene that was transferred into the cell.

Based on the surprising finding that the recombinant baculovirus promoter pB2$_9$ (SEQ ID NO: 14) and the chimeric recombinant baculovirus promoters pB2$_9$p10 (SEQ ID NO: 12) and pB2p10 (SEQ ID NO: 15) allow an improved expression as compared to conventional promoters, such as pB2, a further aspect of the present invention relates to nucleic acid sequences comprising such sequence or sequence variants of SEQ ID NO: 12, 14 or 15 that are at least 70%, preferably at least 75%, more preferably at least 80%, more preferably at least 85%, more preferably at least 90% and most preferably at least 95% identical to the sequences of SEQ ID NO: 12, 14 or 15.

Summary of Sequences

| SEQ ID NO: | Name: |
|---|---|
| 1 | Complete Ac-ie-01 cDNA |
| 2 | Protein coding sequence (CDS) of IE-1 |
| 3 | CDS of IE-0 |
| 4 | CDS of the IE-1 N-terminal domain |
| 5 | CDS of the IE-0 N-terminal domain |
| 6 | IE-1 protein |
| 7 | IE-0 protein |
| 8 | IE-1 N-terminal domain protein |
| 9 | IE-0 N-terminal domain protein |
| 10 | polh (promoter) |
| 11 | p10 (promoter) |
| 12 | pB2$_9$p10 (promoter) |
| 13 | p6.9p10 (promoter) |
| 14 | pB2$_9$ (promoter) |
| 15 | pB2p10 (promoter) |
| 16 | polhp10 (promoter) |
| 17 | polhAc-ie-01/hr1p10 |
| 18 | polhAc-ie-01/hr1pB2$_9$p10 |
| 19 | polhAc-ie-01/hr1p6.9p10 |
| 20 | pB2$_9$Ac-ie-01/hr1p10 |
| 21 | pB2$_9$Ac-ie-01/hr1pB2$_9$p10 |
| 22 | pB2$_9$Ac-ie-01/hr1p6.9p10 |
| 23 | polhAc-ie-01/hr1polh |
| 24 | pB2$_9$Ac-ie-01/hr1polh |
| 25 | polhAc-ie-01/hr1polhp10 |
| 26 | pB2$_9$Ac-ie-01/hr1polhp10 |
| 27 | Homologous region enhancer hr1 |
| 28 | polhAC-ie-01 |

-continued

| SEQ ID NO: | Name: |
|---|---|
| 29 | polhGFP |
| 30 | p10pB2 (promoter) |
| 31 | polhpB2 (promoter) |
| 32 | pB2polh (promoter) |
| 33 | pB2$_9$polh (promoter) |
| 34 | pB2 (promoter) |
| 35 | hr1polhpB2 |
| 36 | hr1pB2polh |
| 37 | hr1p10pB2 |
| 38 | hr1pB2p10 |
| 39 | hr1pB2$_9$polh |
| 40 | hr1pB2$_9$p10 |

Deposition of Microorganisms According to the Budapest Treaty

Plasmids were deposited in the Spanish Type Culture Collection (CECT) (www.cect.org); University of Valencia, Parc Cientific Universitat de València; Catedrático Agustín Escardino, 9; 46980 Paterna (Valencia), Spain, with the accession number CECT 8031, on the date Oct. 4, 2011.

EXAMPLES

Example 1

Overexpression of Baculovirus Transcriptional Regulators Potentiates the Enhancer Function of a Homologous Region hr Functionally Linked to a Promoter Increasing the Expression of a Recombinant Protein in a Baculovirus Vector Expression System (BEVS)

Immediate early viral proteins encoded by the Ac-ie-01 cDNA, i.e. IE-1 and IE-0, from AcMNPV are potent transcriptional regulators in the baculovirus. Transactivation mediated by these proteins is enhanced by their binding as a homodimer to the baculovirus homologous region (hr) sequences, which act as transcriptional enhancers. AcMNPV IE-1/IE-0 are 67-72 kDa dimeric DNA-binding proteins that stimulate transcription in plasmid transfection assays through the activity of its N-terminal acidic domain (7, 8). Synthesized very early during infection, IE-1 and IE-0 accumulate within the nucleus, where they are maintained through late times. Using the dual plasmid pFastBac™ (Invitrogen™), the Ac-ie-01 cDNA was cloned under the control of the polh promoter. In the same plasmid, but in another locus, the GFP encoding gene was cloned downstream of the hr1pB2$_9$p10 chimeric promoter that was previously synthesized and contains the homologous region hr1 fused to the promoters pB2$_9$ and p10. Promoter pB2$_9$ is a DNA fragment derived from the promoter pB2 which drives the expression of the Basic juvenile hormone-suppressible protein 2 (BJHSP-2) in *T. ni* lepidopter. Fragment pB2$_9$, comprising a sequence consisting of 436 nucleotides derived from the pB2 promoter, showing higher expression levels than the full-length insect-derived promoter when incorporated into a baculovirus expression vector. A schematic representation of the resulting baculovirus expression cassette of the present invention and the putative function of the recombinant DNA elements is shown in FIG. 1. The resulting plasmid was used to generate a recombinant baculovirus by the "Bac-to-Bac®" system (Invitrogen™). In parallel, a conventional baculovirus expressing the GFP protein under the control of polh promoter was generated by the same system.

Figure 4:
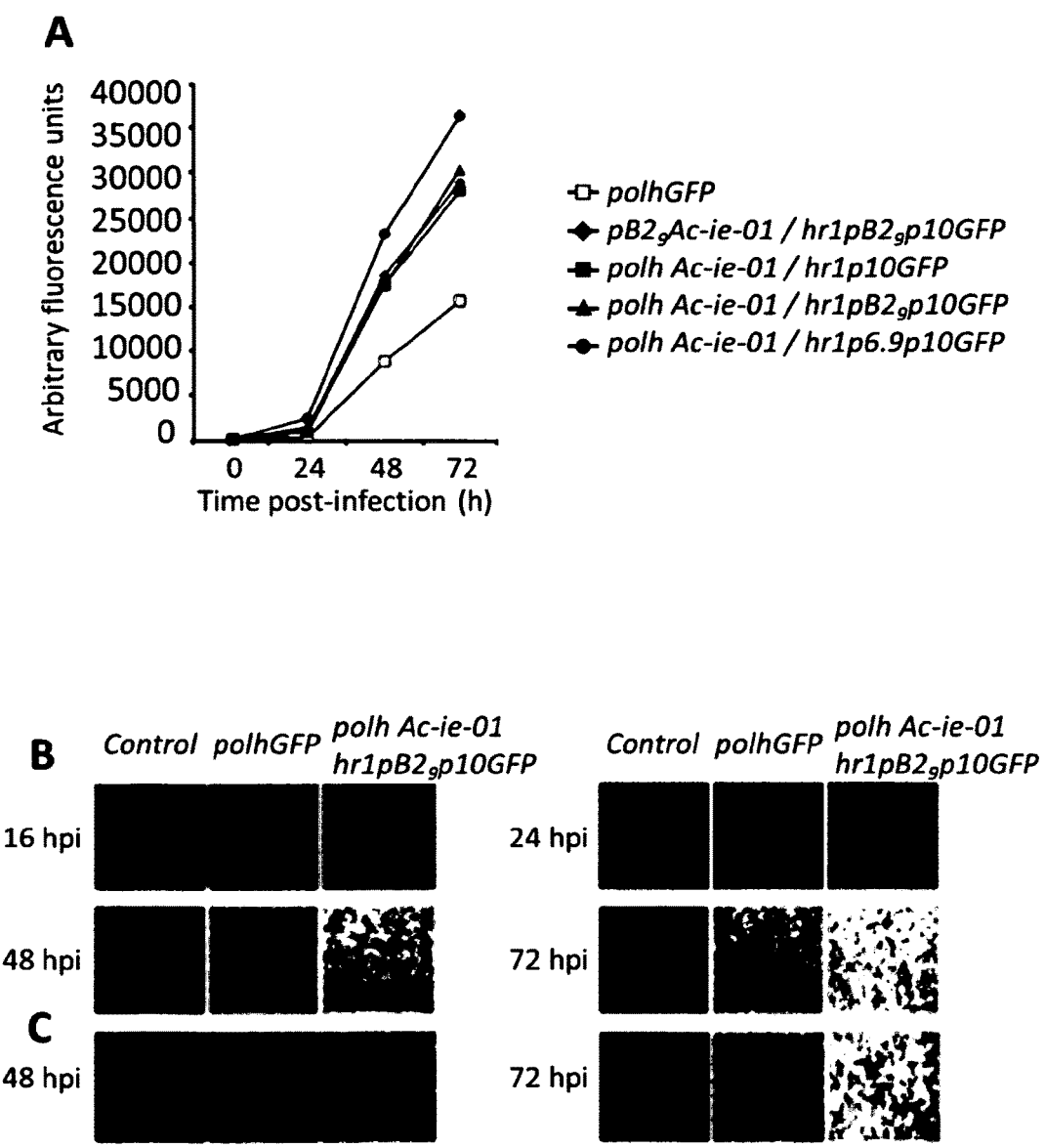
FIG. 4: A) Fluorimetric assays for the measurement of the increment in GFP protein accumulated in infected Sf21 cells at different times post-infection when expressed in the baculovirus expression cassettes of the invention, containing hr1p10, hr1pB2$_9$p10 or hr1p6.9p10 and the Ac-ie-01 cDNA expressed under the control of pB2$_9$ or polh promoters. All GFP expression levels were compared to that obtained with the polh promoter in a conventional baculovirus vector. The graph represents the mean values of three independent expression experiments for each baculovirus with standard deviations lower than 5% in each case. This figure also shows representative fluorescence micrographs showing Sf21 cells at different times post-infection with a wild-type baculovirus (control), with a conventional baculovirus expressing the GFP under the control of polh promoter or with a baculovirus expressing the GFP by the expression cassette of the invention polhAc-ie-01/hr1pB2$_9$p10GFP. Cells were infected in A) and B) at a multiplicity of infection (MOI) of 5 or in C) at a MOI of 0.1.

The expression of GFP protein mediated by the different baculoviruses was studied by fluorimetry at different times post-infection in Sf21 cells cultured in monolayer. Compared to a conventional baculovirus expressing the protein under the control of the polh promoter, the expression level of GFP was about 2 times higher with the baculovirus expression cassette containing the transcriptional regulators and enhancer sequence when used at a MOI of 5 (FIG. 4A) and 4 times higher when used at a MOI of 0.1 (data not shown). These differences in protein accumulation were also observed in Hi-5™ cells (data not shown), suggesting that the baculovirus expression cassette of the invention could be used to produce recombinant proteins in different insect cell lines used in research and industry.

Importantly, in infected cells observed by fluorescence microscopy, the GFP expression mediated by the baculovirus expression cassette of the present invention was detected earlier than when the conventional promoter polh was used for driving GFP expression and, moreover, the fluorescence intensity of infected cells was significantly higher (FIG. 4B). Fluorescent cells were detected as early as 16 hours post-infection when infected at a MOI of 5 with the recombinant baculovirus containing the expression cassette of the invention, and said GFP expression was increasing along the time of infection (FIG. 4B). These marked differences among novel and control recombinant baculoviruses were also observed at a low MOI of 0.1 (FIG. 4C).

To analyze the influence of the promoter used for the overexpression of the transcriptional regulators, the Ac-ie-01 cDNA was also cloned in the expression cassette described above under the control of pB2$_9$ promoter in substitution of the polh promoter. Independently of the promoter used to drive the Ac-ie-01 cDNA expression, the GFP accumulation was higher than the one observed when using a conventional baculovirus in which the reporter protein was expressed under the control of the polh promoter without Ac-ie-01 and hr1 elements in the expression cassette (FIG. 4A). In a similar way, the absence of Ac-ie-01 cDNA in an expression cassette containing the hr1 enhancer linked to pB2$_9$p10 chimeric promoter also resulted in lower expression levels of the GFP with respect to that containing the Ac-ie-01 cDNA (data not shown).

Example 2

Transcriptional Regulators Encoded by Ac-ie-01 cDNA Potentiate Other hr1 cis-Linked Baculovirus Promoters To analyze if transcriptional regulators encoded by Ac-ie-01 in combination with an enhancer sequence increase the expression mediated by other baculovirus promoters, chimeric or not (p6.9p10 or p10), cis-linked to the transcription enhancer homologous region 1 (hr1), we generated a new set of baculovirus expression cassettes and their corresponding AcMNPV recombinant baculoviruses. These expression cassettes contained the Ac-ie-01 cDNA cloned under the control of the polh promoter and the GFP encoding gene downstream of the hr1p10 or hr1p6.9p10 promoters. The expression levels were measured by fluorimetric analysis of extracts from insect cells infected with the different baculoviruses. As a control, the conventional recombinant baculovirus expressing the GFP protein under the control of polh promoter was used. The results observed demonstrated that transcriptional regulators encoded by Ac-ie-01 cDNA in combination with a homologous sequence hr1 were also able to promote unprecedented expression levels of the reporter protein GFP expressed under the control of other baculovirus promoters or combination of promoters (chimeric) (FIG. 4A). In the case of the expression cassette using the chimeric promoter composed of p6.9 and p10, the recombinant protein production was the highest among different recombinant baculoviruses assayed (about 2.5 times higher compared to the control at 72 hours post-infection).

Figure 5:
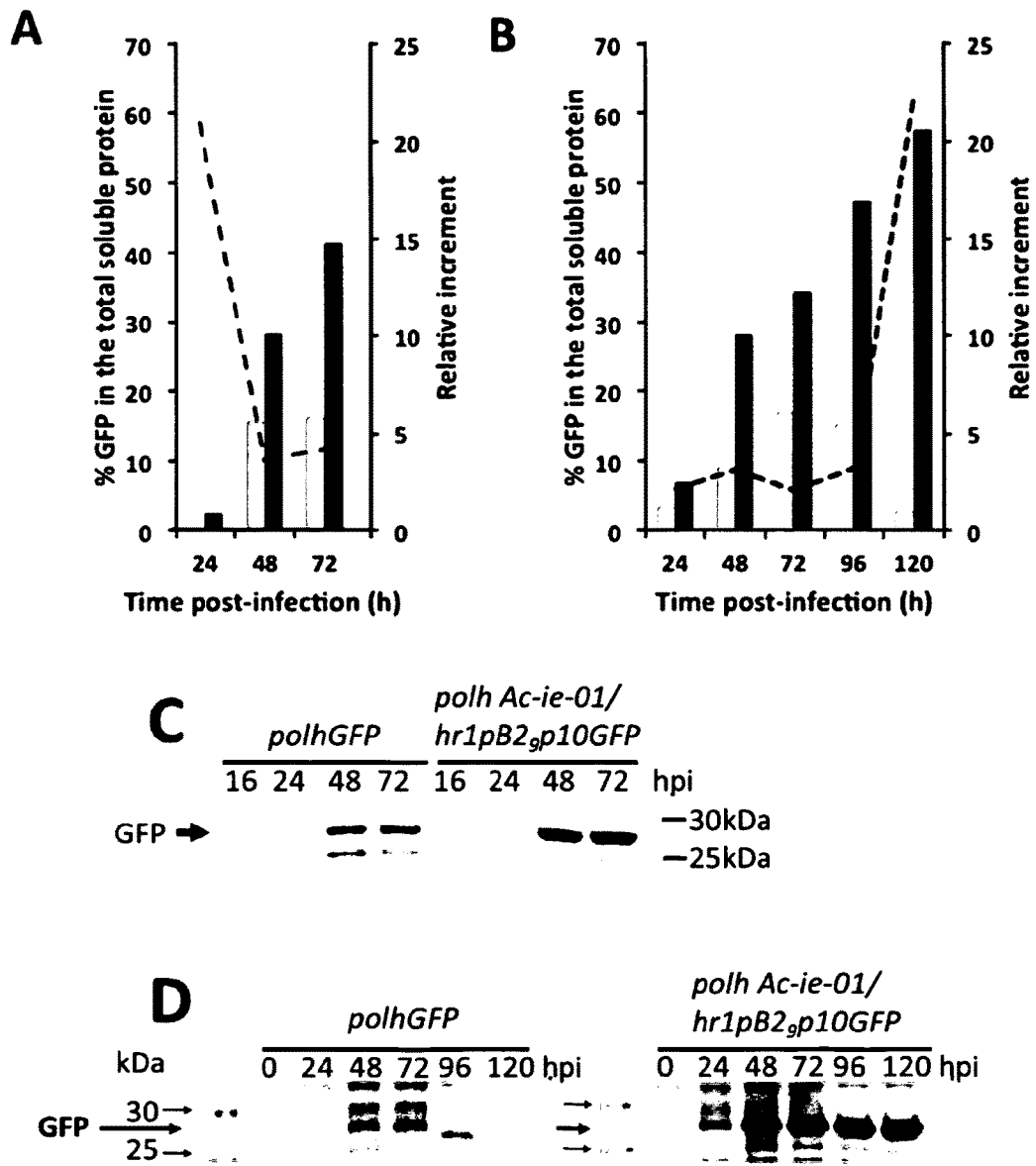
FIG. 5: A) Comparison of the amounts of recombinant GFP protein in Sf21 insect cells grown in monolayer at different times post-infection expressed by a conventional baculovirus vector under the control of a polh promoter (light grey) or by the baculovirus vector engineered with an expression cassette of the invention, composed of the elements polhAc-ie-01/hr1pB2$_9$p10GFP (dark grey) and measured by microfluidic protein analysis (Experion™; Bio-Rad™, USA). Cells were infected at a MOI of 5 with both viruses; B) Comparison of recombinant GFP protein accumulated in Sf9 insect cells grown in suspension at different times post-infection expressed by a conventional baculovirus vector under the control of a polh promoter (light grey) or by the baculovirus vector engineered with an expression cassette of the invention, composed of the elements polhAc-ie-01/hr1p6.p10GFP (dark grey) and measured by microfluidic protein analysis (Experion™; BioRad™, USA). Cells were infected at a MOI of 0.1 with both viruses; Discontinued lines indicate the percentage of increment of recombinant GFP produced by the baculoviruses containing the expression cassette of the invention in comparison to that obtained with the conventional baculovirus expressing the GFP under the control of the polh promoter; C) Coomassie blue staining of SDS-PAGE gels resolving the infected cell extracts of the experiment described in panel A; D) Coomassie blue staining of SDS-PAGE gels resolving the infected cell extracts of the experiment described in panel B.

A further quantification of the GFP production in both 5121 insect cells in monolayer and Sf9 insect cells in suspension mediated by a conventional baculovirus or by a baculovirus incorporating the expression cassette of the present invention containing the elements polhAc-ie-01/hr1pB2$_9$p10GFP, was carried out by microfluidic protein analysis (Experion™; BioRad™, USA). Insect cells in monolayer were infected at a high MOI of 5 and in suspension at a low MOI of 0.1. FIG. 5A shows the percentages of recombinant GFP produced with respect to the total soluble cell proteins at different times post-infection (24 to 72 hours) and the relative increases of productivity with respect to the conventional baculovirus. At the latest time analyzed, the baculovirus containing the expression cassette of the invention reached levels of the recombinant GFP of more than 40% of the total cellular protein. Significant differences in the GFP band intensities between the assayed baculoviruses were visible in a Coomassie blue stained SDS-PAGE gel in which cellular extracts from infected cells were resolved (FIG. 5C). When insect cells were cultured in suspension and infected with each baculovirus, differences in recombinant protein productivity were even higher than those detected in insect cells cultured in monolayer and infected at a high MOI of 5. FIG. 5B shows such differences found in GFP production between 24 to 120 hours post-infection. Interestingly, when the baculovirus incorporating the expression cassette of the invention was used, recombinant protein productivity increased along time, reaching maximum levels at 120 hours post-infection. In contrast, the recombinant protein produced by a conventional baculovirus reached maximum levels at 72 hours post-infection decreasing at later times post-infection (FIG. 5B). An increase of productivity of more than 20 times was observed with the baculovirus expression cassette of the present invention at very late times post-infection. Similar results were observed in Hi-5™ cells (data not shown), demonstrating that the expression cassette of the invention can be employed to produce recombinant proteins in different insect cell lines used in research and industry. Significant differences in the GFP band intensities between the assayed baculoviruses from cells cultured in suspension were also visible in a Coomassie blue stained SDS-PAGE gel in which cellular extracts from infected cells were resolved (FIG. 5D).

Example 3

The Baculovirus Expression Cassettes of the Invention Induce Cell Proliferation and Increase Cell Viability Through the Transcriptional Regulators Encoded by the Ac-ie-01 cDNA We observed by microscopy that recombinant baculoviruses incorporating the baculovirus expression cassettes of the invention have interesting properties related to a decrease in the virus-induced cytopathic effects and an increase of the cell density in cultures. To quantify these phenomena and to determine the DNA element/s responsible for such interesting properties, we generated a recombinant baculovirus expressing the transcriptional regulators encoded by the Ac-ie-01 cDNA under the control of polh promoter. This baculovirus jointly with a baculovirus incorporating the elements of expression cassette of the present invention used in example 2 (polhAc-ie-01/hr1p6.9p10GFP) and a conventional baculovirus expressing the GFP protein, were used to infect Sf9 cells in suspension at a low MOI of 0.1. The increase in cell number and cell viability was studied between 24 to 120 hours post-infection. At 24 hours post-infection, insect cells infected by any of the baculoviruses overexpressing the above mentioned transcriptional regulators presented an increase in cell number higher than 10% with respect to cultures infected by the control recombinant baculovirus (FIG. 6A). A more detailed analysis by flow cytometry of the time required for these factors to induce the observed differences in cell proliferation revealed an increase of insect cells in S phase at 3 hours post-infection and then at 6 hours post-infection, an increase in the number of insect cells in G1 was observed. These data imply a very early increment of the mitosis in those cultures infected by the baculovirus overexpressing the Ac-ie-01 cDNA encoding proteins (data not shown).

Fluorescence measurement was performed on a FACSCalibur™ (BD Biosciences™) flow cytometer. Cells were fixed in 70% EtOH, resuspended and incubated in the staining solution (50 µg/ml propidium iodide in PBS, 5 ug/ml RNAse). The data were gated to eliminate particles with a distinct size from cells and analyzed by plotting the cell number vs the red fluorescence from propidium iodide. 50,000 cells were counted per assay. Data analysis of the total number of cells per cell cycle phase (G1, S and G2) was made using Modfit software.

Infected cell cultures were also analyzed by Trypan blue staining to determine cell viability at different times post-infection. Interestingly, at very late times post-infection (96-120 hours), insect cells infected by the viruses overexpressing the transcriptional regulators showed an increase (50-60% increase) of cell viability and integrity (FIG. 6B). This suggests that the overexpression of the transcriptional regulators of the present invention protects the cells from the baculovirus-induced cytopathic effect, allowing long-term expression. Both cell proliferation and increased cell viability after infection have important consequences in the recombinant protein productivity of the BEVS. Similar results were obtained when the overexpression of the transcriptional regulators was driven by both the pB2$_9$ or polh promoters (data not shown). Results observed in Sf9 insect cells infected in suspension were confirmed in Sf21 cells cultured in monolayer (data not shown) and also in Hi-5™ cells cultured in monolayer (FIGS. 6C and D). These figures demonstrate how the overexpression of the transcriptional regulators improves the cell integrity at late times post-infection (96 hours).

Example 4

Figure 7:
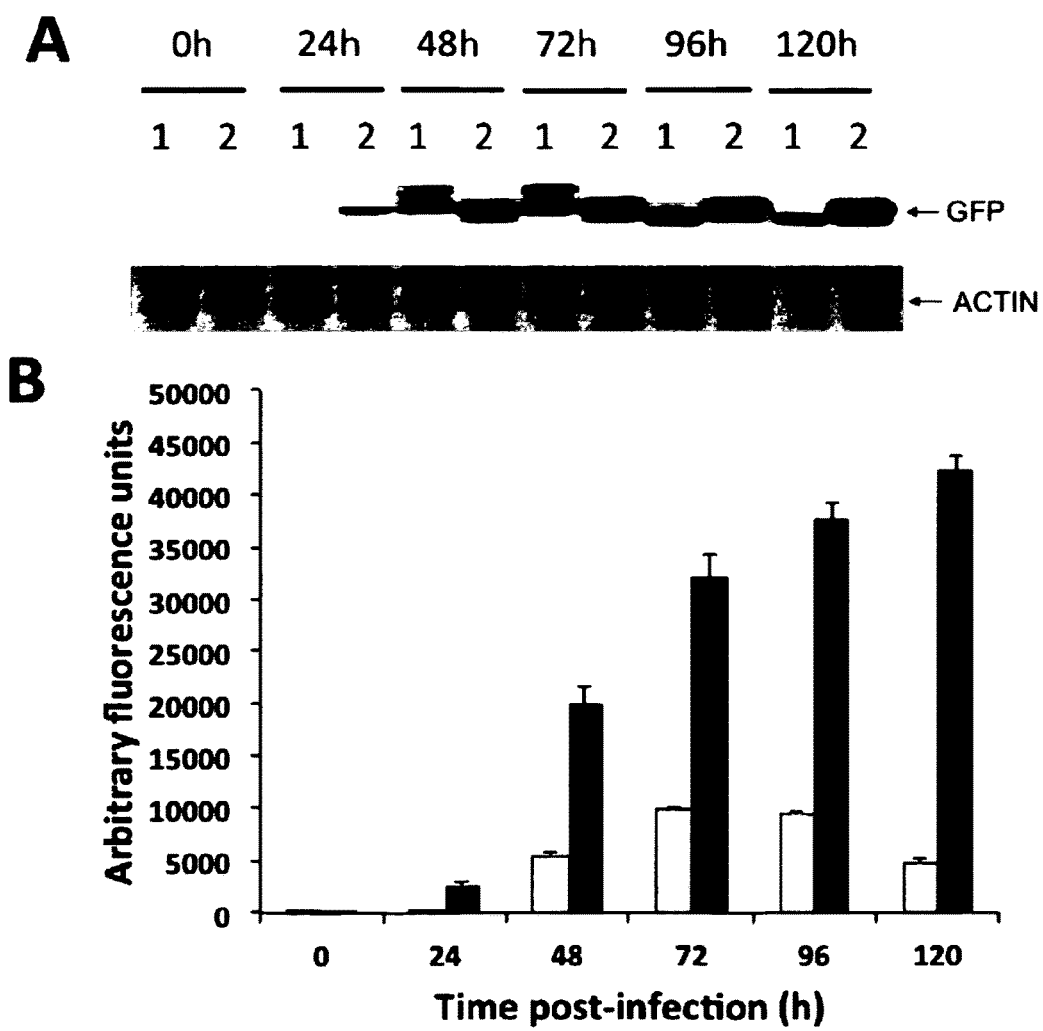
FIG. 7: A) Sf9 insect cells were infected by a conventional baculovirus expressing the GFP protein under the control of the polh promoter (1) or by a baculovirus vector engineered with the expression cassette of the invention containing the elements polhAc-ie-01/hr1p6.9p10GFP, overexpressing the transcriptional regulators encoded by Ac-ie-01 cDNA (2). Cells were sampled at different times post-infection (0 to 120 hours) and cell extracts analysed by SDS-PAGE and Western blot with an antiserum against GFP or against the cellular actin protein. B) The functionality of the GFP protein expressed in Sf9 insect cells as analyzed in panel A was measured by fluorimetry. The fluorescence values obtained at different hours post-infection with the GFP protein produced by a conventional recombinant baculovirus (grey bars) was compared to that produced by the recombinant baculovirus with the baculovirus cassette of the present invention (black bars).

Overexpression in a Baculovirus Expression System of Transcriptional Regulators Encoded by the Ac-ie-01 cDNA Facilitates the Post-Translational Processing of Recombinant Proteins Cellular integrity during baculovirus infection is of great importance to ascertain the correct folding or any other post-translational modification of foreign proteins expressed by this system. The baculovirus strong promoters commonly used for research and production, such as polh and p10, only express the foreign genes at late times post-infection when infected cells already show severe cytopathic effects and the cellular viability decreases. As described above, the overexpression of the transcriptional regulators used in the baculovirus expression cassette of the present invention protects cells from pathogenic effects of the baculovirus infection by a still unknown mechanism, allowing a wide temporal window for recombinant protein production in cells remaining fully viable. We studied the relevance of the elements incorporated into the expression cassette of the invention in relation to post-translational modifications of recombinant proteins. For this purpose, a conventional baculovirus expressing the reporter protein GFP under the control of the polh promoter and a baculovirus incorporating the baculovirus cassette of the present invention and also expressing the GFP protein (polhAc-ie-01/hr1p6.9p10GFP) were used to infect Sf9 insect cells in suspension at a MOI of 0.1. Infected cells were analysed at different times after infection by Western blot using an anti-GFP monoclonal antibody (mab2515; Millipore™) as shown in FIG. 7. Interestingly, GFP protein expressed by a conventional baculovirus showed several reactive bands at 48 and 72 hours post-infection (suggesting non-proper expression and/or folding of the protein) and at later times a band with a reduced molecular weight (lower than predicted) was observed (suggesting degradation) (FIG. 7A). In contrast, when the GFP protein expression was mediated by the baculovirus expression cassette of the invention, only one GFP band was observed at all times post-infection analyzed, showing the expected molecular weight of this protein (FIG. 7A). The expression of GFP by this vector was not significantly reduced at very late times post-infection (120 hours), confirming that the baculovirus expression cassette of the invention confers to baculovirus vectors interesting advantages for long-lasting expression.

In parallel, the integrity of the cell machinery was measured at different times post-infection by Western blot analysis of the cellular actin protein using a specific antiserum (FIG. 7A). Infection with a conventional baculovirus impaired severely the cell integrity at 72 hours post-infection since the actin band detected decreased dramatically after this time point (degradation as a result of a complete loss of cell integrity). Consistent with the cellular protection induced by the recombinant DNA elements contained in the baculovirus expression cassette of the invention, cellular actin was not equally affected in cells infected by the recombinant baculovirus engineered with the expression cassette.

Fluorescence activity of recombinant GFP expressed by the different baculoviruses reflects its correct conformation. As is shown in FIG. 7B, the GFP expressed in the context of the baculovirus expression cassettes of the invention keep an increased pattern of functionality along infection times. In contrast, the fluorescence of GFP expressed by a conventional baculovirus peaked at 72 hours post-infection and decreased at later times (FIG. 7B), in parallel to actin degradation (FIG. 7A) and the observed cell viability reduction (FIG. 6B).

Example 5

Cell Culture and Viruses

Figure 8:
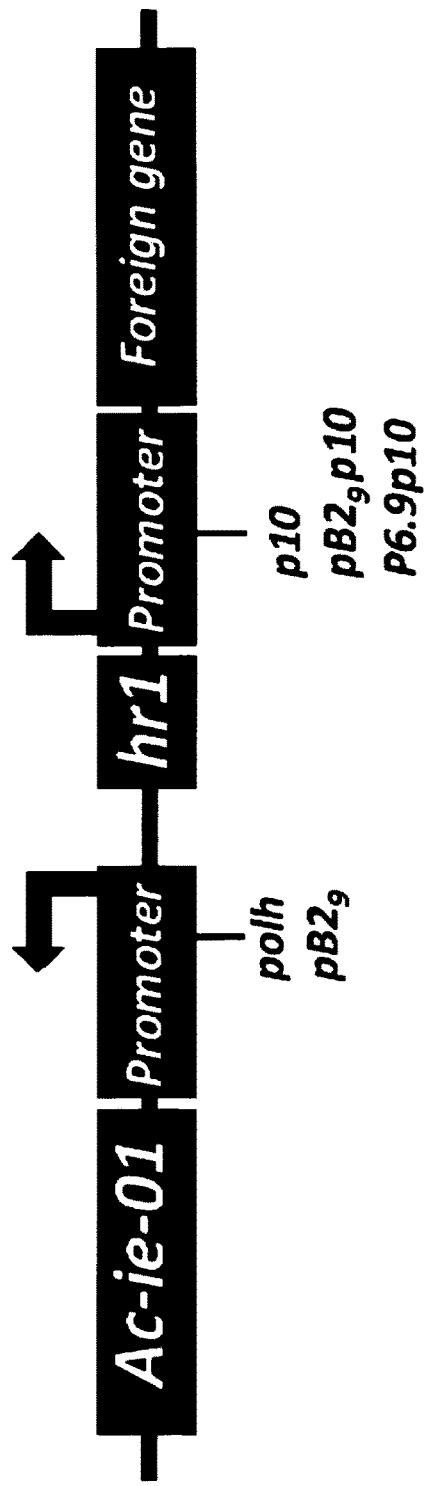
FIG. 8: Schematic representation of the preferred elements contained in the baculovirus expression cassettes of the invention, comprising encoding sequences for transcriptional regulators, homologous regions (hr) enhancing the transcription from promoter(s) of a foreign gene encoding a recombinant protein.

The *Spodoptera frugiperda* Sf21 or Sf9 cell lines were cultured in 6-well tissue culture plates (1×10⁶ cells/well) in TNM-FH insect medium (Pan Biotech™, Germany) containing 10% heat-inactivated fetal bovine serum (Pan Biotech™, Germany at 27° C. AcMNPV recombinant baculoviruses were obtained by the "Bac-to-Bac®" Baculovirus Expression System (Invitrogen™, USA), Different transfer vectors containing the recombinant DNA elements of the present invention were generated using the pFastBac™-DUAL plasmid (Invitrogen™). The promoters and regulatory elements incorporated into pFastBac™-DUAL were synthesized (GenScript™, USA) with the adequate flanking restriction sequences to facilitate the cloning. These transfer vectors were used to transfect Sf21 cells with Cellfectin® (Invitrogen™, USA). The resulting recombinant baculoviruses from the infection of Sf21 cells were then passaged twice in cells and titered by the plaque assay method. The obtained gene constructs of the baculovirus expression cassettes of the present invention are schematically shown in FIG. 8, showing different potential combinations of promoters driving the expression of the Ac-ie-01 cDNA or the foreign gene (e.g. GFP). The different expression cassettes were used to generate the recombinant baculoviruses used in the examples shown in FIGS. 4 to 7.

Example 6

Generation of the Cloning Vector

The cloning vector is a small piece of DNA containing the baculovirus expression cassette of the invention into which a foreign DNA fragment can be inserted by treating the vehicle and the foreign DNA with a restriction enzyme that creates the same overhang, then ligating the fragments together. The essential characteristics of the cloning vector must include a synthetic multiple cloning site (MCS) to facilitate the insertion of foreign genes directed in a chosen orientation, a selectable marker, such as an antibiotic resistance to allow the selection of positively transformed cells and a functional origin of replication (ORI) for propagation in bacteria.

Example 7

Generation of the Donor Vector Containing the Baculovirus Expression Cassette of the Invention A donor vector consists of a cloning vector, for example a pUC57 plasmid, containing the baculovirus expression cassette, into which a foreign gene has been cloned using the appropriate restriction enzymes. The baculovirus expression cassette of the invention was synthesized by ligating the following DNA sequences: (i) the baculovirus transcriptional regulator encoding sequence Ac-ie-01 downstream of a promoter sequence, such as the polh or the pB2$_9$ promoter, and upstream of the HSV TK polyadenylation signal and (ii) in another locus an enhancer sequence, for example, the homologous region hr1, upstream of (iii) a promoter sequence, for example, pB2$_9$p10, p10, p6.9p10 or polh, followed by a multiple cloning site (MCS) for cloning the gene of interest and the SV40 polyadenylation signal downstream of the MCS (FIG. 1). The baculovirus expression cassette is flanked by specific restriction sites (for example BglII and BstZ171 at the 5'-terminal end and Bgl II and Sgf I at the 3'-terminal end) to facilitate subcloning into a transfer vector of a commercial baculovirus generation system (based on transposition, for example the "Bac-to-Bac®" system (Invitrogen™), or based on homologous recombination, for example "flashBAC™" (Oxford Expression Technologies™), "Baculogold™" (130 Biosciences™), "BacPAK6™" (Clontech™), "Bac-N-Blue DNA™" (Invitrogen™) (FIGS. 2 and 3).

Figure 2:
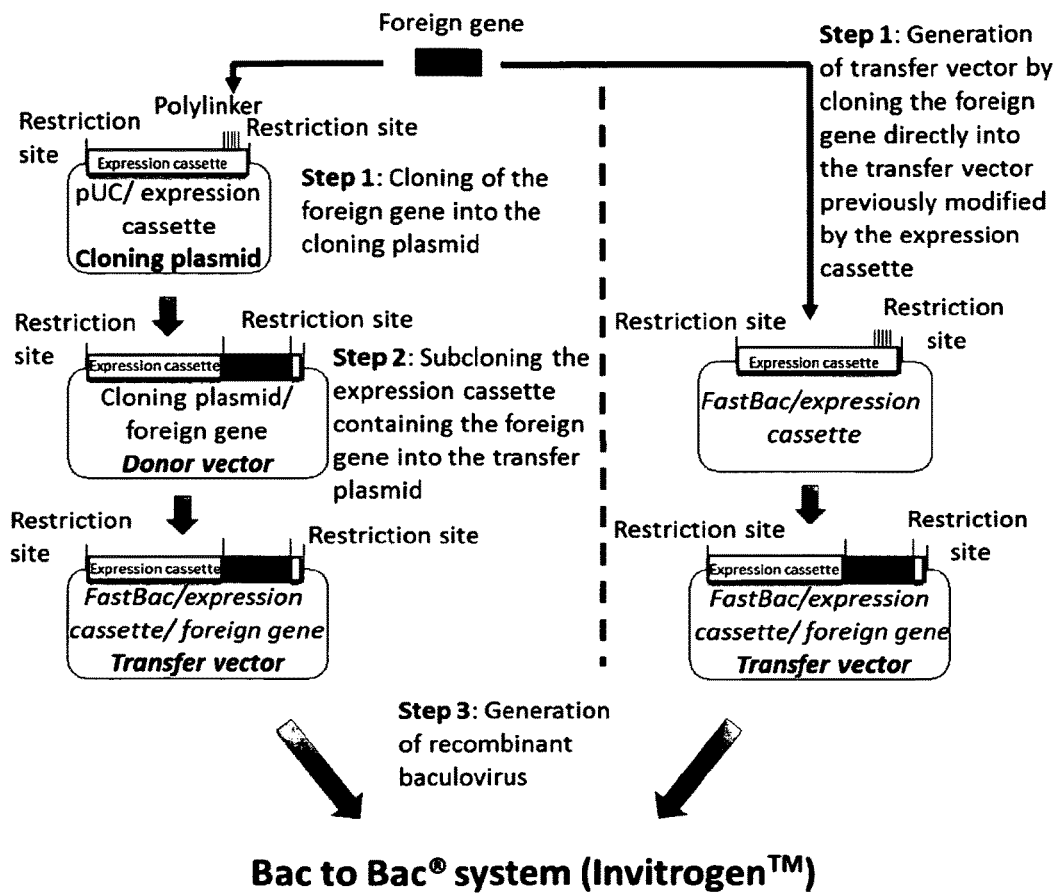
FIG. 2: Different strategies that result in the generation of recombinant baculoviruses by the "Bac-to-Bac®" cloning system (Invitrogen™).
Figure 3:
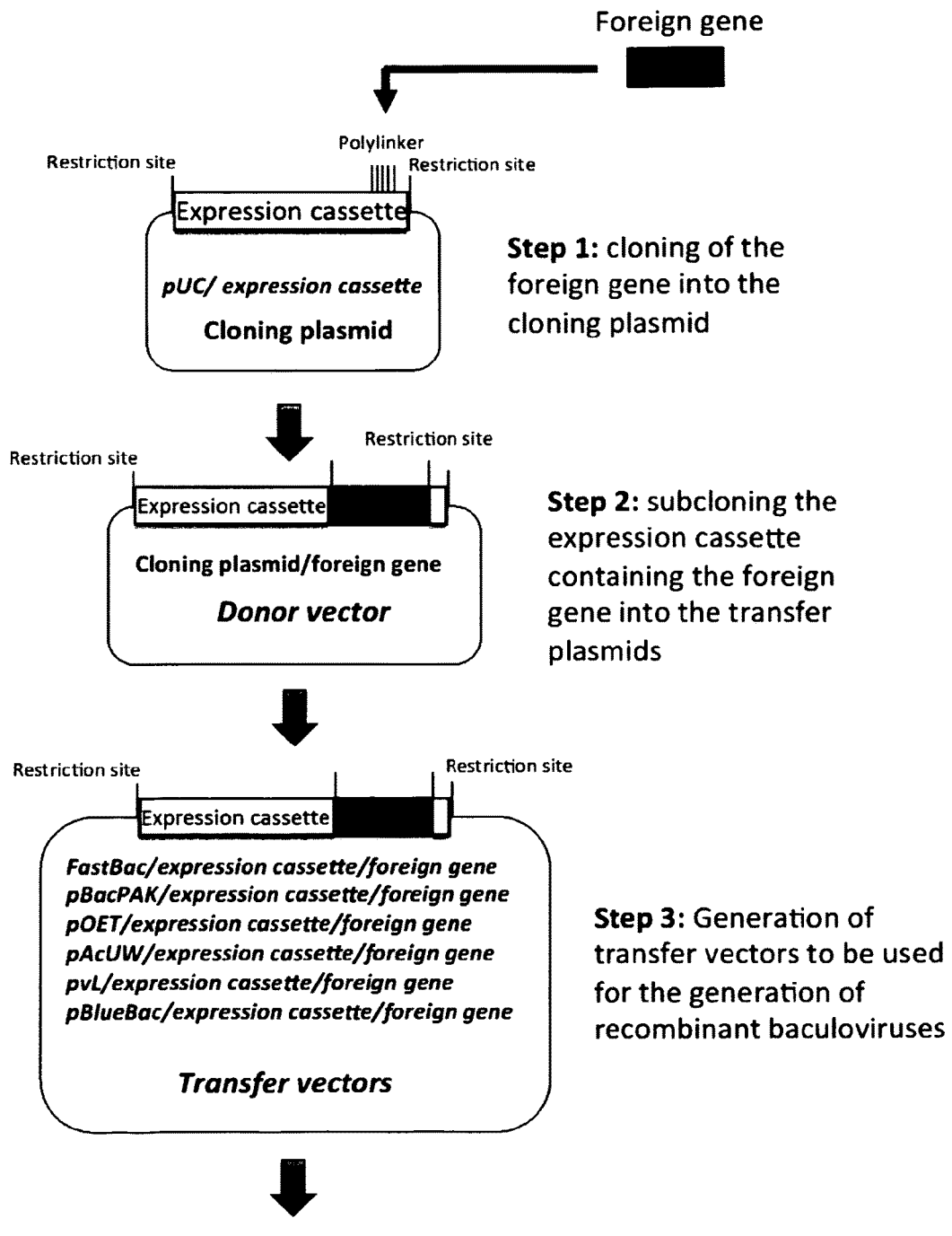
FIG. 3: General scheme for the generation of cloning, donor and transfer vectors compatible with other commercial technologies used to generate recombinant baculoviruses.

The encoding gene of the Green Fluorescence Protein (GFP) was cloned into the MCS of the cloning vector using the Nco I and Spe I restriction sites, generating the donor plasmid vector (FIG. 2).

Example 8

Generation of the Transfer Vector Containing the Baculovirus Expression Cassette of the Invention The transfer vector was generated by digesting a donor vector with BstZ17I of the 5'-flanking site and with Xba I and cloning it into the transfer vector pFastBac™1 that was also digested with the same enzymes. In this case, as a result of the subcloning, the SV40 polyadenylation signal of the baculovirus expression cassette is exchanged by the SV40 polyadenlation signal from the transfer vector. Apart from this, all the elements of the expression cassette are included in the pFastBac transfer vector, substituting the polh promoter and MCS of the original commercial transfer vector (FIG. 2).

Example 9

Generation of the Baculovirus Expression Vector Containing the Baculovirus Expression Cassette of the Present Invention Using the "Bac-to-Bac®" System The modified transfer vector pFastBac™1 and the individual baculovirus expression cassette were used to generate recombinant baculoviruses by using the "Bac-to-Bac®" Baculovirus Expression System. More specifically, the modified transfer vector was used to transform the *E. coli* host strain DH10Bac™ that contains a baculovirus shuttle vector (bacmid) and a helper plasmid, and allows the generation of the recombinant bacmid following transposition of the expression cassette. The DNA of the recombinant bacmid containing the baculovirus expression cassette of the present invention and the GFP encoding gene was then used to transfect insect cells, for example, Sf21 cells, using Cellfectin®. 72 hours post-transfection, cells were harvested and the first recombinant baculovirus generation was obtained (FIG. 2). This recombinant baculovirus could then be further amplified and/or titered following conventional protocols. Similar procedures can be used to generate recombinant baculoviruses with other transfer vectors provided by commercial BEVSs (FIG. 3).

Example 10

Protein Sample Preparation

Infected cells from each time point ($1\times10^6$) were harvested and centrifuged. The supernatants were removed and the cell pellets were resuspended in PBS and subjected to three cycles of freezing ($-196°$ C.) and thawing ($37°$ C.). Cellular debris was removed by centrifugation.

Example 11

Time-Course Study of Protein Expression

Sf9, Sf21 or Hi-5™ cells were infected with the different recombinant baculoviruses expressing GFP under the control of different combinations of regulatory, enhancer and promoter elements, using a MOI of 5 or 0.1. Cell cultures were harvested at various time points (24, 48, 72, 96 and 120 hours post-infection) and the GFP expression was analyzed by fluorescence microscopy, fluorimetric assay, SDS-PAGE followed by Coomassie blue staining or Western blot and by the microfluidic separation and quantification (Experion™ automated electrophoresis system; Bio-Rad™, USA).

For quantification of the recombinant GFP, samples were loaded in Pro260 chips (Bio-Rad™) and analyzed by capillary electrophoresis using the Experion™ system (Bio-Rad™), following the manufacturer's instructions. The electrophoresis of the samples was made through microchannels by controlling the applied voltage and electric power. The microfluidic chip allowed several sequential procedures including separation, staining, destaining, detection and basic data analysis without any need of user's intervention. The Experion™ system resolved and quantified protein samples from 10 to 260 kDa in size, with a high sensitivity, comparable to colloidal Coomassie blue SDS-PAGE gel staining. For quantification, the Experion™ system uses a Pro260 ladder, a modified version of the Precision Plus Protein™ standards, that have been optimized for use in that system.

Example 12

Fluorescence Microscopy Analysis

Infected cells were visualized directly in 6-well cell culture plates using a GFP filter on a Leica™ DMIL™ inverted fluorescence microscope.

Example 13

Fluorimetric Analysis

About 20 μg of total soluble proteins derived from infected cells, containing different amounts of recombinant GFP protein, were analyzed and quantified by a Tecan™ GENios™ (CA, USA) fluorescence plate reader (excitation [Ex], 485/emission [Em], 535).

Example 14

Western Blot Analysis

Total soluble protein fractions (10 μg) from cells infected with the recombinant baculoviruses were resolved in 15% SDS-PAGE gels. Gels were stained by the Coomassie blue staining method or transferred to nitrocellulose membranes. Western blots were probed with the anti-GFP monoclonal antibody mab2515 (Millipore™, USA) at 1:1000 or actin antiserum (20-33; SigmaAldrich™) and the immunocomplexes were revealed with anti-mouse IgG-horseradish peroxidase (HRP)-labeled conjugate (KPL™, UK), diluted 1:2,000 or by an anti-rabbit IgG-horseradish peroxidase (HRP)-labeled conjugate (KPL™, UK), diluted 1:2,000 respectively as a secondary antibody. Protein bands were detected using an ECL western blotting detection system and analyzed by the ChemiDoc™ XRS Gel Imaging System (Bio-Rad™, USA).

Example 15

Delimitation of Promoter Sequence in the pB2 DNA Fragment

The DNA region upstream of the BJHSP-2 gene (pB2) was PCR amplified from *T. ni* insect DNA based on the previously reported BJHSP2 sequence (GenBank accession no U41640). The amplified DNA region differed in several aspects from the annotated sequence, comprising 2 insertions, 8 deletions as well as 17 mutations (SEQ ID NO: 34). Using different bioinformatic analyses, six putative binding sites related to hormone-response elements were found along the pB2 sequence, four of them corresponding to putative ecdysone-response elements (EcR) and three of them to putative Broad-Complex sites (Br-C) (FIGS. 9A and B).

In order to determine essential regulatory regions for transcriptional activity and the relevance of potential hormone-regulated elements, a pB2 truncated sequence was analyzed (fragment pB2$_9$) (FIG. 9B). Both pB2 and pB2$_9$ fragments were cloned in a baculovirus vector and tested for their promoter activity by using the GFP reporter protein. FIG. 9B shows the GFP expression levels obtained with every fragment and quantified by a fluorimetric analysis. Surprisingly, the pB2$_9$ fragment showed a stronger promoter activity than the parental full-length pB2, even though it lacked two putative Br-C binding sites (FIG. 9B).

Example 16

Figure 10:
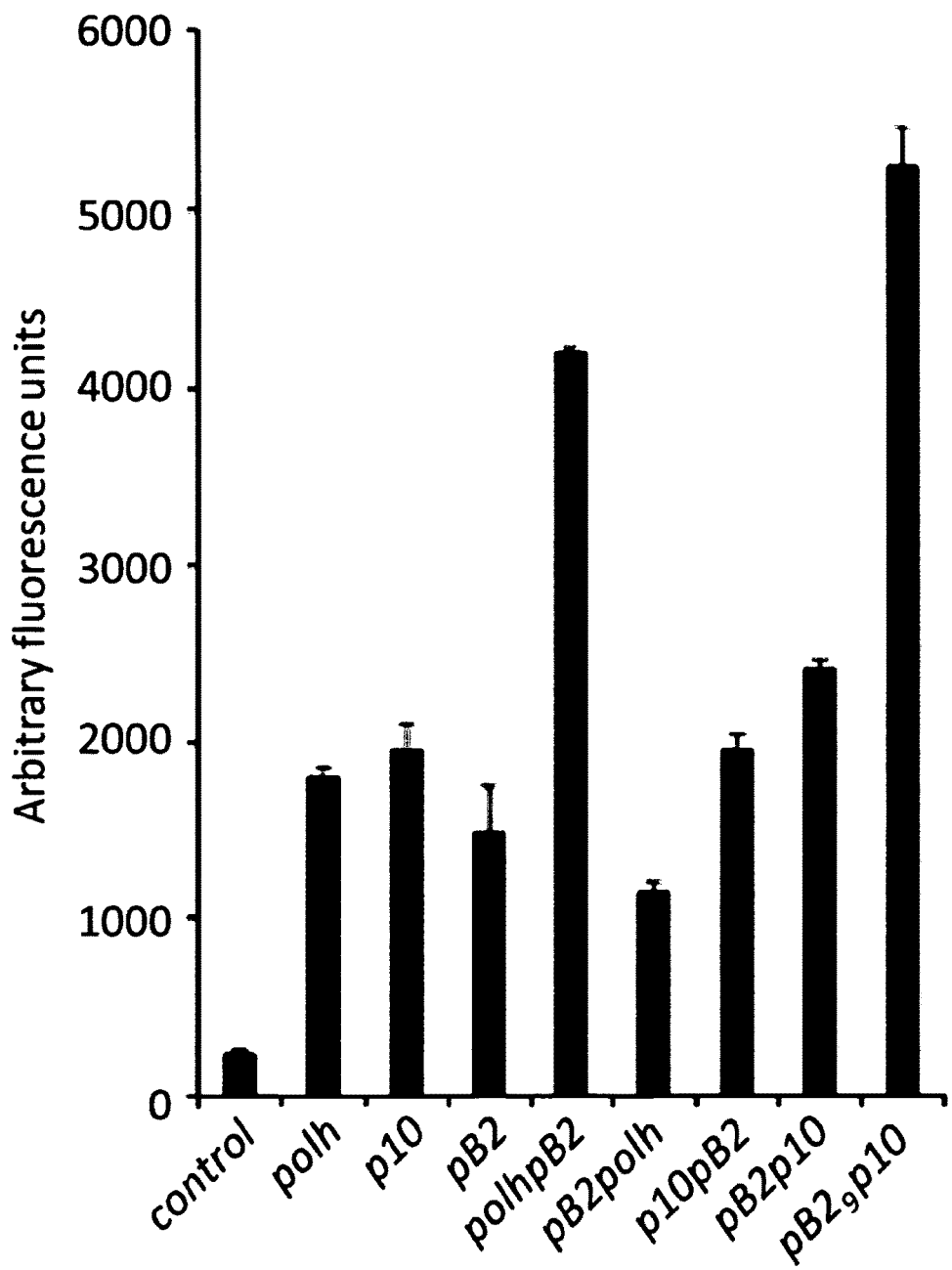
FIG. 10: GFP expression levels mediated by the use of different promoters or combination of promoters. A) Fluorimetric analysis at 24 hours post-infection of Sf21 cells infected with different recombinant baculoviruses expressing the GFP under the control of different individual or chimeric promoters. B) Time course study of the GFP expression in Sf21 cells infected with the same recombinant baculoviruses as in panel A, measured by a fluorimetric assay. All the experiments were done at a MOI of 5 and the figure shows the arithmetic media of three independent experiments with the corresponding standard deviations.
Figure 10:
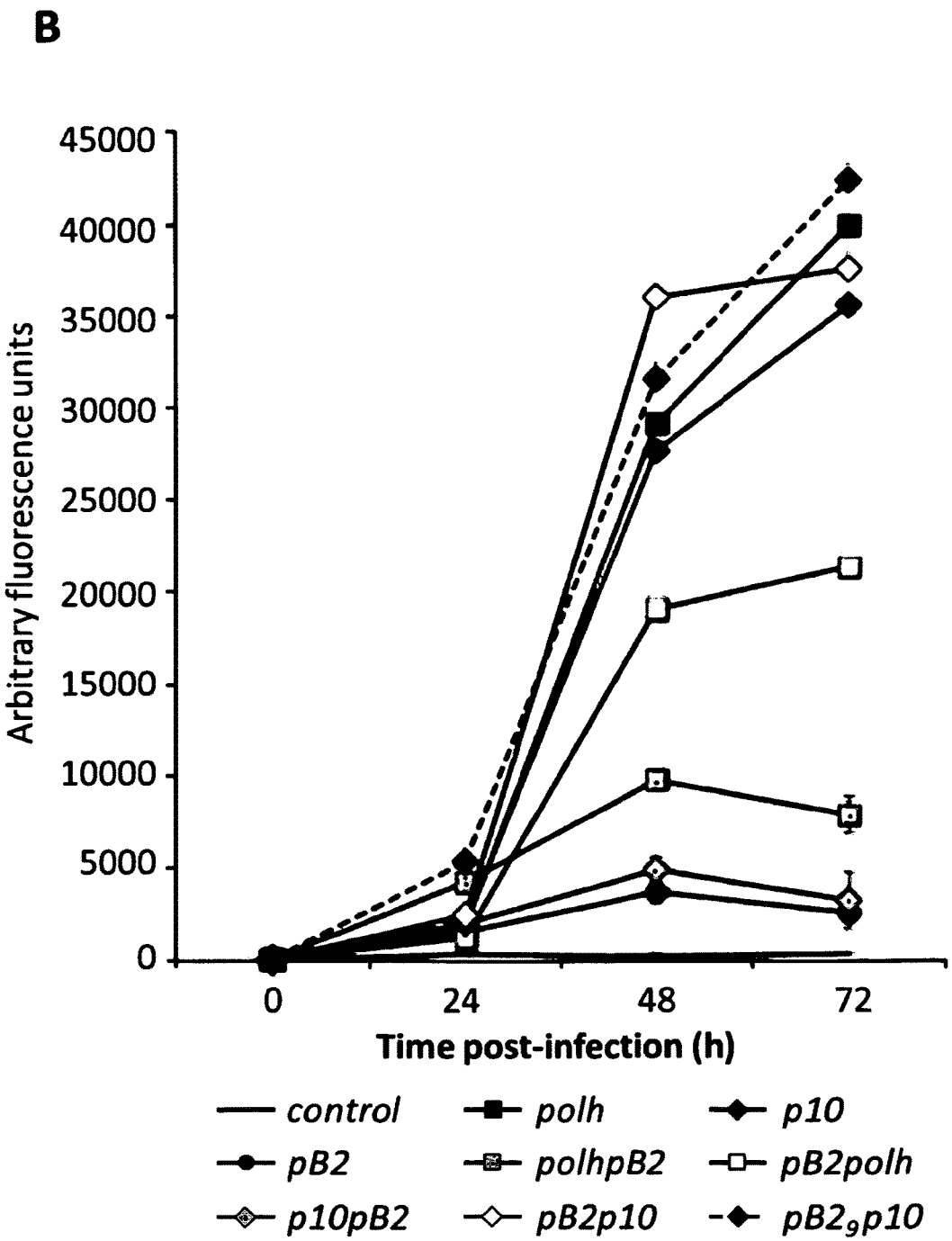

Synergistic Cooperation Between pB2 or pB29 and Conventional Baculovirus Promoters Different chimeric promoters comprising the pB2 or pB2$_9$ sequence and the conventional baculovirus promoters polh or p10 were constructed, resulting in the combinations pB2polh, polhpB2, pB2p10, p10pB2 and pB2$_9$p10. All of them were used to generate recombinant baculoviruses and tested for their promoter characteristics. At 24 hours post-infection, the GFP protein expression driven by polhpB2 and pB2$_9$p10 hybrid promoters was higher than by using the conventional promoters polh or p10 (FIG. 10A). Interestingly, the GFP expression under the control of the chimeric promoter polhpB2 dropped at 48 hours post-infection, while the GFP expressed under the control of the chimeric promoter pB2$_9$p10 increased along time at levels even higher than obtained by using the polh promoter (FIG. 10B). The chimeric promoter pB2p10 showed the maximum GFP expression levels at 48 hours post-infection, but the expression increase was not linear at later times (FIG. 10B). In conclusion, the hybrid promoter pB2$_9$p10 was earlier and stronger than the polh or p10 promoter alone.

BIBLIOGRAPHY

1. Nettleship, J. E., Assenberg, R., Diprose, J. M., Rahman-Huq, N., Owens, R. J. Recent advances in the production of proteins in insect and mammalian cells for structural biology. J. Struct. Biol. 2010, 172, 55-65.
2. Gomez-Casado E, Gomez-Sebastian S, Núñez M C, Lasa-Covarrubias R, Martinez-Pulgarín S, Escribano J M. Insect larvae biofactories as a platform for influenza vaccine production. *Protein Expr Purif.* 79: 35-43. 2011.
3. Smith, G. E., M. D. Summers, and M. J. Fraser. 1983. Production of human beta interferon in insect cells infected with a baculovirus expression vector. Mol. *Cell. Biol.* 3: 2156-21 65.
4. Hitchman R M, Possee R D, King L A. Baculovirus expression systems for recombinant protein production in insect cells. Recent Pat Biotechnol. 2009; 3(1):46-54.
5. Hashimoto Y, Zhang S, Blissard G W. Ao38, a new cell line from eggs of the black witch moth, *Ascalapha odorata* (*Lepidoptera*: Noctuidae), is permissive for AcMNPV infection and produces high levels of recombinant proteins. BMC Biotechnol. 2010, 10:50.
6. Taticek R A, Choi C, Phan S E, Palomares L A, Shuler M L. Comparison of growth and recombinant protein expression in two different insect cell lines in attached and suspension culture. *Biotechnol. Prof.* 2001, 17 (4), 676-684.
7. Hill-Perkins M S, Possee R D. A baculovirus expression vector derived from the basic protein promoter of *Autographa californica* nuclear polyhedrosis virus. J Gen Virol. 1990, 71 (Pt 4):971-6.
8. Passarelli, A. L., and L. K. Miller. Three baculovirus genes involved in late and very late gene expression: ie-1, ie-n, and lef-2. J. Virol. 1993, 67:2149-2158
9. Rodems, S. M., S. S. Pullen, and P. D. Friesen. DNA-dependent transregulation by IE1 of *Autographa californica* nuclear polyhedrosis virus: IE1 domains required for transactivation and DNA binding. J. Virol. 1997, 71: 9270-9277.
10. Lin X, Chen Y, Yi Y, Zhang Z: Baculovirus immediately early 1, a mediator for homologous regions enhancer function in trans. *Virol J* 2010, 7:32.
11. Okano K, Mikhailov V S, Maeda S: Colocalization of baculovirus IE-1 and two DNA-binding proteins, DBP and LEF-3, to viral replication factories. *Journal of virology* 1999, 73(1):110-119.

The invention claimed is:

1. A recombinant baculovirus comprising one native copy of an Ac-ie-01 gene in its genome and a first nucleic acid sequence,
wherein said first nucleic acid sequence comprises an extra copy of the Ac-ie-01 gene under control of a promoter; wherein said recombinant baculovirus is capable of expressing increased levels of immediate early protein (IE-1) or immediate early protein 0 (IE-0) in a host cell infected with said recombinant baculovirus as compared to the host cell infected with a control baculovirus;
wherein the control baculovirus comprises one native copy of the Ac-ie-01 gene in its genome and does not comprise said first nucleic acid sequence;
wherein the host cell is derived from an insect belonging to the species *Trichoplusia ni* or *Spodoptera frugiperda*;

wherein said first nucleic acid sequence comprises a nucleic acid sequence selected from the group consisting of:
a) a nucleic acid sequence comprising any of SEQ ID NOS: 2-5; and
b) a nucleic acid sequence encoding an amino acid sequence comprising any of SEQ ID NOS: 6-9; and wherein said first nucleic acid sequence further comprises at least one recombinant homologous region (hr) from a baculovirus as enhancer region, wherein said recombinant homologous region (hr) is operably linked to a promoter suitable for driving the expression of a recombinant protein;

wherein the promoter is a nucleic acid sequence comprising any of SEQ ID NOS: 10-16.

2. The recombinant baculovirus according to claim 1, wherein the recombinant homologous region (hr) consists of SEQ ID NO: 27 (hr1).

3. The recombinant baculovirus according to claim 1, comprising a nucleic acid sequence selected from the group consisting of SEQ ID NOS: 17-26.

4. The recombinant baculovirus according to claim 1, further comprising a second nucleic acid sequence encoding a recombinant protein, wherein said second nucleic acid sequence is operably linked to said first nucleic acid sequence, said recombinant homologous region (hr) or said promoter.

5. A host cell infected with the recombinant baculovirus of claim 1, wherein said host cell is derived from an insect belonging to the species *Trichoplusia ni* or *Spodoptera frugiperda*.

6. The host cell according to claim 5, wherein said host cell is derived from an insect cell line selected from the group consisting of Hi-5™, Sf9, Sf21, BTI-Tn5B-1, Tn368, ExpresSf+® and BTI-TnAo38.

7. A method for producing a recombinant protein, the method comprising expressing said protein in the host cell according to claim 5 and extracting and purifying said recombinant protein.

* * * * *